United States Patent
Wang et al.

(10) Patent No.: US 11,267,806 B2
(45) Date of Patent: Mar. 8, 2022

(54) INDAZOLE COMPOUND FOR USE IN INHIBITING KINASE ACTIVITY, COMPOSITION AND APPLICATION THEREOF

(71) Applicant: Shenzhen TargetRx, Inc., Guangdong (CN)

(72) Inventors: Yihan Wang, Guangdong (CN); Huanyin Li, Guangdong (CN)

(73) Assignee: Shenzhen TargetRx, Inc., Guangdong (CN)

( * ) Notice: Subject to any disclaimer, the term of this patent is extended or adjusted under 35 U.S.C. 154(b) by 72 days.

(21) Appl. No.: 16/625,009

(22) PCT Filed: Jun. 25, 2018

(86) PCT No.: PCT/CN2018/092570
§ 371 (c)(1),
(2) Date: Dec. 20, 2019

(87) PCT Pub. No.: WO2019/001379
PCT Pub. Date: Jan. 3, 2019

(65) Prior Publication Data
US 2020/0140419 A1 May 7, 2020

(30) Foreign Application Priority Data

Jun. 26, 2017 (CN) .......................... 201710493792.4

(51) Int. Cl.
*C07D 405/12* (2006.01)

(52) U.S. Cl.
CPC ........ *C07D 405/12* (2013.01); *C07B 2200/05* (2013.01)

(58) Field of Classification Search
None
See application file for complete search history.

(56) References Cited

U.S. PATENT DOCUMENTS

| | | | | |
|---|---|---|---|---|
| 2010/0292207 | A1* | 11/2010 | Lombardi Borgia | A61P 3/10 514/210.21 |
| 2019/0241546 | A1 | 8/2019 | Lombardi Borgia et al. | |

FOREIGN PATENT DOCUMENTS

| | | |
|---|---|---|
| CN | 101754956 A | 6/2010 |
| CN | 102603734 A | 7/2012 |
| JP | 2011-502959 A | 1/2011 |

OTHER PUBLICATIONS

Extended European Search Report for Application No. EP 18825179.7, dated Feb. 7, 2020.

International Search Report and Written Opinion for Application No. PCT/CN2018/092570, dated Sep. 30, 2018.
[No Author Listed] Precision Deuterium Chemistry Backgrounder. Concert Pharmaceuticals, Inc. Jan. 1, 2007. Retrieved from the internet: http://www.webcitation.org/5e81SGCnl. 6 pages.
Menichincheri et al., Discovery of Entrectinib: A New 3-Aminoindazole As a Potent Anaplastic Lymphoma Kinase (ALK), c-ros Oncogene 1 Kinase (ROS1), and Pan-Tropomyosin Receptor Kinases (Pan-TRKs) inhibitor [published correction appears in J Med Chem. Sep. 12, 2019;62(17):8364], J Med Chem. 2016;59(7):3392-3408. doi:10.1021/acs.jmedchem.6b00064.
Japanese Office Action for Application No. 2020-520705, dated Feb. 24, 2021.
Buteau, Deuterated Drugs: Unexpectedly Nonobvious? J High Tech Law. 2009; X(1):22-74.
No Author Listed, Declaration Under 37 CFR 1.132 of Vinita Uttamsingh, dated Feb. 1, 2012. 3 pages.
(Continued)

*Primary Examiner* — Joseph R Kosack
(74) *Attorney, Agent, or Firm* — Wolf, Greenfield & Sacks, P.C.

(57) ABSTRACT

The present invention relates to an indazole compound for use in inhibiting kinase activity, and relates to a preparation and use thereof. Specifically disclosed in the present invention is an indazole compound represented by formula (I), or a crystal form, a prodrug, a pharmaceutically acceptable salt, a stereoisomer, a tautomer, a solvate or a hydrate thereof, or a pharmaceutical composition thereof. The compound of the present invention and the composition containing the compound have an excellent inhibitory effect on kinase proteins, and have better pharmacokinetic parameter characteristics, may increase the drug concentration of the compound in an animal, and improve the efficacy and safety of the drug.

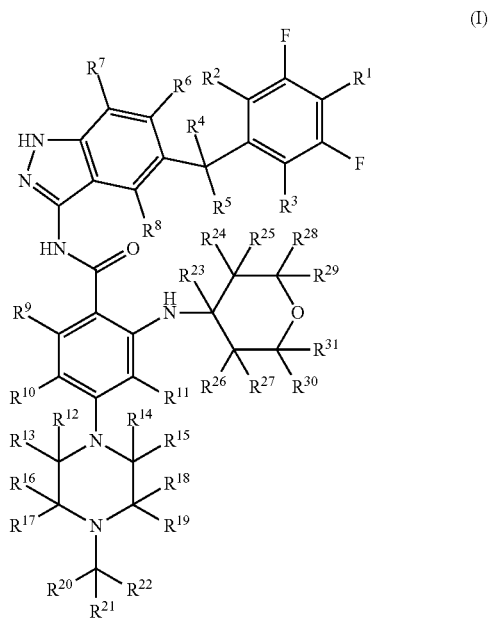

(I)

22 Claims, No Drawings

(56) References Cited

OTHER PUBLICATIONS

Harbeson et al., Deuterium in Drug Discovery and Development. Ann Rep Med Chem. 2011; 46:403-417.
Shao et al., Derivatives of tramadol for increased duration of effect. Bioorg Med Chem Lett. Feb. 2006;16(3):691-4. doi: 10.1016/j.bmcl. 2005.10.024. Epub Oct. 27, 2005.

* cited by examiner

INDAZOLE COMPOUND FOR USE IN INHIBITING KINASE ACTIVITY, COMPOSITION AND APPLICATION THEREOF

CROSS REFERENCE TO RELATED APPLICATIONS

The present application is a national application of PCT/CN2018/092570 filed on Jun. 25, 2018, which claims the priority of the Chinese Patent Application No. 201710493792.4 filed on Jun. 26, 2017. The Chinese Patent Application No. 201710493792.4 is incorporated herein by reference as part of the disclosure of the present application.

TECHNICAL FIELD

The present disclosure belongs to the pharmaceutical field, and in particular, the present disclosure relates to a substituted indazole compound having an activity of inhibiting protein kinase. More particularly, the present disclosure relates to some deuterated N-(5-(3,5-difluorobenzyl)-1H-indazol-3-yl)-4-(4-methylpiperazin-1-yl)-2-((tetrahydro-2H-pyran-4-yl)amino)benzamide. These deuterated compounds and compositions thereof can be used to treat relevant cancers mediated by ALK, ROS1, TRK1, TRK2, TRK3 or the like, and these deuterated compounds have more excellent pharmacokinetic properties.

BACKGROUND OF THE INVENTION

The malfunction of protein kinases (PKs) is a hallmark of numerous diseases. A large share of oncogenes and proto-oncogenes involved in human cancers encode PKs. The enhanced activities of PKs are also involved in many non-malignant diseases, such as benign prostate hyperplasia, familial adenomatosis, polyposis, neurofibromatosis, psoriasis, vascular smooth cell proliferation associated with atherosclerosis, pulmonary fibrosis, arthritis, glomerulonephritis and post-surgical stenosis and restenosis.

PKs are also involved in inflammatory conditions and the proliferation of viruses and parasites. PKs may also play an important role in the pathogenesis and development of neurodegenerative diseases.

PK malfunction or deregulation can be found in references, for example, Current Opinion in Chemical Biology 1999, 3, 459-465.

Ignyta's new anti-tumor drug, Entrectinib, received a breakthrough therapy from FDA in May 2017 for the treatment of NTRK gene fusion-positive, locally advanced or metastatic solid tumors in adults and children, in which the disease still progresses after receiving existing therapies, or there is no standard therapy for the disease in these patients. Entrectinib is a novel oral tyrosine kinase inhibitor (TKI) with central nervous activity, which targets tumors containing NTRK1/2/3, ROS1 or ALK gene fusion mutations.

Entrectinib is currently the only tyrosine kinase inhibitor clinically proven to be active against primary and metastatic cancers in the central nervous system and has no adverse off-target effects. The drug candidate is undergoing Phase 2 clinical trial STARTRK-2, which is a global multi-center, open-label, registration-related phase 2 clinical trial. The clinical trial uses the concept of "basket design" in the precision medicine, wherein the tumor patients are screened for their gene mutations at the time of enrollment, and they are assigned to different "baskets" for treatment depending on the type of tumor and gene fusion. This "basket design" can encompass a range of different tumor types to validate clinical effects of Entrectinib against molecular targets.

It is known that poor absorption, distribution, metabolism, and/or excretion (ADME) property is the main cause of clinical trial failure in many drug candidates. Currently, many marketed drugs have limited range of application due to poor ADME. The rapid metabolism can lead to effective drugs that could treat diseases unable to be used as a drug because they are too quickly removed from the body. Although a frequent or high-dose administration may solve the problem of rapid drug clearance, this approach can lead to problems such as poor patient compliance, side effects caused by the high-dose administration, and increased cost in the treatment. In addition, drugs that are rapidly metabolized may also expose patients to undesirable toxic or reactive metabolites.

Therefore, there is an unmet clinical need in the filed for a wide therapeutic potential for most tumor types, and a resolution for the problem of lack of treatment means.

SUMMARY OF THE INVENTION

In view of the above technical problems, disclosed herein are a novel deuterated indazole compound, a pharmaceutical composition and use thereof. The novel deuterated indazole compound has better kinase inhibitory activity and/or better pharmacodynamic/pharmacokinetic properties.

In this regard, the technical solution provided by the present disclosure is:

a substituted indazole compound, characterized by an indazole compound of formula (I), or a pharmaceutically acceptable salt, a prodrug, a crystalline form, a stereoisomer, a tautomer, a hydrate or a solvate thereof:

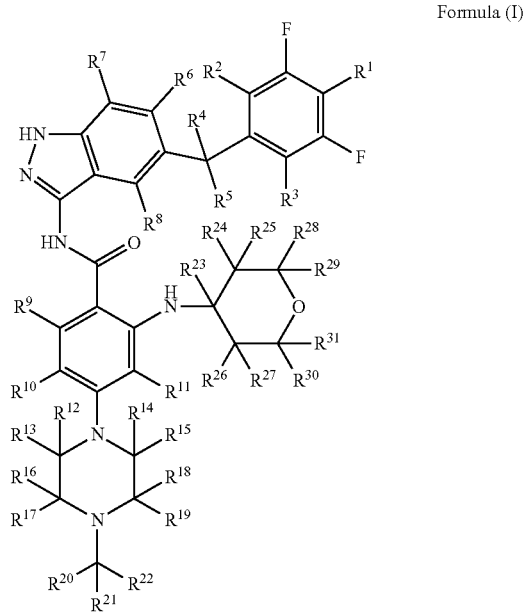

Formula (I)

wherein:
$R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$ and $R^{31}$ are each independently selected from the group consisting of hydrogen, deuterium, halogen and trifluoromethyl;

with the proviso that: at least one of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$ and $R^{31}$ is deuterated or deuterium.

With the technical solution wherein the hydrogen in the drug molecule is selectively replaced with deuterium, the deuterated drug generally retains the original biological activity and selectivity, as in the drug molecule the shape and volume of deuterium are substantially the same as those of hydrogen. At the same time, the inventors have confirmed through experiments that the binding of the carbon-deuterium bond is more stable than that of the carbon-hydrogen bond, which may directly affect the properties, such as absorption, distribution, metabolism and excretion, of some drugs, thereby improving the efficacy, safety and tolerability of the drugs.

Preferably, the content of the deuterium isotope at the deuterated position is at least greater than the natural content of the deuterium isotope (0.015%), preferably greater than 30%, more preferably greater than 50%, more preferably greater than 75%, more preferably greater than 95%, and more preferably greater than 99%.

Specifically, in the present disclosure, the content of the deuterium isotope in each deuterated position of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$ and $R^{31}$ is at least 5%, preferably greater than 10%, more preferably greater than 15%, more preferably greater than 20%, more preferably greater than 25%, more preferably greater than 30%, more preferably greater than 35%, more preferably greater than 40%, more preferably greater than 45%, more preferably greater than 50%, more preferably greater than 55%, more preferably greater than 60%, more preferably greater than 65%, more preferably greater than 70%, more preferably greater than 75%, more preferably greater than 80%, more preferably greater than 85%, more preferably greater than 90%, more preferably greater than 95%, and more preferably greater than 99%.

Preferably, in $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$ and $R^{31}$ of the compound of formula (I), at least one of these Rs contains deuterium, more preferably two Rs contain deuterium, more preferably three Rs contain deuterium, more preferably four Rs contain deuterium, more preferably five Rs contain deuterium, more preferably six Rs contain deuterium, more preferably seven Rs contain deuterium, more preferably eight Rs contain deuterium, more preferably nine Rs contain deuterium, more preferably ten Rs contain deuterium, more preferably eleven Rs contain deuterium, more preferably twelve Rs contain deuterium, more preferably thirteen Rs contain deuterium, more preferably fourteen Rs contain deuterium, more preferably fifteen Rs contain deuterium, more preferably sixteen Rs contain deuterium, more preferably seventeen Rs contain deuterium, more preferably eighteen Rs contain deuterium, more preferably nineteen Rs contain deuterium, more preferably twenty Rs contain deuterium, more preferably twenty-one Rs contain deuterium, more preferably twenty-two Rs contain deuterium, more preferably twenty-three Rs contain deuterium, more preferably twenty-four Rs contain deuterium, more preferably twenty-five Rs contain deuterium, more preferably twenty-six Rs contain deuterium, more preferably twenty-seven Rs contain deuterium, more preferably twenty-eight Rs contain deuterium, more preferably twenty-nine Rs contain deuterium, more preferably thirty Rs contain deuterium, and more preferably thirty-one Rs contain deuterium.

As a further embodiment disclosed herein, $R^1$, $R^2$, and $R^3$ are each independently selected from deuterium or hydrogen.

In another preferred embodiment, $R^1$ is deuterium.

As a further embodiment disclosed herein, $R^4$ and $R^5$ are each independently selected from deuterium or hydrogen.

In another preferred embodiment, $R^4$ and $R^5$ are deuterium.

As a further embodiment disclosed herein, $R^6$, $R^7$, and $R^8$ are each independently selected from deuterium or hydrogen.

In another preferred embodiment, $R^6$, $R^7$, and $R^8$ are deuterium.

As a further embodiment disclosed herein, $R^9$, $R^{10}$, and $R^{11}$ are each independently selected from deuterium or hydrogen.

In another preferred embodiment, $R^{10}$ and $R^{11}$ are deuterium.

As a further embodiment disclosed herein, $R^{12}$, $R^{13}$, $R^{14}$, $R^{15}$, $R^{16}$, $R^{17}$, $R^{18}$, and $R^{19}$ are each independently selected from deuterium or hydrogen.

In another preferred embodiment, $R^{12}$, $R^{13}$, $R^{14}$, $R^{15}$, $R^{16}$, $R^{17}$, $R^{18}$, and $R^{19}$ are deuterium.

As a further embodiment disclosed herein, $R^{20}$, $R^{21}$, and $R^{22}$ are each independently selected from deuterium or hydrogen.

In another preferred embodiment, $R^{20}$, $R^{21}$, and $R^{22}$ are deuterium.

As a further embodiment disclosed herein, $R^{23}$, $R^{24}$, $R^{25}$, $R^{26}$, $R^{27}$, $R^{28}$, $R^{29}$, $R^{30}$ and $R^{31}$ are each independently selected from deuterium or hydrogen.

In another preferred embodiment, $R^{28}$, $R^{29}$, $R^{30}$, and $R^{31}$ are deuterium.

As a further embodiment disclosed herein, the compound is selected from the group consisting of the following compounds and a pharmaceutically acceptable salt thereof:

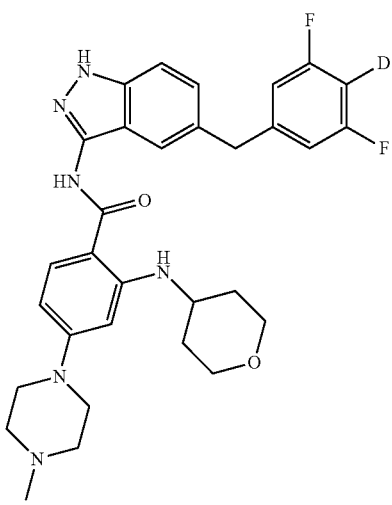

Formula (1)

Formula (2)
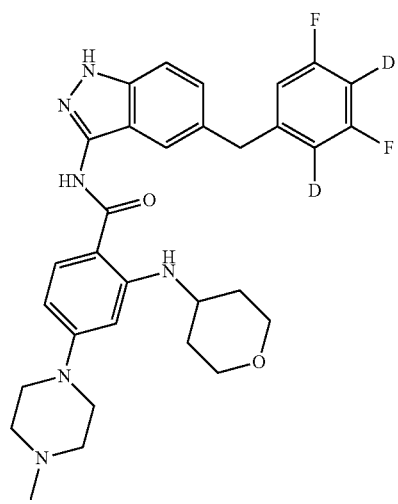
Formula (3)
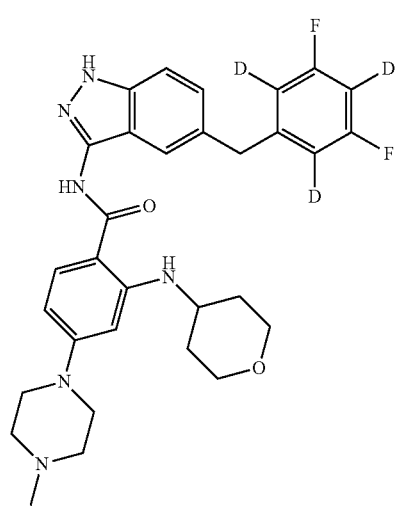
Formula (4)
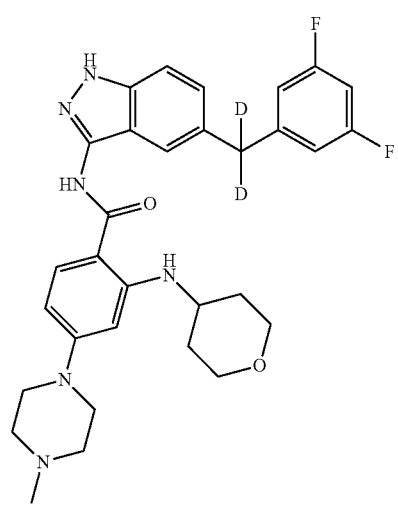
Formula (5)
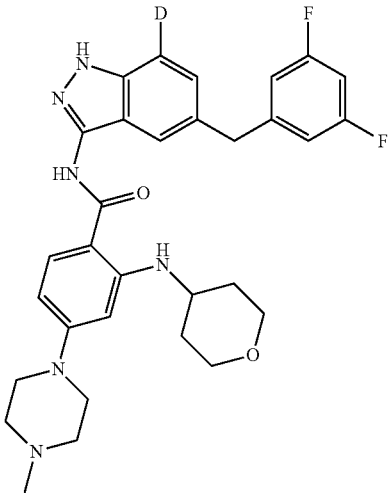
Formula (6)
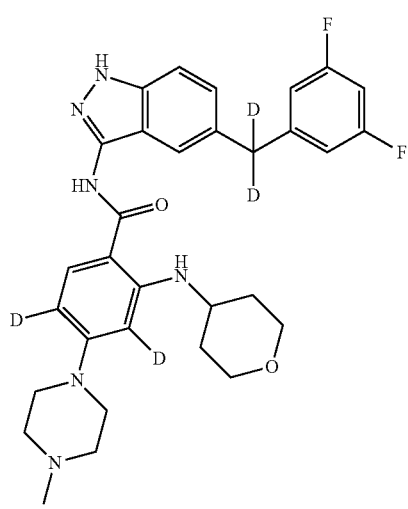
Formula (7)
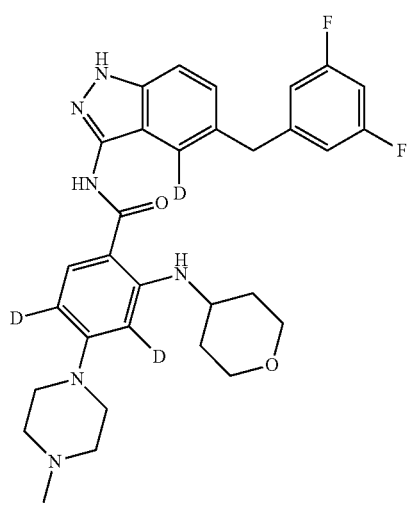

Formula (8)
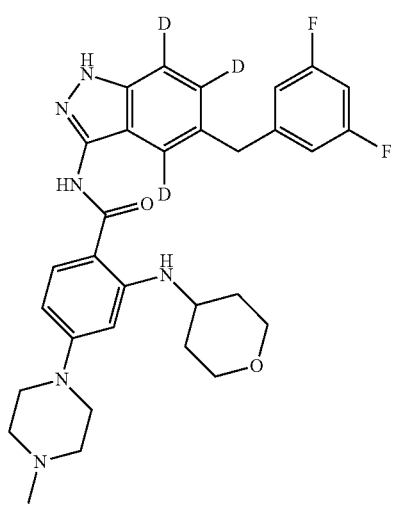
Formula (9)
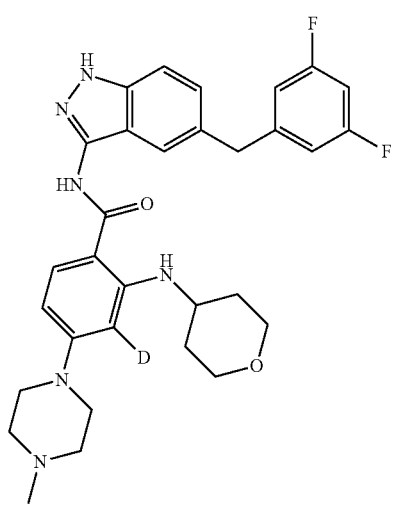
Formula (10)
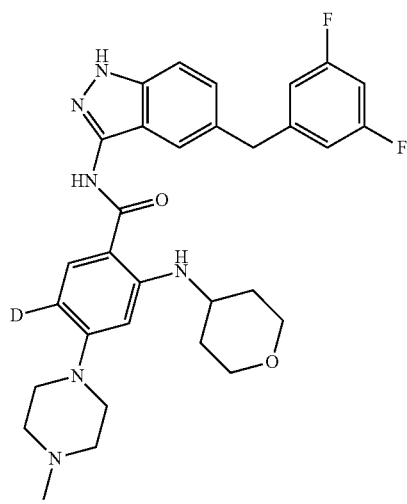
Formula (11)
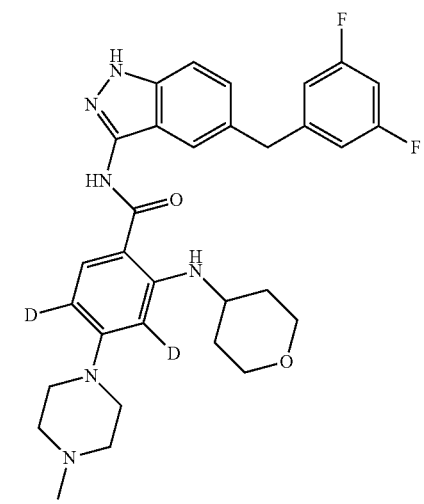
Formula (12)
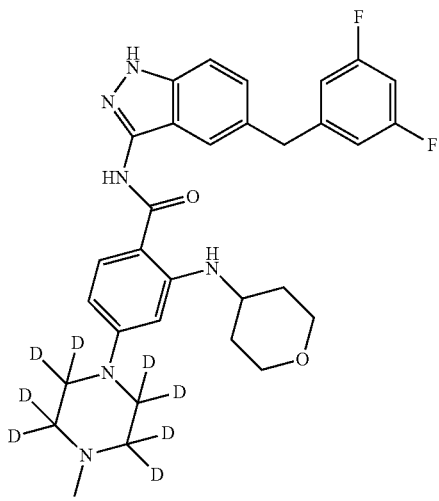
Formula (13)
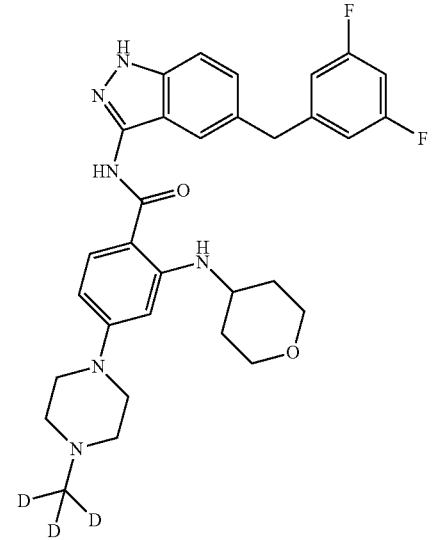

Formula (14)
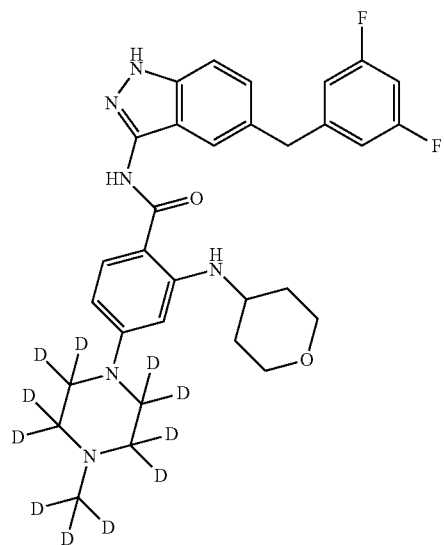
Formula (15)
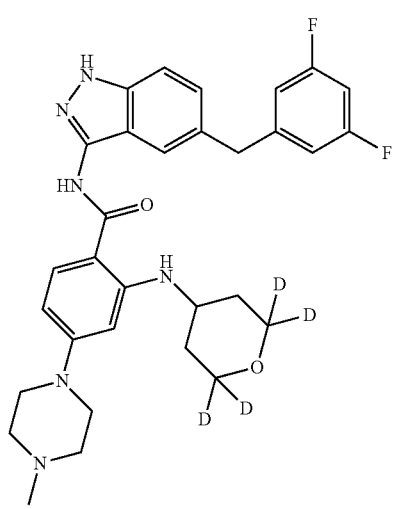
Formula (16)
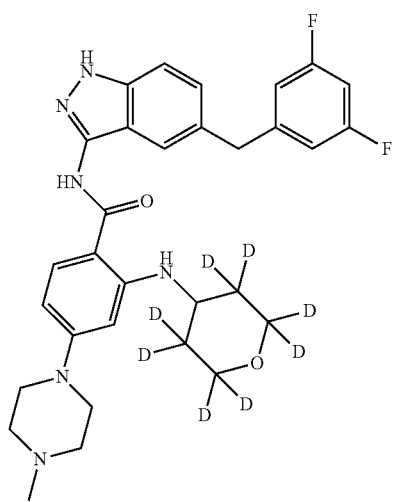
Formula (17)
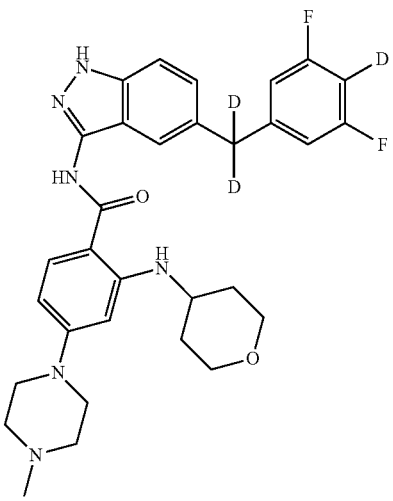
Formula (18)
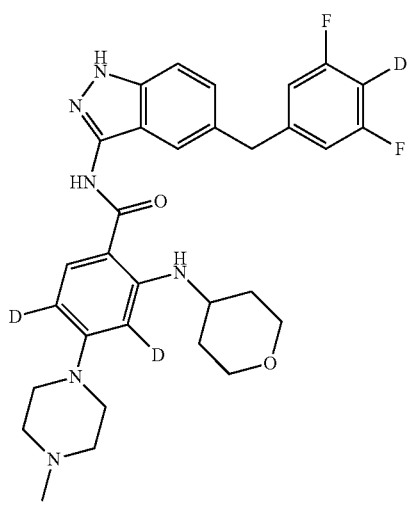
Formula (19)
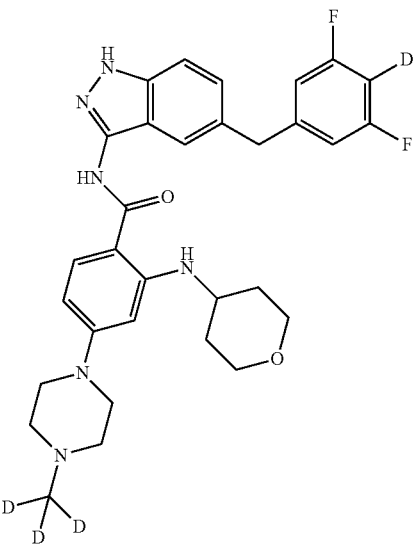

-continued
Formula (20)
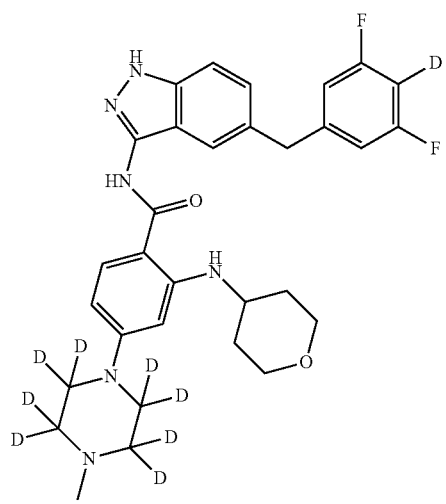
Formula (21)
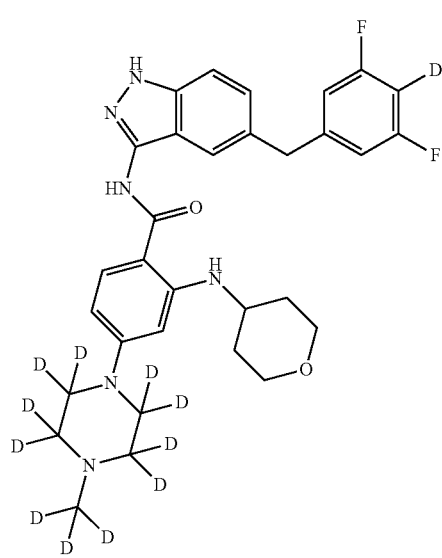
Formula (22)
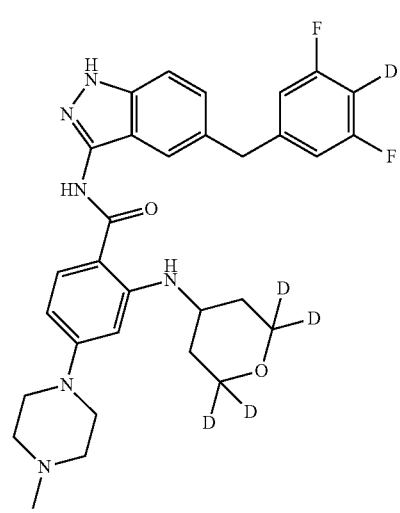
-continued
Formula (23)
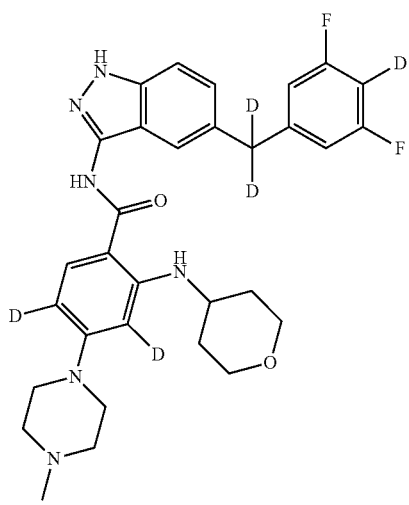
Formula (24)
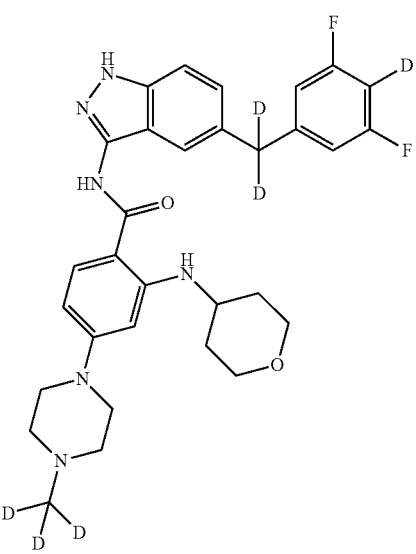
Formula (25)
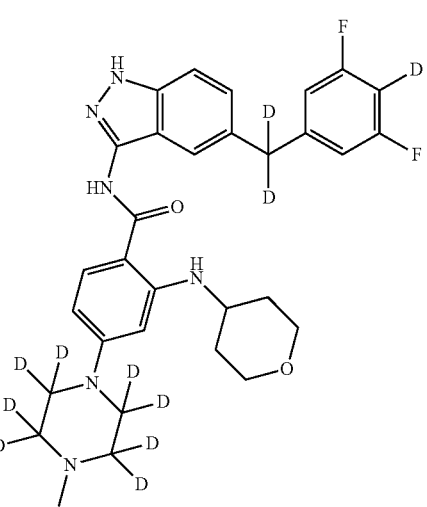

Formula (26)
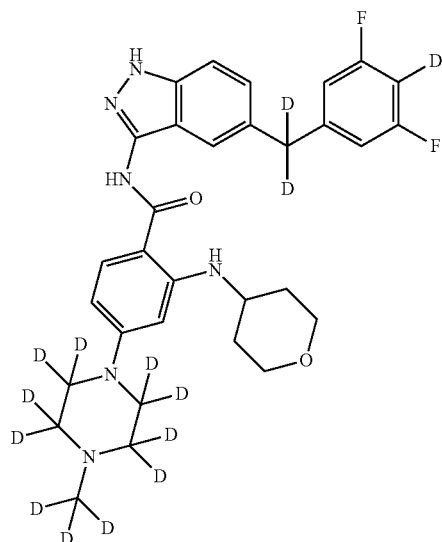
Formula (27)
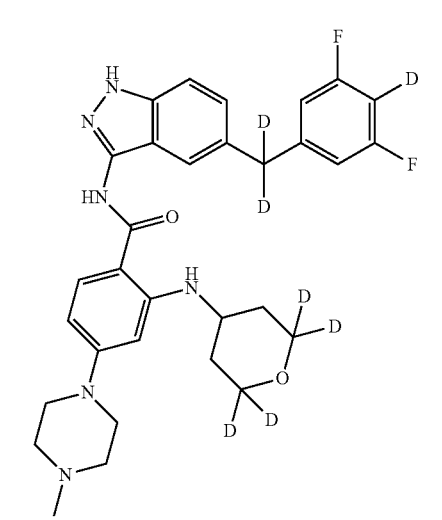
Formula (28)
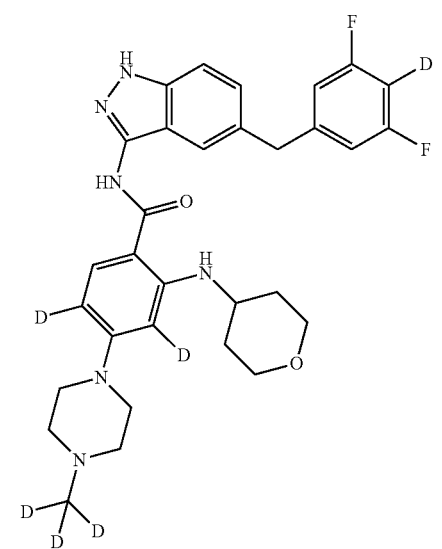
Formula (29)
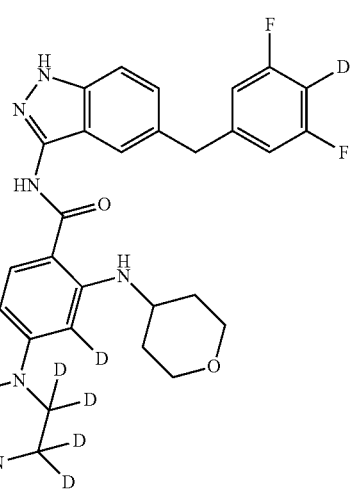
Formula (30)
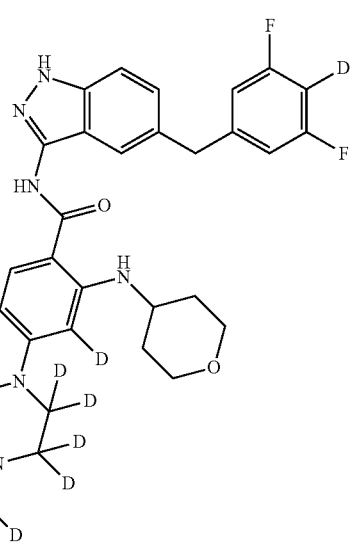
Formula (32)
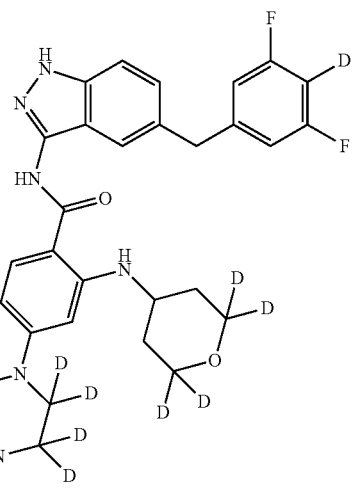

Formula (37)
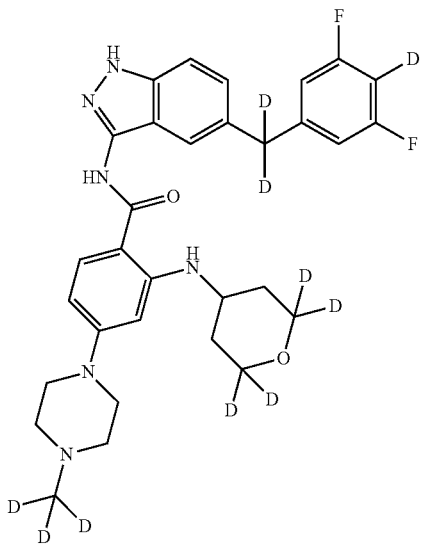
Formula (38)
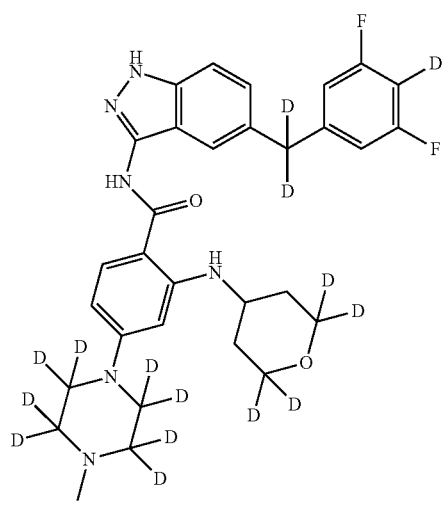
Formula (39)
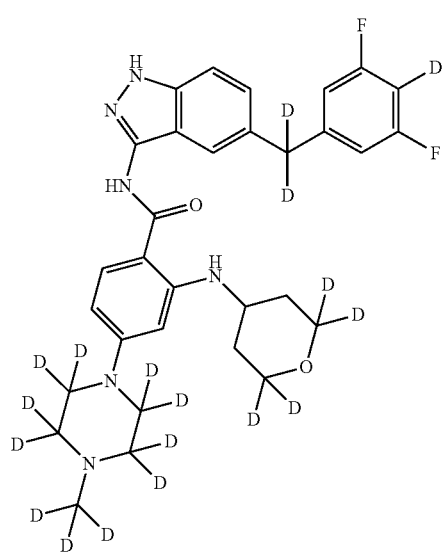
Formula (43)
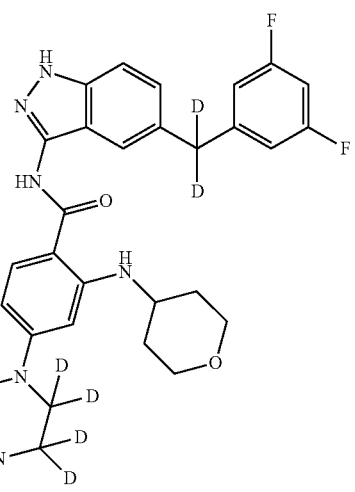
Formula (44)
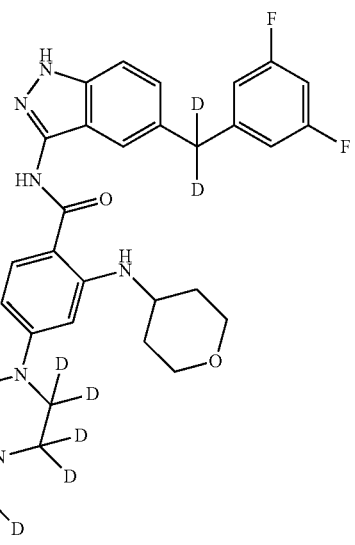
Formula (45)
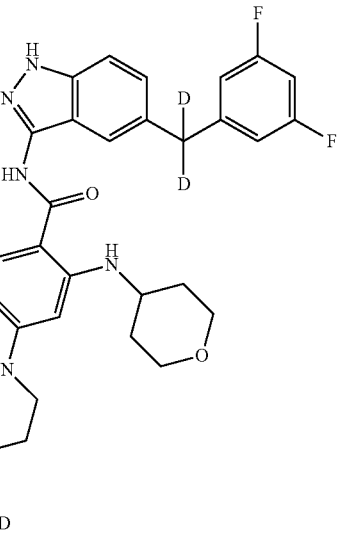

Formula (46)
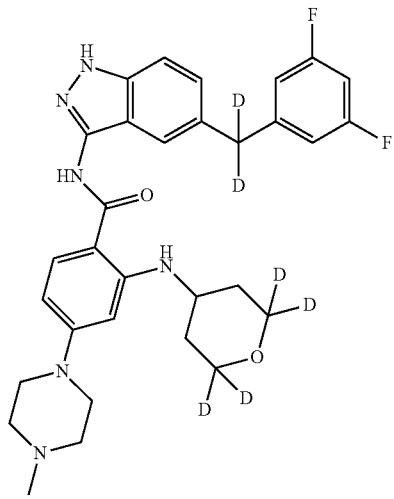
Formula (47)
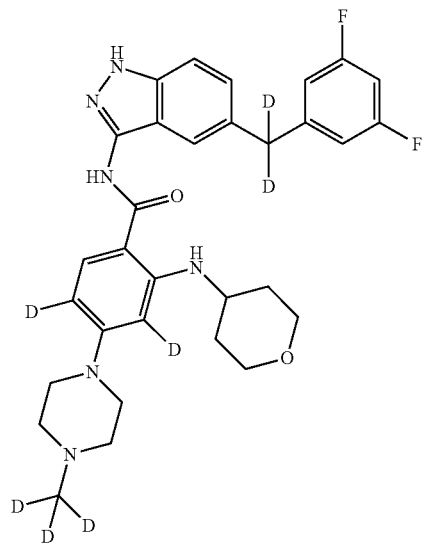
Formula (48)
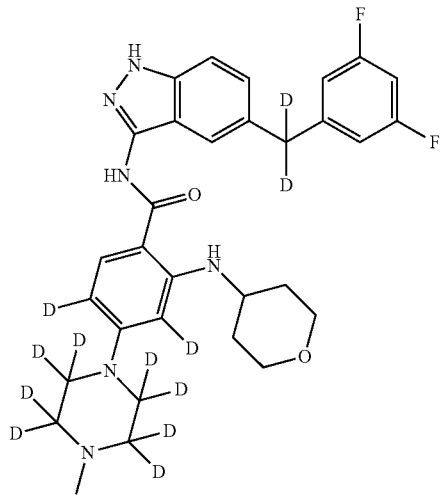
Formula (49)
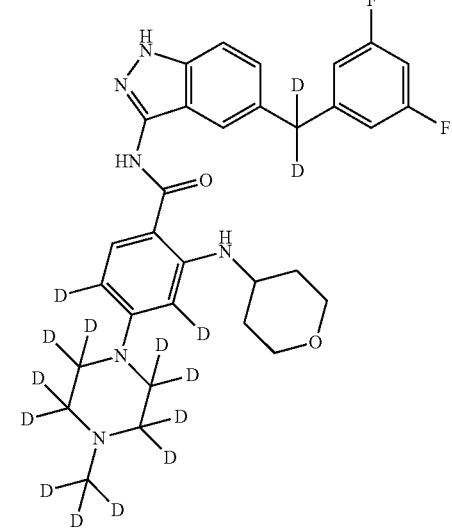
Formula (50)
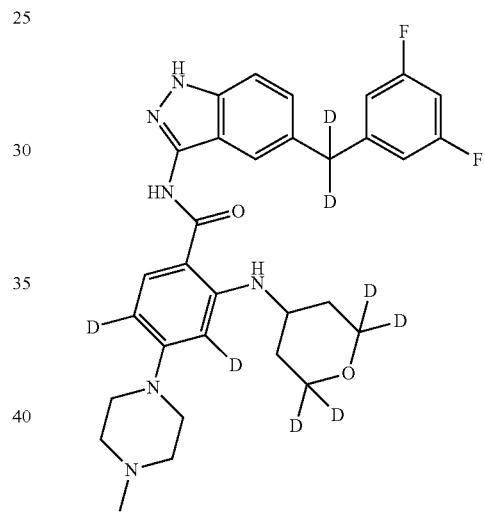
Formula (51)
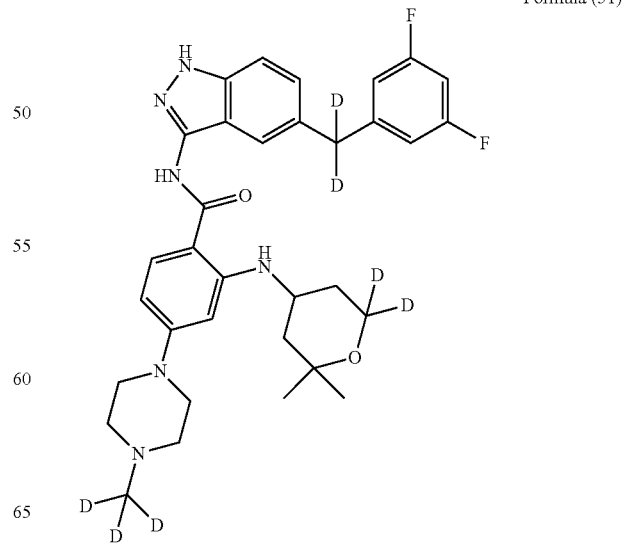

Formula (52)
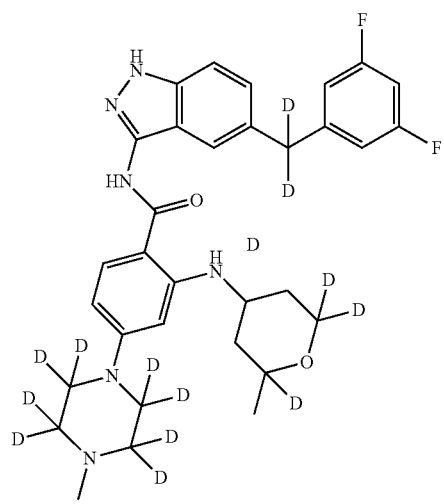
Formula (53)
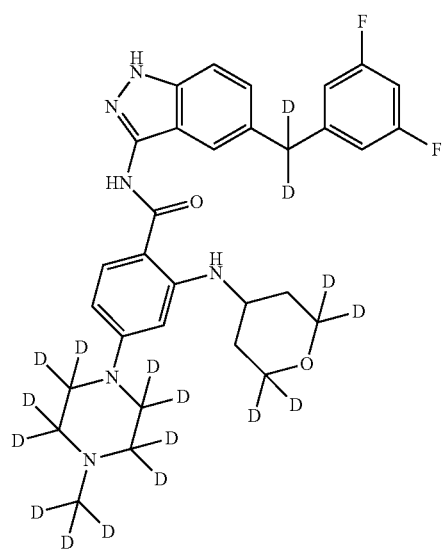
Formula (54)
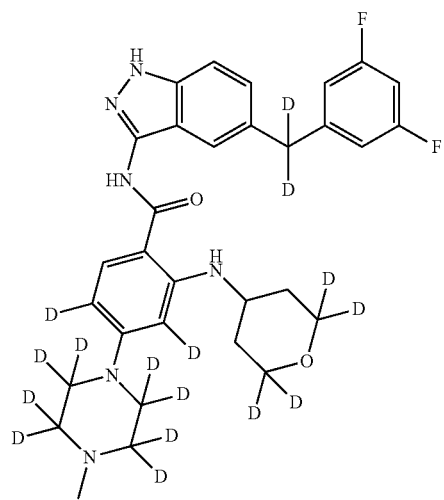
Formula (55)
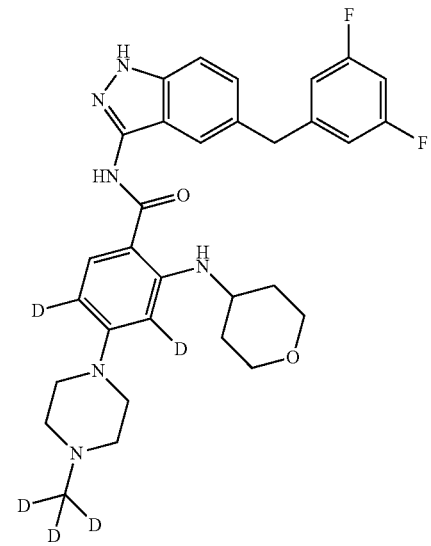
Formula (56)
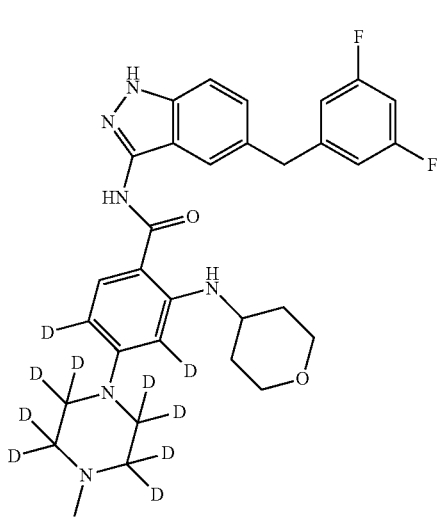
Formula (57)
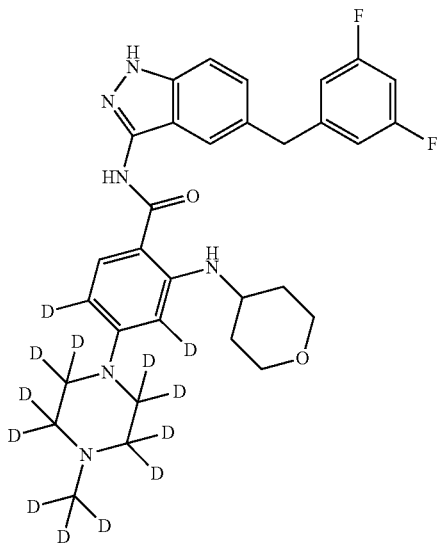

Formula (58)
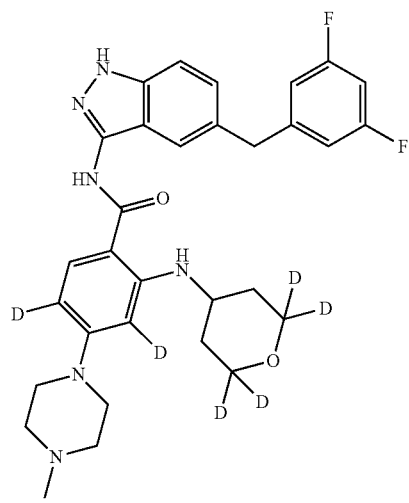
Formula (59)
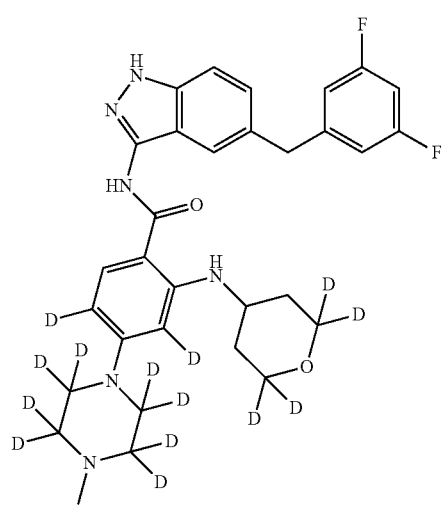
Formula (60)
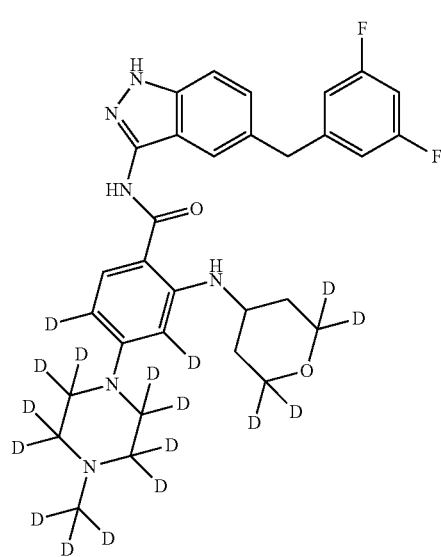
Formula (61)
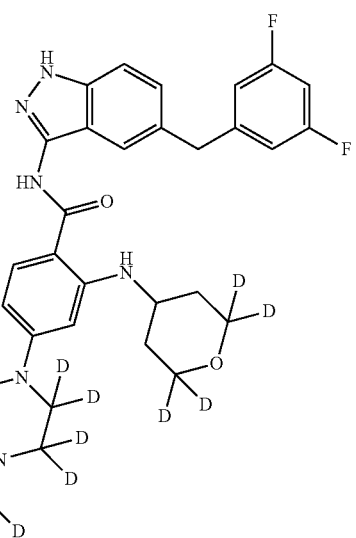
Formula (62)
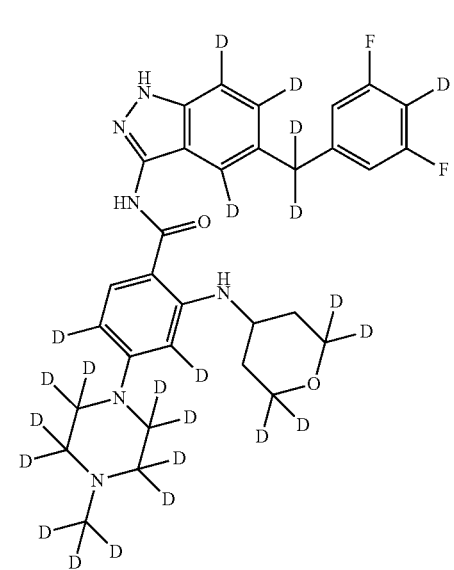

Formula (63)

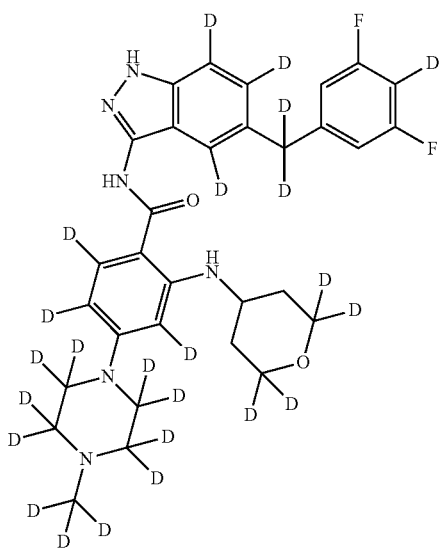

Formula (64)

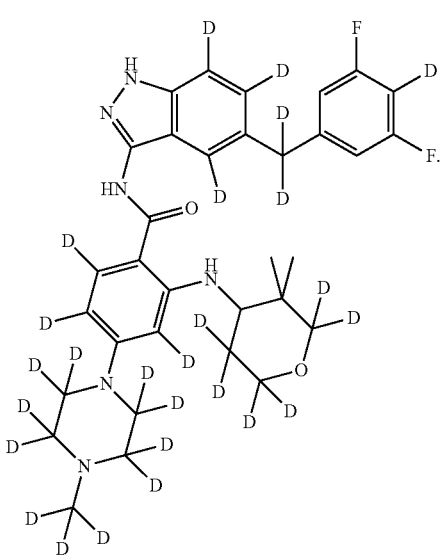

In another preferred embodiment, the compound does not include a non-deuterated compound.

Also disclosed herein is a pharmaceutical composition comprising a pharmaceutically acceptable carrier and a substituted indazole compound as described above, or a crystalline form, a pharmaceutically acceptable salt, a hydrate, a solvate, a stereoisomer, a tautomer, a prodrug or an isotopic variant thereof.

As a further embodiment disclosed herein, the pharmaceutically acceptable carrier comprises at least one of a substance or an additive, a glidant, a sweetener, a diluent, a preservative, a dye/a colorant, a flavor enhancer, a surfactant, a wetting agent, a dispersing agent, a disintegrating agent, a suspending agent, a stabilizer, an isotonic agent, a solvent or an emulsifier encapsulated in a capsule.

As a further embodiment disclosed herein, the pharmaceutical composition is a tablet, a pill, a capsule, a powder, a granule, an ointment, an emulsion, a suspension, a solution, a suppository, an injection, an inhalant, a gel, a microsphere or an aerosol.

Typical routes of administration of the pharmaceutical compositions disclosed herein include, but are not limited to, oral, rectal, transmucosal, enteral, topical, transdermal, inhalation, parenteral, sublingual, intravaginal, intranasal, intraocular, intraperitoneal, intramuscular, subcutaneous, intravenous administration. The oral administration or injection administration is preferred.

The pharmaceutical composition disclosed herein can be produced by a method known in the art, such as a conventional mixing method, a dissolution method, a granulation method, a sugar-coating method, a pulverization method, an emulsification method, a freeze-drying method, and the like.

The present disclosure also provides a method of preparing a pharmaceutical composition comprising the steps of: mixing the pharmaceutically acceptable carrier(s) and the compound of formula (I) as described above, or a crystalline form, a pharmaceutically acceptable salt, a hydrate, a solvate, a stereoisomer, a prodrug or an isotopic variant.

As a further embodiment disclosed herein, the pharmaceutical composition further comprises other active compounds which may be selected from the group consisting of antihormonal agents (e.g., antiestrogens, antiandrogens, and aromatase inhibitors), topoisomerase I inhibitors, topoisomerase II inhibitors, microtubule-targeting drugs, platinum drugs, alkylating agents, DNA damaging or intercalating agents, antineoplastic agents, antimetabolites, other kinase inhibitors, other anti-angiogenic factors, kinesin inhibitors, therapeutically monoclonal antibodies, mTOR inhibitors, histone deacetylase inhibitors, farnesyltransferase inhibitors, and inhibitors of hypoxia response.

The active ingredients disclosed herein may also be used in combination with other active ingredients. The choice of such combination is based on the condition of the treatment, the cross-reactivity of the ingredients, and the combined pharmaceutical properties. It is also possible to administer any of the compounds disclosed herein in combination with one or more other active ingredients to a patient simultaneously in a single dosage form or sequentially. Combination therapies can be administered in a regimen of simultaneous or sequential administration. When administered sequentially, the combination can be administered in two or more administrations. Combination therapy may provide "synergism" or "synergistic effects", in other words, when the active ingredients are used together, the effect obtained is greater than the sum of the effects obtained by using the compounds separately. When the active ingredients are: (1) co-formulated and administered, or delivered simultaneously in a combined formulation; (2) administered alternately or parallel as separate formulations; or (3) administered by some other regimens, synergistic effects may be obtained. When delivered in an alternate therapy, synergistic effects may be obtained when the compounds are administered or released sequentially, for example, as separate tablets, pills or capsules, or by separate injections of separate syringes. Generally, during an alternate therapy, the effective dose of each active ingredient is administered sequentially, i.e., successively, while in a combination therapy, the effective doses of two or more active ingredients are administered together.

The present disclosure also provides a method of treating a disease caused by and/or associated with deregulation of activity of a protein kinase, particularly a PLK family, different isoforms of protein kinase C, Met, PAK-4, PAK-5, ZC-1, STLK-2, DDR-2, Aurora 1, Aurora 2, Bub-1, Chk1, Chk2, HER2, rafl, MEK1, MAPK, EGF-R, PDGF-R, FGF-R, FLT3, JAK2, IGF-R, ALK, PI3K, week kinase, Src, Abl, Akt, MAPK, ILK, MK-2, IKK-2, Cdc7, Nek, Cdk/cyclin kinase family, more particularly Aurora 2, IGF-1R and ALK, and further particularly ALK, the method comprising administering to a mammal in need thereof an effective amount of the substituted indazole compound of formula (I) as defined above.

The present disclosure also provides a method of treating a disease caused by and/or associated with deregulation of activity of a protein kinase which is selected from the group consisting of ALK, ROS1, TRK1, TRK2, TRK3, etc., and the method comprising administering to a mammal in need thereof an effective amount of the substituted indazole compound of formula (I) as defined above.

A preferred method disclosed herein is the treatment of a disease caused by and/or associated with deregulation of activity of a protein kinase, wherein the disease is selected from the group consisting of cancers and cell proliferative diseases.

Another preferred method disclosed herein is the treatment of a particular type of cancer, including cancer, squamous cell carcinoma, hematopoietic tumors of a myeloid or lymphoid lineage, mesenchymal-derived tumors, central and peripheral nervous system tumors, melanoma, seminoma, teratocarcinoma, osteosarcoma, xeroderma pigmentosum, thyroid hair follicle carcinoma and Kaposi's sarcoma.

Another preferred method disclosed herein is the treatment of a particular type of cancer, such as, but not limited to, breast cancer, lung cancer, colorectal cancer, prostate cancer, ovarian cancer, endometrial cancer, gastric cancer, clear cell renal cell carcinoma, uvea melanoma, multiple myeloma, rhabdomyosarcoma, Ewing sarcoma, Kaposi's sarcoma and medulloblastoma.

Another preferred method disclosed herein is the treatment of a particular type of cancer, such as, but not limited to, non-small cell lung cancer, neuroblastoma, colorectal cancer, anaplastic large cell lymphoma, bile duct cancer, gastric cancer, spongioblastoma, leiomyosarcoma, melanoma, squamous cell lung cancer, ovarian cancer, pancreatic cancer, prostate cancer, breast cancer, medullary thyroid carcinoma, and thyroid papillary carcinoma.

Another preferred method disclosed herein is the treatment of ALK+ anaplastic large cell lymphoma (ALCL) or other indications in which ALK activity may play a role, such as neuroblastoma, rhabdomyosarcoma, glioblastoma, inflammatory myofibroblastoma and certain types of melanoma, breast cancer, Ewing sarcoma, retinoblastoma and non-small cell lung cancer (NSCLC).

Another preferred method disclosed herein is the treatment of cell proliferative diseases such as, but not limited to, benign prostatic hyperplasia, familial adenoma, polyposis, neurofibromatosis, psoriasis, atherosclerosis and diseases associated with proliferation of vascular smooth cells and neointimal formation, such as restenosis after angioplasty or surgery, pulmonary fibrosis, arthritis, glomerular inflammation, retinopathy, including diabetic and neonatal retinopathy and age-related macular degeneration, graft vessel disease, such as can occur following vessel or organ transplantation, acromegaly and disorders secondary to acromegaly, as well as other hypertrophic conditions in which IGF/IGF-IR signalling is implicated, such as fibrotic lung disease, pathologies related to chronic or acute oxidative stress or hyperoxia induced tissue damage, and metabolic disorders in which elevated IGF levels or IGF-1R activity are implicated, such as obesity.

In addition, the method disclosed herein also provides inhibition of tumor angiogenesis and metastasis.

The present disclosure also provides a method for inhibiting active ALK protein comprising contacting the protein with an effective amount of a compound of formula (I).

It is to be understood that within the scope disclosed herein, the above various technical features and various technical features specifically described hereinafter (as in the examples) in the present disclosure may be combined with each other to constitute a new or preferred technical solution. Due to space limitations, we will not repeat them here.

As used herein, unless otherwise specified, "halogen" refers to F, Cl, Br, and I. More preferably, a halogen atom is selected from the group consisting of F, Cl and Br.

As used herein, unless otherwise specified, "deuterated" means that one or more hydrogens in a compound or group are substituted by deuterium; the "deuterated" may be mono-substituted, di-substituted, poly-substituted or fully-substituted by deuterium. The terms "substituted with one or more deuteriums" and "substituted one or more times by deuterium" are used interchangeably.

As used herein, unless otherwise specified, "non-deuterated compound" refers to a compound containing deuterium in a ratio that is not higher than the natural content of deuterium isotope (0.015%).

Also disclosed herein are isotopically labeled compounds (also referred to as "isotopic variants") to the extent of the original compounds disclosed herein. Examples of isotopes that can be listed in compounds disclosed herein include hydrogen, carbon, nitrogen, oxygen, phosphorus, sulfur, fluorine, and chlorine isotopes, such as $^2H$, $^3H$, $^{13}C$, $^{14}C$, $^{15}N$, $^{17}O$, $^{18}O$, $^{31}P$, $^{32}P$, $^{35}S$, $^{18}F$, and $^{36}Cl$, respectively. A compound of formula (I) disclosed herein containing the above isotope or other isotopic atom, or a polymorph, a pharmaceutically acceptable salt, a prodrug, a stereoisomer, an isotopic variant, a hydrate or a solvate thereof are all within the scope disclosed herein. Certain isotopically labeled compounds disclosed herein, such as the radioisotopes of $^3H$ and $^{14}C$, are also among them and are useful in the tissue distribution experiments of drugs and substrates. Tritium, i.e., $^3H$, and carbon-14, i.e., $^{14}C$, are easier to prepare and detect and are the first choice for isotopes. In addition, substitution with heavier isotopes such as deuterium, i.e., $^2H$, has advantages in some therapies due to its good metabolic stability, for example, increased half-life in vivo or reduced dosage, and thus priority may be given in some cases. Isotopically-labeled compounds can be prepared using the schemes shown in the Examples by conventional methods by replacing the non-isotopic reagents with readily available isotopically labeled reagents.

The compound of formula (I) disclosed herein may exist in the form of an acid addition salt, a base addition salt or zwitterion. The salt of the compound is prepared during isolation of the compound or after purification of the compound. The acid addition salt of a compound is that derived from the reaction of the compound with an acid. For example, the present disclosure includes acetate, adipate, alginate, bicarbonate, citrate, aspartate, benzoate, besylate, bisulfate, butyrate, camphorate, camphorsulfonate, digluconate, formate, fumarate, glycerol phosphate, glutamate, hemisulphate, heptanoate, hexanoate, hydrochloride, hydrobromide, hydroiodide, lactobionate, lactate, maleate, mesitylene sulfonate, methanesulfonate, naphthalene sulfonate, nicotinate, oxalate, pamoate, pectinic acid salt, persulfate, phosphate, picrate, propionate, succinate, tartrate, thiocyanate, trichloroacetate, p-toluenesulfonate and undecanoate of the compound and a prodrug thereof. The base addition salt of a compound is that derived from the reaction of the compound with hydroxide, carbonate or bicarbonate of a cation such as lithium, sodium, potassium, calcium, magnesium and the like.

The compound disclosed herein may include one or more asymmetric centers, and thus may exist in a variety of "stereoisomer" forms, for example, enantiomeric and/or diastereomeric forms. For example, the compound disclosed herein may be in the form of an individual enantiomer, a diastereomer or a geometric isomer (e.g., cis and trans isomers), or may be in the form of a mixture of stereoisomers, including a racemic mixture and a mixture enrich in one or more stereoisomers. The isomers can be separated from the mixture by methods known to those skilled in the art, including: chiral high pressure liquid chromatography (HPLC) and formation and crystallization of a chiral salt; or preferred isomers can be prepared by asymmetric synthesis.

In certain instances, the compound disclosed herein may also exist in the form of a tautomer. Although only one type of non-localized resonant structure may be described, it is contemplated that all such forms fall within the scope disclosed herein. For example, for purine, pyrimidine, imidazole, guanidine, amidine, and tetrazole systems, enamine tautomers may be present, and all their possible tautomeric forms fall within the scope disclosed herein.

The term "prodrug" refers to a compound that is converted in vivo to its active form with a medical effect by, for example, hydrolysis in blood. A prodrug is any covalently bonded carrier which, when administered to a patient, releases the compound disclosed herein in vivo. A prodrug is typically prepared by modifying a functional group of a drug that cleaves the prodrug in vivo to yield the parent compound. A prodrug includes, for example, a compound disclosed herein wherein a hydroxy, amino or mercapto group is bonded to any group which, when administered to a patient, can be cleaved to form a hydroxy, amino or mercapto group. Thus, representative examples of prodrugs include, but are not limited to, covalent derivatives of compounds of the present disclosure formed by the hydroxyl, amino or mercapto functional groups thereof with acetic acid, formic acid or benzoic acid. Further, in the case of a carboxylic acid (—COOH), an ester such as a methyl ester, an ethyl ester or the like may be used. The ester itself may be active and/or may be hydrolyzed in vivo under human body conditions. Suitable pharmaceutically acceptable in vivo hydrolysable esters include those which readily decompose in a human body to release a parent acid or its salt.

The term "solvate" refers to a complex in which a compound disclosed herein coordinates with a solvent molecule in a particular ratio. "Hydrate" refers to a complex formed by coordination of a compound disclosed herein with water.

Compared with the prior art, the present disclosure has the following beneficial effects: the compounds disclosed herein have excellent inhibitory properties against protein kinases such as ALK, ROS1, TRK1, TRK2, and TRK3; and the deuteration technology alters the metabolism of the compound in the organism, allowing the compound to have better pharmacokinetic parameters. In this case, the dose can be changed and a long-acting formulation can be formed to improve the applicability; the use of deuterium to replace hydrogen atoms in compounds can increase the drug concentration of the compound in animals due to its deuterium isotope effect, so as to improve the efficacy of the drug; and the replacement of hydrogen atoms in compounds with deuterium may increase the safety of the compounds due to the inhibition of certain metabolites.

DETAILED DESCRIPTION OF THE EMBODIMENTS

Compound

The present disclosure provides a compound of formula (I), or a pharmaceutically acceptable salt, a prodrug, a crystalline form, a stereoisomer, a tautomer, a hydrate or a solvate thereof:

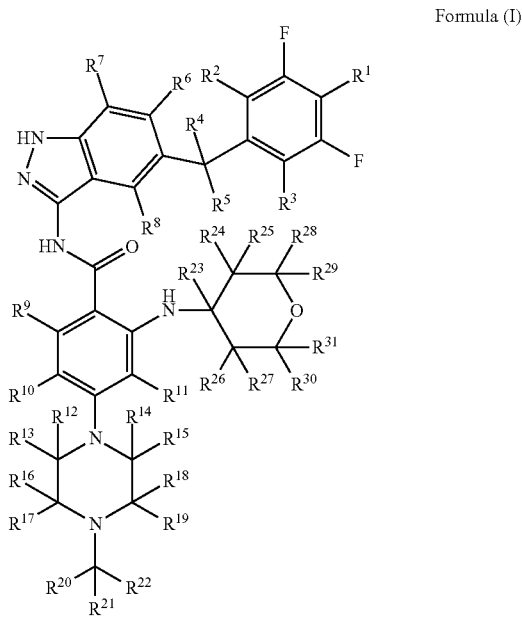

Formula (I)

wherein:
$R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$ and $R^{31}$ are each independently selected from the group consisting of hydrogen, deuterium, halogen and trifluoromethyl;

with the proviso that: at least one of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$ and $R^{31}$ is deuterated or deuterium.

As a preferred embodiment disclosed herein, the content of deuterium isotope in each deuterated position is at least greater than the natural content of deuterium isotope (0.015%), preferably greater than 30%, more preferably greater than 50%, more preferably greater than 75%, more preferably greater than 95%, and more preferably greater than 99%.

In a specific embodiment, "$R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$ and $R^{31}$ are each independently selected from the group consisting of hydrogen, deuterium, halogen and trifluoromethyl" includes: $R^1$ is selected from the group consisting of hydrogen, deuterium, halogen and trifluoromethyl, $R^2$ is selected from the group consisting of hydrogen, deuterium, halogen and trifluoromethyl, $R^3$ is selected from the group consisting of hydrogen, deuterium, halogen and trifluoromethyl, and so on, until $R^{31}$ is selected from the group consisting of hydrogen, deuterium, halogen and trifluoromethyl. More specifically, the following technical solutions are included: $R^1$ is hydrogen, $R^1$ is deuterium, $R^1$ is halogen (F, Cl, Br or I) or $R^1$ is trifluoromethyl, $R^2$ is hydrogen, $R^2$ is deuterium, $R^2$ is halogen (F, Cl, Br or I) or $R^2$ is trifluoromethyl, $R^3$ is hydrogen, $R^3$ is deuterium, $R^3$ is halogen (F, Cl, Br or I) or $R^3$ is trifluoromethyl, and so on, until $R^{31}$ is hydrogen, $R^{31}$ is deuterium, $R^{31}$ is halogen (F, Cl, Br or I) or $R^{31}$ is trifluoromethyl.

In a preferred embodiment, the present disclosure relates to a compound of formula (I), wherein $R^6$-$R^8$ are hydrogen, $R^1$-$R^5$ and $R^9$-$R^{31}$ are each independently selected from the group consisting of hydrogen and deuterium, with the proviso that the compound contains at least one deuterium atom.

In a preferred embodiment, the present disclosure relates to a compound of formula (I), wherein $R^2$-$R^3$, $R^6$-$R^9$, and $R^{23}$-$R^{27}$ are hydrogen, $R^1$, $R^4$-$R^5$, $R^{10}$-$R^{22}$, and $R^{28}$-$R^{31}$ are each independently selected from the group consisting of hydrogen and deuterium, with the proviso that the compound contains at least one deuterium atom.

In a preferred embodiment, $R^4$ and $R^5$ are the same.
In a preferred embodiment, $R^{10}$ and $R^{11}$ are the same.
In a preferred embodiment, $R^{12}$-$R^{19}$ are the same.
In a preferred embodiment, $R^{20}$-$R^{22}$ are the same.
In a preferred embodiment, $R^{28}$-$R^{31}$ are the same.

In a preferred embodiment, the present disclosure relates to a compound of formula (I), wherein $R^2$-$R^3$, $R^6$-$R^9$, and $R^{23}$-$R^{27}$ are hydrogen, $R^{10}$ and $R^{11}$ are deuterium, $R^1$, $R^4$-$R^5$, $R^{12}$-$R^{22}$, and $R^{28}$-$R^{31}$ are each independently selected from the group consisting of hydrogen and deuterium. In another specific embodiment, $R^1$ is hydrogen; in another specific embodiment, $R^1$ is deuterium; in another specific embodiment, $R^4$-$R^5$ are hydrogen; in another specific embodiment, $R^4$-$R^5$ are deuterium; in another specific embodiment, $R^{12}$-$R^{19}$ are hydrogen; in another specific embodiment, $R^{12}$-$R^{19}$ are deuterium; in another specific embodiment, $R^{20}$-$R^{22}$ are hydrogen; in another specific embodiment, $R^{20}$-$R^{22}$ are deuterium; in another specific embodiment, $R^{28}$-$R^{31}$ are hydrogen; and in another specific embodiment, $R^2$-$R^{31}$ are deuterium.

In a preferred embodiment, the present disclosure relates to a compound of formula (I), wherein $R^2$-$R^3$, $R^6$-$R^9$, and $R^{23}$-$R^{27}$ are hydrogen, $R^{12}$-$R^{19}$ are deuterium, $R^1$, $R^4$-$R^5$, $R^{10}$-$R^{11}$, $R^{20}$-$R^{22}$, and $R^{28}$-$R^{31}$ are each independently selected from the group consisting of hydrogen and deuterium. In another specific embodiment, $R^1$ is hydrogen; in another specific embodiment, $R^1$ is deuterium; in another specific embodiment, $R^4$-$R^5$ are hydrogen; in another specific embodiment, $R^4$-$R^5$ are deuterium; in another specific embodiment, $R^{10}$-$R^{11}$ are hydrogen; in another specific embodiment, $R^{10}$-$R^{11}$ are deuterium; in another specific embodiment, $R^{20}$-$R^{22}$ are hydrogen; in another specific embodiment, $R^{20}$-$R^{22}$ are deuterium; in another specific embodiment, $R^{28}$-$R^{31}$ are hydrogen; in another specific embodiment, $R^{28}$-$R^{31}$ are deuterium.

In a preferred embodiment, the present disclosure relates to a compound of formula (I), wherein $R^2$-$R^3$, $R^6$-$R^9$, and $R^{23}$-$R^{27}$ are hydrogen, $R^{20}$-$R^{22}$ are deuterium, $R^1$, $R^4$-$R^5$, $R^{10}$-$R^{11}$, $R^{12}$-$R^{19}$, and $R^{28}$-$R^{31}$ are each independently selected from the group consisting of hydrogen and deuterium. In another specific embodiment, $R^1$ is hydrogen; in another specific embodiment, $R^1$ is deuterium; in another specific embodiment, $R^4$-$R^5$ are hydrogen; in another specific embodiment, $R^4$-$R^5$ are deuterium; in another specific embodiment, $R^{10}$-$R^{11}$ are hydrogen; in another specific embodiment, $R^{10}$-$R^{11}$ are deuterium; in another specific embodiment, $R^{12}$-$R^{19}$ are hydrogen; in another specific embodiment, $R^{12}$-$R^{19}$ are deuterium; in another specific embodiment, $R^{28}$-$R^{31}$ are hydrogen; and in a specific embodiment, $R^{28}$-$R^{31}$ are deuterium.

In a preferred embodiment, the compound disclosed herein is selected from the group consisting of compounds of the formulae:

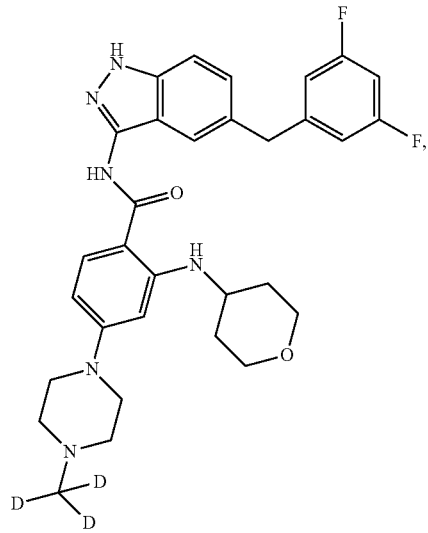

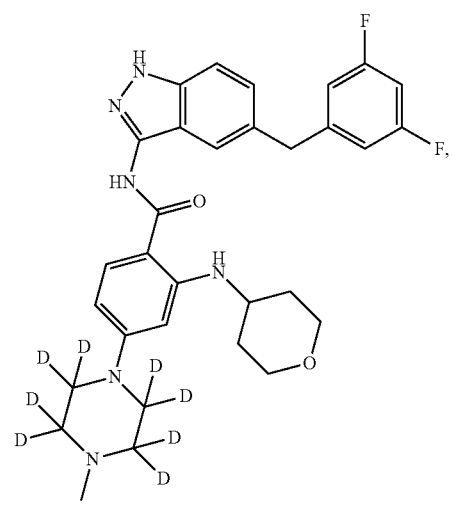

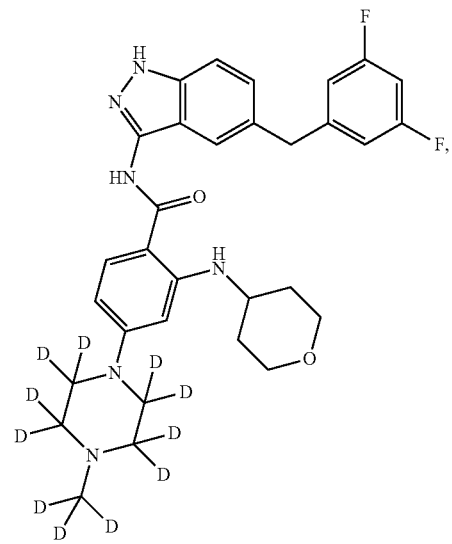

31
-continued
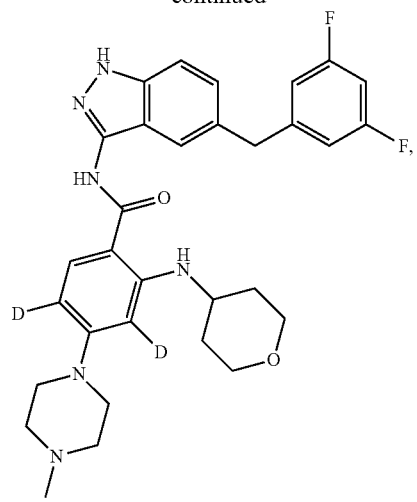
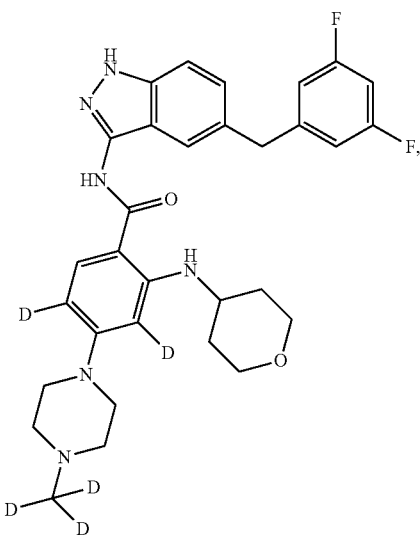
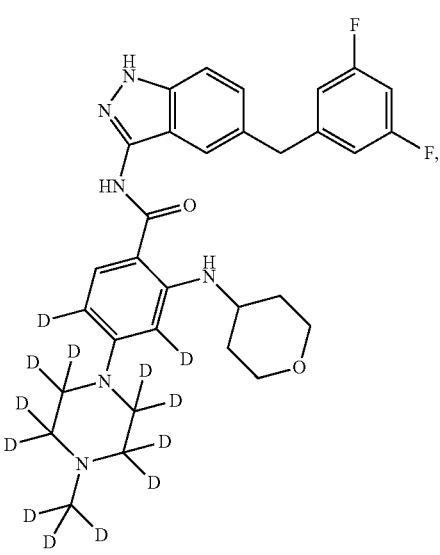
32
-continued
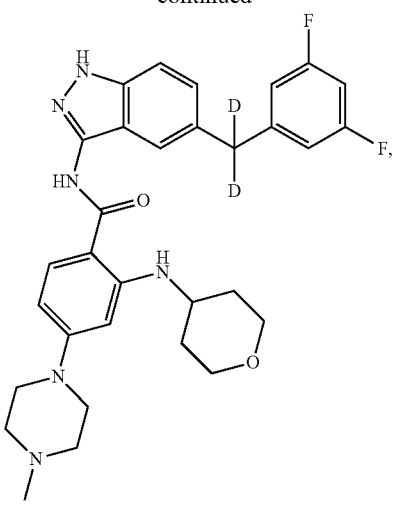
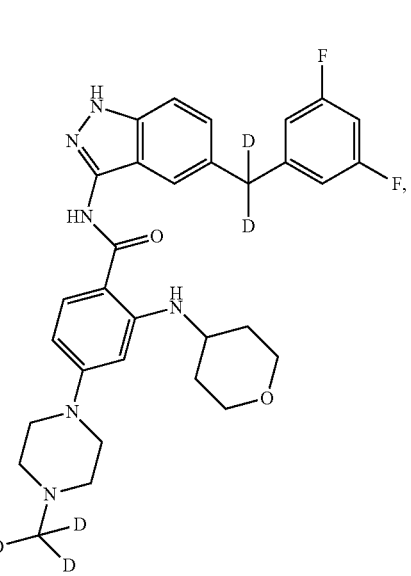
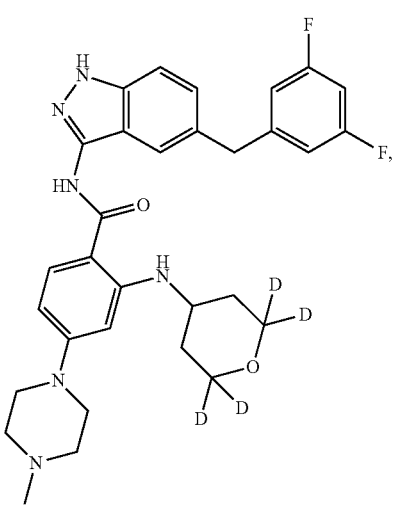

-continued

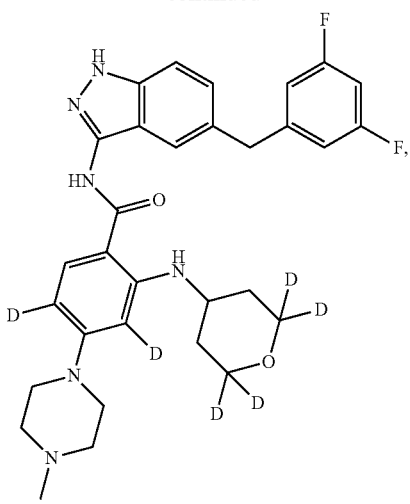

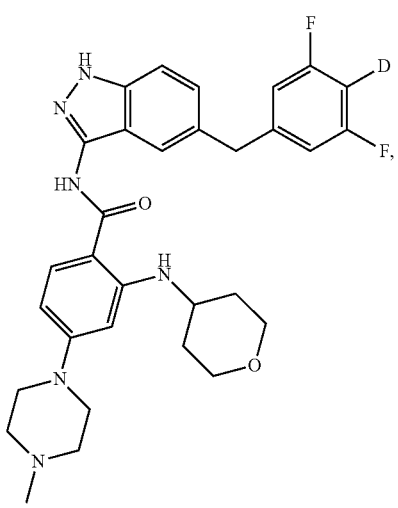

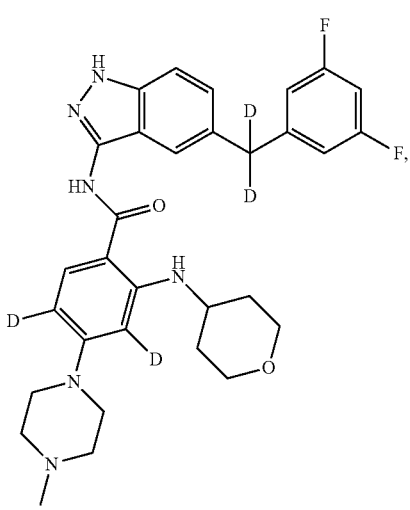

-continued

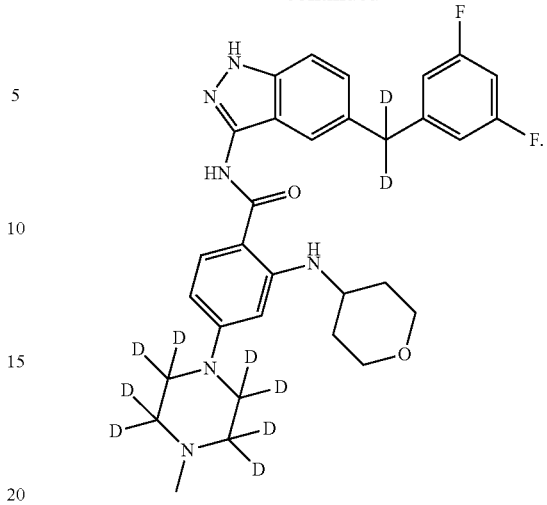

The compounds disclosed herein may include one or more asymmetric centers, and thus may exist in a variety of stereoisomeric forms, for example, enantiomeric and/or diastereomeric forms. For example, the compounds disclosed herein may be in the form of individual enantiomers, diastereomers or geometric isomers (e.g., cis and trans isomers), or may be in the form of a mixture of stereoisomers, including a racemic mixture and a mixture enrich in one or more stereoisomers. An isomer can be separated from a mixture by a method known to those skilled in the art, including: chiral high pressure liquid chromatography (HPLC) and formation and crystallization of a chiral salt; or a preferred isomer can be prepared by asymmetric synthesis.

Those skilled in the art will appreciate that an organic compound can form a complex with a solvent in which it reacts in the solvent or precipitates or crystallizes from the solvent. These complexes are referred to as "solvates". When the solvent is water, the complex is referred to as a "hydrate". The present disclosure encompasses all solvates of the compounds disclosed herein.

The term "solvate" refers to a form of a compound or a salt thereof which is combined with a solvent and usually formed by a solvolysis reaction. This physical association may include hydrogen bonding. Conventional solvents include water, methanol, ethanol, acetic acid, DMSO, THF, diethyl ether, etc. The compounds described herein can be prepared, for example, in a crystalline form, and can be solvated. Suitable solvates include pharmaceutically acceptable solvates and further include stoichiometric solvates and non-stoichiometric solvates. In some cases, the solvate will be capable of being isolated, for example, when one or more solvent molecules are incorporated into a crystal lattice of a crystalline solid. The "solvate" includes a solvate in the form of a solution and a solvate which can be separated. Representative solvates include hydrates, ethanolates, and methanolates.

The term "hydrate" refers to a compound which is associated with water. Typically, the number of the water molecules contained in a hydrate of a compound is in a definite ratio to the number of the compound molecules in the hydrate. Therefore, a hydrate of a compound may be represented, for example, by the general formula R.x $H_2O$, wherein R is the compound, and x is a number greater than 0. A given compound may form more than one type of hydrate, including, e.g., monohydrates (x is 1), lower hydrates (x is a number greater than 0 and smaller than 1, e.g., hemihydrates (R.0.5H$_2$O)), and polyhydrates (x is a number greater than 1, e.g., dihydrates (R.2H$_2$O) and hexahydrates (R.6H$_2$O)).

The compounds disclosed herein may be in amorphous or crystalline form (polymorph). Furthermore, the compounds disclosed herein may exist in one or more crystalline forms. Accordingly, the present disclosure includes within its scope all amorphous or crystalline forms of compounds disclosed herein. The term "polymorphs" refers to a crystalline form of a compound (or a salt, hydrate, or solvate thereof) in a particular crystal packing arrangement. All polymorphs have the same elemental composition. Different crystalline forms usually have different X-ray diffraction patterns, infrared spectra, melting points, density, hardness, crystal shape, optical and electrical properties, stability, and solubility. Recrystallization solvent, rate of crystallization, storage temperature, and other factors may cause one crystalline form to dominate. Various polymorphs of a compound can be prepared by crystallization under different conditions.

The present disclosure also includes isotopically labeled compounds which are equivalent to those described for formula (I), but one or more atoms are replaced by an atom having an atomic mass or mass number different from the atomic mass or mass number of an atom common in nature. Examples of isotopes which may be introduced into the compounds disclosed herein include isotopes of hydrogen, carbon, nitrogen, oxygen, phosphorus, sulfur, fluorine and chlorine, for example $^2$H, $^3$H, $^{13}$C, $^{11}$C, $^{14}$C, $^{15}$N, $^{18}$O, $^{17}$O, $^{31}$P, $^{32}$P, $^{35}$S, $^{18}$F and $^{36}$Cl, respectively. The compound disclosed herein, a prodrug thereof and a pharmaceutically acceptable salt of the compound or of the prodrug containing the above isotopes and/or other isotopes of other atoms are within the scope disclosed herein. Certain isotopically labeled compounds disclosed herein, such as those incorporating radioisotopes (e.g., $^3$H and $^{14}$C), can be used in drug and/or substrate tissue distribution assays. Tritium, i.e., $^3$H and carbon-14, i.e., $^{14}$C isotopes, are particularly preferred because they are easy to be prepared and detected. Further, substitution with heavier isotopes such as deuterium, i.e., $^2$H, can afford therapeutic advantages resulting from greater metabolic stability, for example increased in vivo half-life or reduced dosage requirements and, hence, may be preferred in some circumstances. The isotopically labelled compound of formula (I) and a prodrug thereof disclosed herein can generally be prepared by substituting a readily available isotopically labelled reagent for a non-isotopically labelled reagent when the processes disclosed in the following schemes and/or examples and preparations are carried out.

In addition, a prodrug is also included within the context disclosed herein. The term "prodrug" as used herein refers to a compound which is converted in vivo to an active form thereof having a medical effect by, for example, hydrolysis in blood. Pharmaceutically acceptable prodrugs are described in T. Higuchi and V. Stella, Prodrugs as Novel Delivery Systems, A.C.S. Symposium Series Vol. 14, Edward B. Roche, ed., Bioreversible Carriers in Drug Design, American Pharmaceutical Association and Pergamon Press, 1987, and D. Fleisher, S. Ramon, and H. Barbra "Improved oral drug delivery: solubility limitations overcome by the use of prodrugs", Advanced Drug Delivery Reviews (1996) 19(2) 115-130, each of which is incorporated herein by reference.

A prodrug is any covalently bonded compound disclosed herein which, when administered to a patient, releases the parent compound in vivo. A prodrug is typically prepared by modifying a functional group in such a way that the modification can be cleaved by routine manipulation or in vivo to yield the parent compound. A prodrug includes, for example, a compound disclosed herein wherein a hydroxy, amino or mercapto group is bonded to any group which, when administered to a patient, can be cleaved to form a hydroxy, amino or mercapto group. Thus, representative examples of prodrugs include, but are not limited to, acetate/acetamide, formate/formamide and benzoate/benzamide derivatives of hydroxyl, mercapto and amino functional groups of compounds of formula (I). In addition, in the case of a carboxylic acid (—COOH), an ester such as a methyl ester, an ethyl ester or the like may be used. The ester itself may be active and/or may be hydrolyzed under human body conditions. Suitable pharmaceutically acceptable in vivo hydrolysable ester groups include those groups which readily decompose in a human body to release a parent acid or a salt thereof.

Synthesis

The compounds disclosed herein, including their salts, can be prepared using known organic synthetic techniques and can be synthesized according to any of various possible synthetic routes, such as those in the schemes below. The reaction for preparing compounds disclosed herein can be carried out in a suitable solvent, which can be easily selected by those skilled in the art of organic synthesis. Suitable solvents can be substantially unreactive with starting materials (reactants), intermediates or products at the temperature at which the reaction is carried out (for example, at temperatures ranging from the freezing temperature to boiling temperature of a solvent). A given reaction can be carried out in one solvent or a mixture of more than one solvents. The skilled person can select the solvent for the particular reaction step depending on the particular reaction step.

The preparation of the compounds disclosed herein may involve protection and deprotection of different chemical groups. One skilled in the art can readily determine the need for protection and deprotection and the choice of appropriate protecting groups. The chemical properties of protecting groups can be found, for example, in Wuts and Greene, Protective Groups in Organic Synthesis, 4th Ed., John Wiley & Sons: New Jersey, (2006), which is incorporated herein by reference in its entirety.

The reaction can be monitored according to any suitable method known in the art. For example, product formation can be monitored by spectroscopic means (such as nuclear magnetic resonance (NMR) spectroscopy (e.g., $^1$H or $^{13}$C), infrared (IR) spectroscopy, spectrophotometry (e.g., UV-visible), mass spectrometry (MS)) or by chromatographic methods (such as high performance liquid chromatography (HPLC) or thin layer chromatography (TLC)).

Pharmaceutical Compositions, Formulations and Kits

In another aspect, provided herein is a pharmaceutical composition comprising the compound disclosed herein (also referred to as "active component") and a pharmaceutically acceptable excipient. In some embodiments, the pharmaceutical composition comprises an effective amount of the active component. In some embodiments, the pharmaceutical composition comprises a therapeutically effective amount of the active component. In some embodiments, the pharmaceutical composition comprises a prophylactically effective amount of the active component.

A pharmaceutically acceptable excipient for use in the present disclosure refers to a non-toxic carrier, adjuvant or vehicle that does not destroy the pharmacological activity of the compound formulated together. Pharmaceutically acceptable carriers, adjuvants, or vehicles that can be used in the compositions disclosed herein include, but are not limited to, ion exchangers, alumina, aluminum stearate, lecithin, serum proteins (e.g., human serum albumin), buffer substances (such as phosphate), glycine, sorbic acid, potassium sorbate, a mixture of partial glycerides of saturated plant fatty acids, water, salt or electrolyte (such as protamine sulfate), disodium hydrogen phosphate, potassium hydrogen phosphate, sodium chloride, zinc salt, silica gel, magnesium trisilicate, polyvinyl pyrrolidone, cellulose-based substances, polyethylene glycol, sodium carboxymethyl cellulose, polyacrylate, wax, polyethylene-polyoxypropylene block polymer, polyethylene glycol and lanolin.

The present disclosure also includes a kit (e.g., pharmaceutical packs). The kit provided may include compounds disclosed herein, other therapeutic agents, and first and second containers containing the compounds disclosed herein and other therapeutic agents (e.g., vials, ampoules, bottles, syringes, and/or dispersible packages or other suitable containers). In some embodiments, the kit provided can also optionally include a third container containing a pharmaceutically acceptable excipient for diluting or suspending compounds disclosed herein and/or other therapeutic agents. In some embodiments, the compounds disclosed herein and other therapeutic agents provided in a first container and a second container are combined to form a unit dosage form.

The pharmaceutical composition provided herein can be administered by a variety of routes including, but not limited to, oral administration, parenteral administration, inhalation administration, topical administration, rectal administration, nasal administration, buccal cavity administration, vaginal administration, administration by implant or other means of administration. For example, the parenteral administration as used herein includes subcutaneous administration, intradermal administration, intravenous administration, intramuscular administration, intra-articular administration, intra-arterial administration, intrasynovial administration, intrasternal administration, intracerebroventricular administration, intralesional administration, and intracranial injection or infusion techniques.

Generally, the compounds provided herein are administered in an effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

When used to prevent the condition disclosed herein, the compounds provided herein will be administered to a subject at risk for developing the condition, typically on the advice and under the supervision of a physician, at the dosage levels described above. Subjects at risk for developing a particular condition generally include those that have a family history of the condition, or those who have been identified by genetic testing or screening to be particularly susceptible to developing the condition.

The pharmaceutical compositions provided herein can also be administered chronically ("chronic administration"). Chronic administration refers to administration of a compound or pharmaceutical composition thereof over an extended period of time, e.g., for example, over 3 months, 6 months, 1 year, 2 years, 3 years, 5 years, etc, or may be continued indefinitely, for example, for the rest of the subject's life. In some embodiments, the chronic administration is intended to provide a constant level of the compound in the blood, e.g., within the therapeutic window over the extended period of time.

The pharmaceutical compostions disclosed herein may be further delivered using a variety of dosing methods. For example, In some embodiments, the pharmaceutical composition may be given as a bolus, e.g., in order to rapidly raise the concentration of the compound in the blood to an effective level. The placement of the bolus dose depends on the systemic levels of the active ingredient desired, e.g., an intramuscular or subcutaneous bolus dose allows a slow release of the active ingredient, while a bolus delivered directly to the veins (e.g., through an IV drip) allows a much faster delivery which quickly raises the concentration of the active ingredient in the blood to an effective level. In other embodiments, the pharmaceutical composition may be administered as a continuous infusion, e.g., by IV drip, to provide maintenance of a steady-state concentration of the active ingredient in the subject's body. Furthermore, in still yet other embodiments, the pharmaceutical composition may be administered as first as a bolus dose, followed by continuous infusion.

The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules or the like in the case of solid compositions. In such compositions, the compound is usually a minor component (from about 0.1% to about 50% by weight or preferably from about 1% to about 40% by weight) with the remainder being various vehicles or excipients and processing aids helpful for forming the desired dosing form.

With oral dosing, one to five and especially two to four and typically three oral doses per day are representative regimens. Using these dosing patterns, each dose provides from about 0.01 mg/kg to about 20 mg/kg of the compound disclosed herein, with preferred doses each providing from about 0.1 mg/kg to about 10 mg/kg, and especially about 1 mg/kg to about 5 mg/kg.

Transdermal doses are generally selected to provide similar or lower blood levels than are achieved using injection doses, generally in an amount ranging from about 0.01% to about 20% by weight, preferably from about 0.1% to about 20% by weight, preferably from about 0.1% to about 10% by weight, and more preferably from about 0.5% to about 15% by weight.

Injection dose levels range from about 0.1 mg/kg/hour to at least 10 mg/kg/hour, all for from about 1 to about 120 hours and especially 24 to 96 hours. A preloading bolus of from about 0.1 mg/kg to about 10 mg/kg or more may also be administered to achieve adequate steady state levels. The maximum total dose is not expected to exceed about 2 g/day for a 40 to 80 kg human patient.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable excipients known in the art. As mentioned before, the active compound in such compositions is typically a minor component, often being from about 0.05% to 10% by weight with the remainder being the injectable excipient and the like.

Transdermal compositions are typically formulated as a topical ointment or cream containing the active ingredient(s). When formulated as an ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the stable dermal penetration of the active ingredients or formulation. All such known transdermal formulations and ingredients are included within the scope provided herein.

The compounds disclosed herein can also be administered by a transdermal device. Accordingly, transdermal administration can be accomplished using a reservoir or a patch in porous membrane type or with various solid matrixes.

The above-described components for orally administrable, injectable or topically administrable compositions are merely representative. Other materials as well as processing techniques and the like are set forth in Part 8 of Remington's Pharmaceutical Sciences, 17th edition, 1985, Mack Publishing Company, Easton, Pa., which is incorporated herein by reference.

The compounds disclosed herein can also be administered in sustained release forms or from sustained release drug delivery systems. A description of representative sustained release materials can be found in Remington's Pharmaceutical Sciences.

The present disclosure also relates to the pharmaceutically acceptable formulations of a compound disclosed herein. In one embodiment, the formulation comprises water. In another embodiment, the formulation comprises a cyclodextrin derivative. The most common cyclodextrins are α-, β- and γ-cyclodextrins consisting of 6, 7 and 8 α-1,4-linked glucose units, respectively, optionally comprising one or more substituents on the linked sugar moieties, which include, but are not limited to, methylated, hydroxyalkylated, acylated, and sulfoalkylether substitution. In some embodiments, the cyclodextrin is a sulfoalkyl ether 3-cyclodextrin, e.g., for example, sulfobutyl ether O-cyclodextrin, also known as Captisol. See, e.g., U.S. Pat. No. 5,376,645. In some embodiments, the formulation comprises hexapropyl-β-cyclodextrin (e.g., 10-50% in water).

Indication

The compounds disclosed herein are useful for treating a cancer caused by deregulation of human or non-human protein kinases. In a specific embodiment, the protein kinase is selected from the group consisting of ALK, ROS1, TRK1, TRK2, and TRK3.

The compounds disclosed herein are inhibitors of at least one mutants of ALK, ROS1, TRK1, TRK2, and TRK3 and thus are suitable for treating one or more conditions associated with the activity of one or more mutants of ALK, ROS1, TRK1, TRK2, and TRK3 (e.g., deletion mutation, activating mutation, resistance mutation or a combination thereof; specific examples include L1196M, V513M, F598L, G595R, G667C, G667A, G667S, V619M, F633L, G639R, G709C, G709A, G709S, V603M, F617L, G623R, G696C, G696A, and G696S). Thus, in a particular embodiment, the present disclosure provides a method of treating a condition mediated by mutated ALK, ROS1, TRK1, TRK2, and TRK3, comprising a step of administering a compound disclosed herein, or a pharmaceutically acceptable salt, a stereoisomer, a solvate, a hydrate, a crystalline form, a prodrug, or an isotope derivative, or administering a pharmaceutical composition disclosed herein to a patient in need thereof.

The compounds disclosed herein will be, but are not limited to, administered to a patient with an effective amount of a compound or composition disclosed herein to prevent or treat a proliferative disease in a patient. Such diseases include cancer, especially non-small cell lung cancer, neuroblastoma, colorectal cancer, anaplastic large cell lymphoma, bile duct cancer, gastric cancer, glioblastoma, leiomyosarcoma, melanoma, squamous cell lung cancer, ovarian cancer, pancreatic cancer, prostate cancer, breast cancer, medullary thyroid carcinoma, and thyroid papillary carcinoma.

In addition to being useful for human therapy, the compounds disclosed herein are also useful in veterinary treatment of pets, introduced species of animals, and farm animals, including mammals, rodents, and the like. Other examples of animals include horses, dogs, and cats. Herein, the compounds disclosed herein include pharmaceutically acceptable derivatives thereof.

EXAMPLES

The preparation method of the compound of formula (I) disclosed herein is more specifically described below, but these specific methods do not constitute any limitation to the present disclosure. Optionally, the compounds disclosed herein may also be conveniently prepared by combining various synthetic methods described in the specification or known methods in the art, and such combinations can be readily made by those skilled in the art to which the present disclosure pertains.

Synthetic Method

Usually, in the preparation process, each reaction is usually carried out in an inert solvent at a temperature from room temperature to reflux temperature (e.g., 0° C. to 100° C., preferably 0° C. to 80° C.). The reaction time is usually from 0.1 to 60 hours, preferably from 0.5 to 24 hours.

The abbreviations used herein have the following meanings:

| | |
|---|---|
| APCI | atmospheric pressure chemical ionization |
| Boc$_2$O | di-tert-butyl dicarbonate |
| Tol | toluene |
| DMAP | 4-dimethylaminopyridine |
| DCM | dichloromethane |
| TsOMe | methyl p-toluenesulfonate |
| DMF | N,N-dimethylformamide |
| TFA | trifluoroacetic acid |
| TFAA | trifluoroacetic anhydride |
| TEA | triethylamine |
| DIPEA | N,N-diisopropylethylamine |
| THF | tetrahydrofuran |
| TMSBr | trimethylsilyl bromide |
| TsCl | p-toluenesulfonyl chloride |
| DMSO | dimethyl sulfoxide |

Example 1: Preparation of N-(5-(3,5-difluorobenzyl)-1H-indazol-3-yl)-4-(4-(methyl-d₃)piperazin-1-yl)-2-((tetrahydro-2H-pyran-4-yl)amino)benzamide, Compound T-1, with the Formula
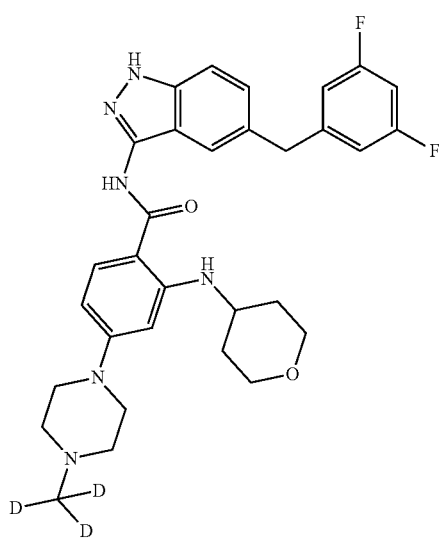
T-1
The following route is used for synthesis:
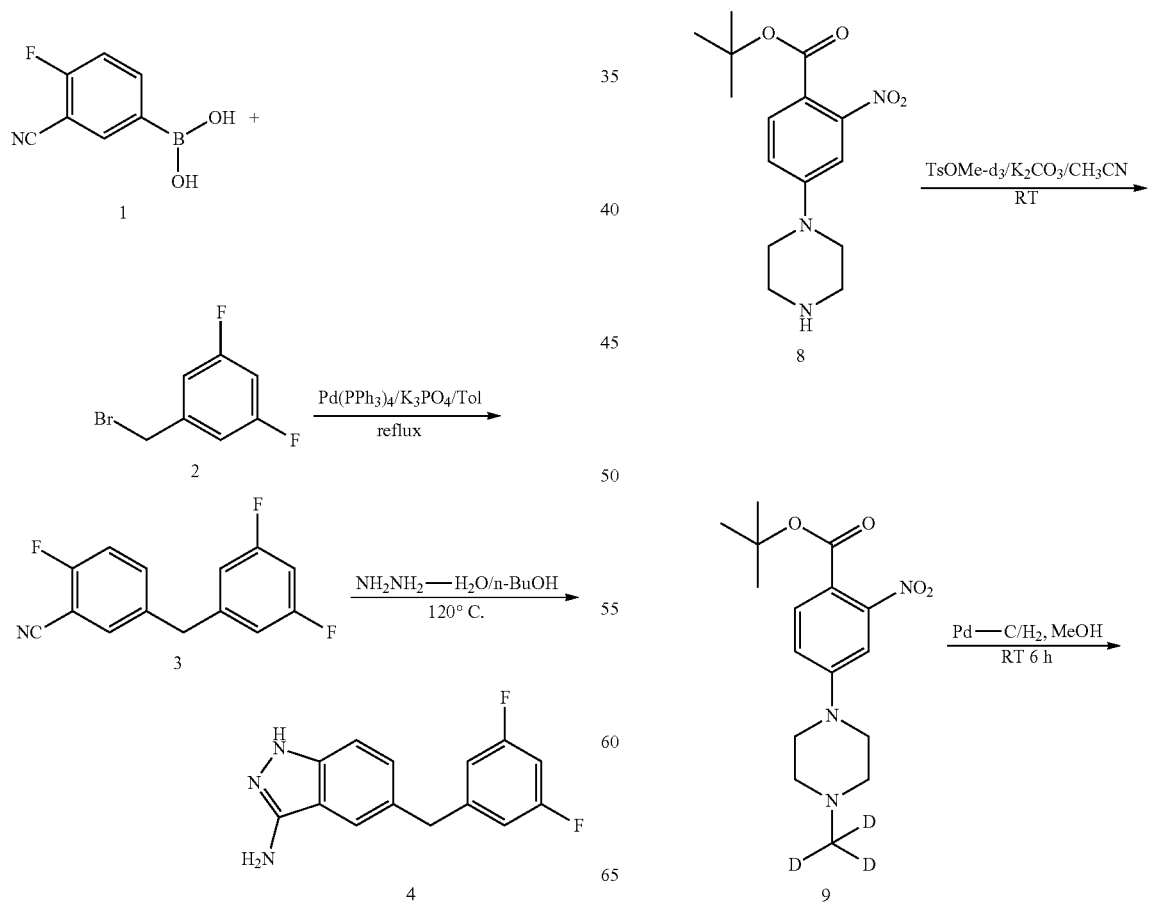
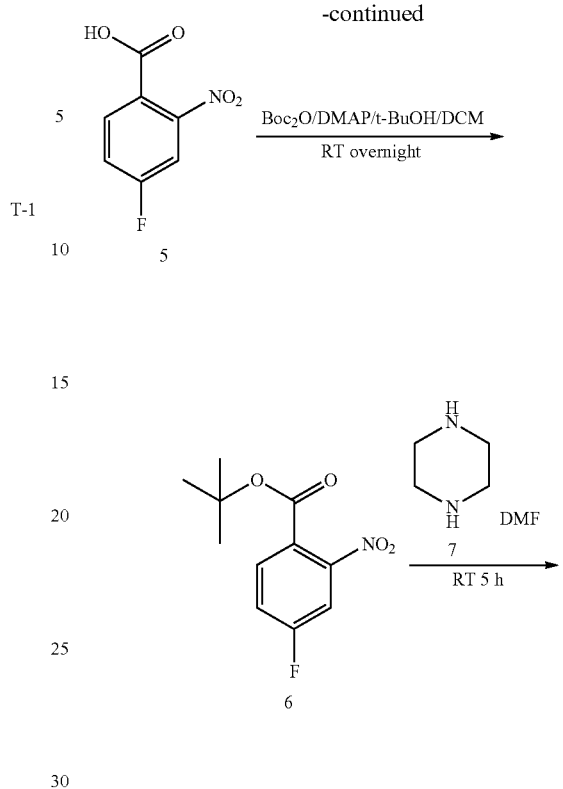

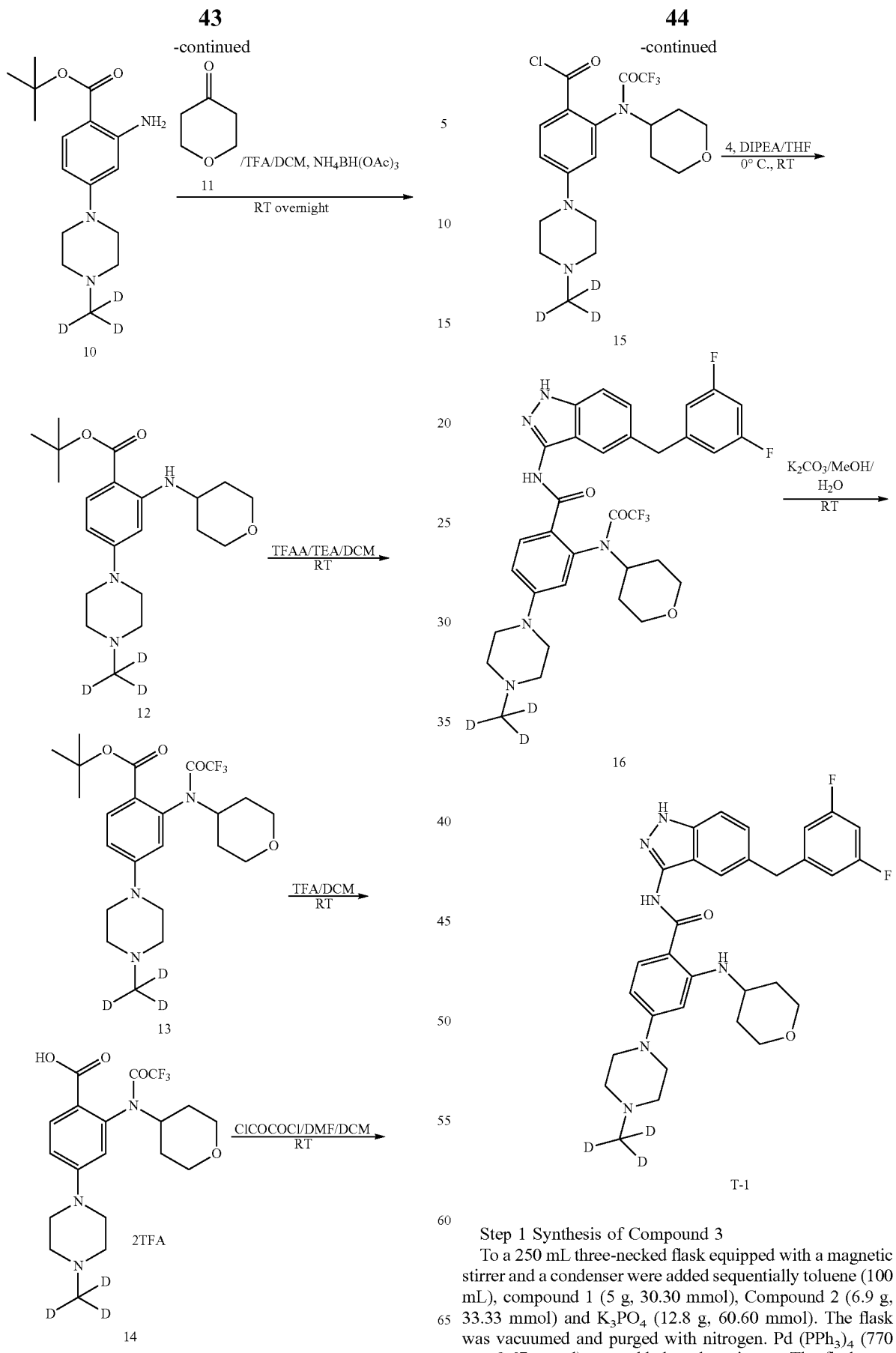
Step 1 Synthesis of Compound 3
To a 250 mL three-necked flask equipped with a magnetic stirrer and a condenser were added sequentially toluene (100 mL), compound 1 (5 g, 30.30 mmol), Compound 2 (6.9 g, 33.33 mmol) and $K_3PO_4$ (12.8 g, 60.60 mmol). The flask was vacuumed and purged with nitrogen. Pd $(PPh_3)_4$ (770 mg, 0.67 mmol) was added to the mixture. The flask was vacuumed again and purged with nitrogen for three times. The mixture was heated to 110° C., and reacted for 5 h with stirring at the temperature. After cooling to room temperature, ethyl acetate (200 mL) was added to the mixture, and the resulting solid was filtered. The filtrate was concentrated. The residue was passed through a silica gel column to afford 5.4 g of a white solid in a yield of 72.2%. $^1$H NMR (400 MHz, CDCl$_3$) δ 7.43-7.39 (m, 2H), 7.18 (t, J=8.8 Hz, 1H), 6.73-6.66 (m, 3H), 3.96 (s, 2H).

Step 2 Synthesis of Compound 4

To a 100 mL single-necked flask equipped with a magnetic stirrer and a condenser were added sequentially n-butanol (550 mL), compound 3 (5.4 g, 21.86 mmol) and hydrazine hydrate (5.47 g, 109.3 mmol). The mixture was heated to 120° C., and reacted overnight with stirring at the temperature. After cooling to room temperature, the reaction solution was concentrated. The residue was passed through a silica gel column to afford 3.4 g of a white solid in a yield of 60.1%. LC-MS (APCI): m/z=260.1 (M+1)$^+$. $^1$H NMR (400 MHz, CDCl$_3$) δ 11.32 (s, 1H), 7.53 (s, 1H), 7.18-7.11 (m, 2H), 7.05-7.00 (m, 1H), 6.95-6.92 (m, 2H), 5.25 (br s, 2H), 4.00 (s, 2H).

Step 3 Synthesis of Compound 6

To a solution of 4-fluoro-2-nitrobenzoic acid (10 g, 54 mmol) in dichloromethane (200 mL) under magnetic stirring were added sequentially Boc$_2$O (23.6 g, 108 mmol) and DMAP (2 g, 16.3 mmol). The reaction was stirred at room temperature for 30 minutes, and then tert-butanol (40 g, 540 mmol) was added. The mixture was stirred and reacted at room temperature overnight. 100 mL of water was added to the mixture, and the mixture was extracted with dichloromethane (100 mL×3). The organic phase was washed with 1M HCl (40 mL) and then saturated brine (40 mL), dried over anhydrous sodium sulfate, and filtered. The filtrate was concentrated to afford 7 g of a white solid in a yield of 53.7%. LC-MS (APCI): m/z=242.1 (M+1)$^+$.

Step 4 Synthesis of Compound 8

To a solution of compound 6 (2 g, 8.3 mmol) in DMF (10 mL) under magnetic stirring was added piperazine (928 mg, 10.8 mmol). The mixture was stirred at room temperature overnight. To the mixture was added 50 mL of water. The mixture was stirred for 20 minutes, and a large amount of solid was precipitated. The solid was filtered, washed with water (20 mL) and dried to afford 1.9 g of a yellow solid in a yield of 74.5%. LC-MS (APCI): m/z=208.1 (M+1−100)$^+$, 308.1 (M+1)$^+$.

Step 5 Synthesis of Compound 9

To a solution of compound 8 (1.9 g, 6.19 mmol) in acetonitrile (10 mL) under magnetic stirring were added sequentially TsOMe-d$_3$ (1.75 g, 9.28 mmol) and K$_2$CO$_3$ (2.56 g, 18.6 mmol). The mixture was stirred and reacted at room temperature overnight. The acetonitrile was evaporated under reduced pressure. To the residue were added water (20 mL) and ethyl acetate (30 mL). The organic layer was separated and the aqueous layer was extracted with ethyl acetate (30 mL×2). The organic phases were combined, dried over anhydrous sodium sulfate, filtered and concentrated. The residue was passed through a silica gel column to afford 1.6 g of a yellow solid, in a yield of 79.8%. LC-MS (APCI): m/z=225.1 (M+1−100)$^+$, 325.1 (M+1)$^+$. $^1$H NMR (400 MHz, CDCl$_3$) δ 7.71 (d, J=8.8 Hz, 1H), 6.99 (d, J=2.4 Hz, 1H), 6.94 (dd, J=8.8 Hz, J=2.4 Hz, 1H), 3.35 (t, J=4.2 Hz, 4H), 2.54 (t, J=4.2 Hz, 4H), 1.51 (s, 9H).

Step 6 Synthesis of Compound 10

To a solution of compound 9 (1.6 g, 4.94 mmol) in methanol (20 mL) under magnetic stirring was added Pd—C (160 mg, 10% wt). The container was vacuumed and purged with hydrogen for three times. The reaction was stirred at room temperature under a hydrogen balloon overnight. The catalyst was filtered off, and washed with anhydrous methanol (10 mL). The filtrate was concentrated to afford 1.4 g of a colorless oil in a yield of 96.3%. LC-MS (APCI): m/z=195.1 (M+1−100)$^+$, 295.1 (M+1)$^+$.

Step 7 Synthesis of Compound 12

To a solution of compound 10 (1.4 g, 4.76 mmol) in dichloromethane (20 mL) under magnetic stirring were added sequentially compound 11 (571 mg, 5.71 mmol) and trifluoroacetic acid (1 mL). The reaction was stirred under nitrogen atmosphere at room temperature for 1.5 hours, and then tetramethylammonium Triacetoxyborohydride (1.88 g, 7.14 mmol) was added. The reaction was stirred at room temperature overnight. To the mixture was added water (20 mL), and the organic layer was separated. The aqueous phase was extracted with dichloromethane (20 mL×2), dried over anhydrous sodium sulfate and filtered. The filtrate was concentrated. The residue was passed through a silica gel column to afford 1.4 g of a colorless oil in a yield of 77.7%. LC-MS (APCI): m/z=279.1 (M+1−100)$^+$, 379.1 (M+1)$^+$. $^1$H NMR (400 MHz, CDCl$_3$) δ 7.91 (d, J=7.0 Hz, 1H), 7.75 (d, J=9.0 Hz, 1H), 6.15 (dd, J=9.0 Hz, J=3.0 Hz, 1H), 6.02 (d, J=3.0 Hz, 1H), 4.02-3.98 (m, 2H), 3.59-3.54 (m, 3H), 3.29 (t, J=5.0 Hz, 4H), 2.54 (t, J=5.0 Hz, 4H), 2.06-2.03 (m, 2H), 1.68-1.61 (m, 2H), 1.55 (sa, 9H).

Step 8 Synthesis of Compound 13

To a solution of compound 12 (1.4 g, 3.7 mmol) in dichloromethane (20 mL) under magnetic stirring was added triethylamine (0.85 mL, 5.92 mmol) at 0° C. TFAA (1.4 mL, 4.81 mmol) was added slowly dropwise, and the reaction was stirred at room temperature for 4 h. Water (20 mL) was added, and the organic layer was separated. The aqueous phase was extracted with dichloromethane (20 mL×2), dried over anhydrous sodium sulfate and filtered. The filtrate was concentrated. The residue was passed through a silica gel column to afford 1.0 g of a colorless oil in a yield of 57.0%. LC-MS (APCI): m/z=375.1 (M+1−100)$^+$, 475.1 (M+1)$^+$.

Step 9 Synthesis of Compound 14

To a solution of compound 13 (1.0 g, 2.11 mmol) in dichloromethane (10 mL) under magnetic stirring was added trifluoroacetic acid (3 mL) at 0° C. The reaction was stirred at room temperature under nitrogen atmosphere overnight. The solvent and the trifluoroacetic acid were evaporated under reduced pressure. To the residue was added diethyl ether (20 mL). The mixture was stirred for 20 minutes, and a large amount of a white solid was precipitated. The solid was filtered, washed with diethyl ether, and dried to afford 940 mg of a white solid in a yield of 83.8%. LC-MS (APCI): m/z=419.2 (M+1)$^+$.

Step 10 Synthesis of Compound 16

Under nitrogen atmosphere and at 0° C., to a solution of compound 14 (940 mg, 1.77 mmol) in anhydrous dichloromethane (10 mL) under magnetic stirring was added anhydrous DMF (3 drops) and then added slowly oxalyl chloride (4.4 mL, 8.8 mmol, 2 M solution in dichloromethane) dropwise. The reaction was stirred at room temperature under nitrogen atmosphere for 3 hours. Under reduced pressure, the solvent and excess oxalyl chloride were evaporated and co-evaporated twice with anhydrous dichloromethane. The residue was dissolved in anhydrous THF (3 mL) and ready for use. Compound 4 (219 mg, 0.85 mmol) and anhydrous tetrahydrofuran (5 mL) were added to another 50 mL two-necked flask, which were dissolved with stirring. DIPEA (437 mg, 3.38 mmol) was added under nitrogen atmosphere, and cooled to 0° C. To the mixture was added slowly the above solution of acyl chloride dropwise. After the dropwise addition, the ice bath was removed, and the reaction was stirred at room temperature overnight. The solvent was evaporated under reduced pressure. The residue was passed through a silica gel column to afford 0.66 g of a white solid in a yield of 56.5%. LC-MS (APCI): m/z=660.3 (M+1)$^+$.

Step 11 Synthesis of Compound T-1

To a solution of 16 (0.66 g, 1.0 mmol) in methanol/water (11 mL, 10/1) under magnetic stirring was added potassium carbonate (0.42 g, 3.0 mmol). The reaction was stirred at room temperature under nitrogen atmosphere for 3 hours. To the mixture was added water (30 mL), and a large amount of a grey solid was precipitated. The solid was filtered, washed with water (10 mL), dissolved in dichloromethane (20 mL), dried and concentrated. The residue was passed through a silica gel column to afford 0.4 g of a white solid in a yield of 71.0%. LC-MS (APCI): m/z=564.2 (M+1)$^+$. $^1$H NMR (400 MHz, CDCl$_3$) δ 8.52 (s, 1H), 8.14 (d, J=8.0 Hz, 1H), 7.76 (s, 1H), 7.56 (d, J=8.8 Hz, 1H), 7.31 (d, J=8.8 Hz, 1H), 7.16 (dd, J=8.8 Hz, J=2.0 Hz, 1H), 6.72-6.69 (m, 2H), 6.64-6.59 (m, 1H), 6.23 (dd, J=8.8 Hz, J=2.0 Hz, 1H), 6.10 (s, 1H), 4.05 (s, 2H), 4.01-3.95 (m, 2H), 3.60-3.52 (m, 3H), 3.35 (t, J=4.8 Hz, 4H), 2.62 (t, J=4.8 Hz, 4H), 2.05-2.01 (m, 2H).

Example 2: Preparation of N-(5-(3,5-difluorobenzyl)-1H-indazol-3-yl)-4-(4-methylpiperazin-1-yl-2,2,3,3,5,5,6,6-d$_8$)-2-((tetrahydro-2H-pyran-4-yl)amino)benzamide, Compound T-2, with the Formula

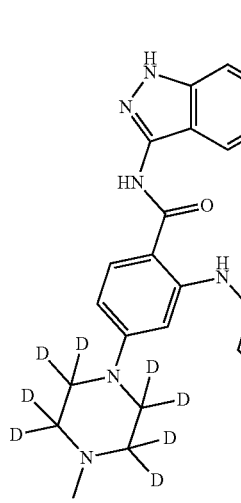

T-2

The following route is used for synthesis:

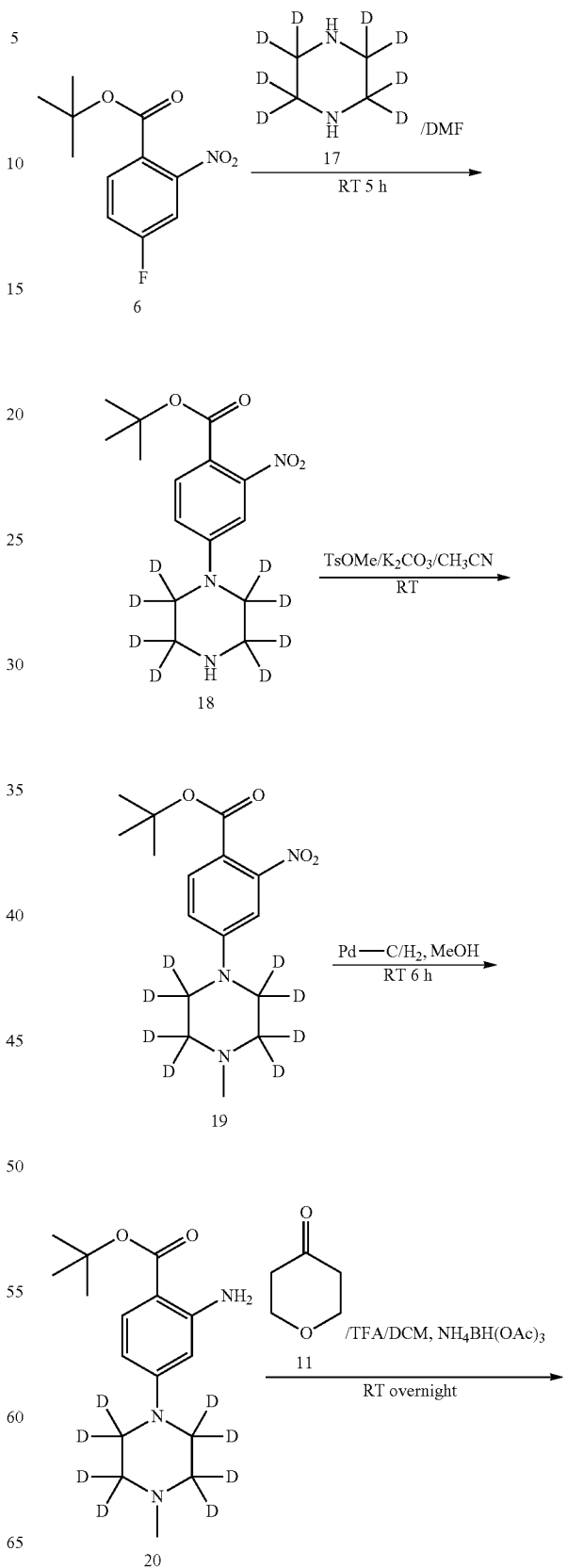

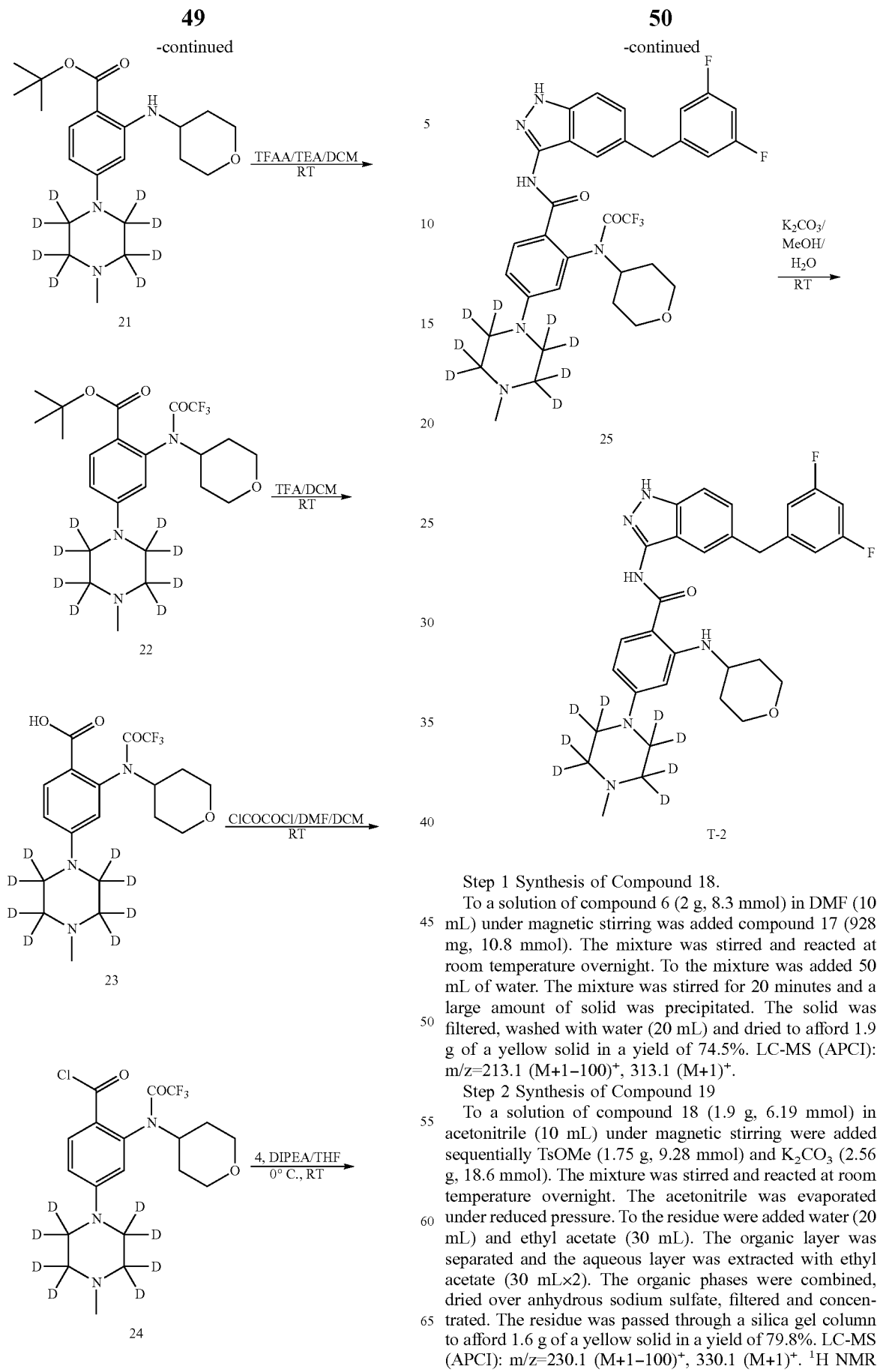

Step 1 Synthesis of Compound 18.

To a solution of compound 6 (2 g, 8.3 mmol) in DMF (10 mL) under magnetic stirring was added compound 17 (928 mg, 10.8 mmol). The mixture was stirred and reacted at room temperature overnight. To the mixture was added 50 mL of water. The mixture was stirred for 20 minutes and a large amount of solid was precipitated. The solid was filtered, washed with water (20 mL) and dried to afford 1.9 g of a yellow solid in a yield of 74.5%. LC-MS (APCI): m/z=213.1 (M+1−100)$^+$, 313.1 (M+1)$^+$.

Step 2 Synthesis of Compound 19

To a solution of compound 18 (1.9 g, 6.19 mmol) in acetonitrile (10 mL) under magnetic stirring were added sequentially TsOMe (1.75 g, 9.28 mmol) and K$_2$CO$_3$ (2.56 g, 18.6 mmol). The mixture was stirred and reacted at room temperature overnight. The acetonitrile was evaporated under reduced pressure. To the residue were added water (20 mL) and ethyl acetate (30 mL). The organic layer was separated and the aqueous layer was extracted with ethyl acetate (30 mL×2). The organic phases were combined, dried over anhydrous sodium sulfate, filtered and concentrated. The residue was passed through a silica gel column to afford 1.6 g of a yellow solid in a yield of 79.8%. LC-MS (APCI): m/z=230.1 (M+1−100)$^+$, 330.1 (M+1)$^+$. $^1$H NMR (400 MHz, CDCl$_3$) δ 7.71 (d, J=8.8 Hz, 1H), 6.99 (d, J=2.4 Hz, 1H), 6.94 (dd, J=8.8 Hz, J=2.4 Hz, 1H), 2.35 (s, 3H), 1.51 (s, 9H).

Step 3 Synthesis of Compound 20

To a solution of compound 19 (1.6 g, 4.94 mmol) in methanol (20 mL) under magnetic stirring was added Pd—C (160 mg, 10% wt). The container was vacuumed and purged with hydrogen for three times. The reaction was stirred at room temperature under a hydrogen balloon overnight. The catalyst was filtered off, and washed with anhydrous methanol (10 mL). The filtrate was concentrated to afford 1.4 g of a colorless oil in a yield of 96.3%. LC-MS (APCI): m/z=200.1 (M+1−100)$^+$, 300.1 (M+1)$^+$.

Step 4 Synthesis of Compound 21

To a solution of compound 20 (1.4 g, 4.76 mmol) in dichloromethane (20 mL) under magnetic stirring were added sequentially compound 11 (571 mg, 5.71 mmol) and trifluoroacetic acid (1 mL). The reaction was stirred at room temperature under nitrogen atmosphere for 1.5 hours, and then tetramethylammonium triacetoxyborohydride (1.88 g, 7.14 mmol) was added. The reaction was stirred at room temperature overnight. To the mixture was added water (20 mL), and the organic layer was separated. The aqueous phase was extracted with dichloromethane (20 mL×2), dried over anhydrous sodium sulfate and filtered. The filtrate was concentrated. The residue was passed through a silica gel column to afford 1.4 g of a colorless oil in a yield of 77.7%. LC-MS (APCI): m/z=284.1 (M+1−100)$^+$, 384.1 (M+1)$^+$. $^1$H NMR (500 MHz, CDCl$_3$) δ: 7.91 (d, J=7.0 Hz, 1H), 7.75 (d, J=9.0 Hz, 1H), 6.15 (dd, J=9.0 Hz, J=3.0 Hz, 1H), 6.02 (d, J=3.0 Hz, 1H), 4.02-3.98 (m, 2H), 3.59-3.54 (m, 3H), 2.35 (s, 3H), 2.06-2.03 (m, 2H), 1.68-1.61 (m, 2H), 1.55 (s, 9H).

Step 5 Synthesis of Compound 22

To a solution of compound 21 (1.4 g, 3.7 mmol) in dichloromethane (20 mL) under magnetic stirring was added triethylamine (0.85 mL, 5.92 mmol) at 0° C. To the mixture was added slowly TFAA (1.4 mL, 4.81 mmol) dropwise, and the reaction was stirred at room temperature for 4 h. To the mixture was added water (20 mL), and the organic layer was separated. The aqueous phase was extracted with dichloromethane (20 mL×2), dried over anhydrous sodium sulfate and filtered. The filtrate was concentrated. The residue was passed through a silica gel column to afford 1.0 g of a colorless oil in a yield of 57.0%. LC-MS (APCI): m/z=380.1 (M+1−100)$^+$, 480.1 (M+1)$^+$.

Step 6 Synthesis of Compound 23

To a solution of compound 22 (1.0 g, 2.11 mmol) in dichloromethane (10 mL) under magnetic stirring was added trifluoroacetic acid (3 mL) at 0° C. The reaction was stirred at room temperature under nitrogen atmosphere overnight. The solvent and the trifluoroacetic acid were evaporated under reduced pressure. To the residue was added diethyl ether (20 mL). The mixture was stirred for 20 minutes, and a large amount of a white solid was precipitated. The solid was filtered, washed with diethyl ether and dried to afford 940 mg of a white solid in a yield of 83.8%. LC-MS (APCI): m/z=424.2 (M+1)$^+$.

Step 7 Synthesis of Compound 25

Under nitrogen atmosphere and at 0° C., to a solution of compound 23 (940 mg, 1.77 mmol) in anhydrous dichloromethane (10 mL) under magnetic stirring was added anhydrous DMF (3 drops), and then added slowly oxalyl chloride (4.4 mL, 8.8 mmol, 2 M solution in dichloromethane) dropwise. The reaction was stirred at room temperature under nitrogen atmosphere for 3 hours. Under reduced pressure, the solvent and excess oxalyl chloride were evaporated and co-evaporated twice with anhydrous dichloromethane. The residue was dissolved in anhydrous THF (3 mL) and ready for use. Compound 4 (219 mg, 0.85 mmol) and anhydrous tetrahydrofuran (5 mL) were added to another 50 mL two-necked flask, and dissolved with stirring. DIPEA (437 mg, 3.38 mmol) was added under nitrogen atmosphere, and cooled to 0° C. To the mixture was added slowly the above solution of acyl chloride dropwise. After the dropwise addition, the ice bath was removed, and the reaction was stirred at room temperature overnight. The solvent was evaporated under reduced pressure. The residue was passed through a silica gel column to afford 0.66 g of a white solid in a yield of 56.5%. LC-MS (APCI): m/z=665.3 (M+1)$^+$.

Step 8 Synthesis of T-2

To a solution of compound 25 (0.66 g, 1.0 mmol) in methanol/water (11 mL, 10/1) under magnetic stirring was added potassium carbonate (0.42 g, 3.0 mmol). The reaction was stirred at room temperature under nitrogen atmosphere for 3 hours. To the mixture was added water (30 mL), and a large amount of a grey solid was precipitated. The solid was filtered, washed with water (10 mL), dissolved in dichloromethane (20 mL), dried and concentrated. The residue was passed through a silica gel column to afford 0.4 g of a white solid in a yield of 71.0%. LC-MS (APCI): m/z=569.2 (M+1)$^+$. $^1$H NMR (400 MHz, DMSO-D$_6$) δ: 12.66 (s, 1H), 10.11 (s, 1H), 8.30 (d, J=8.0 Hz, 1H), 7.80 (d, J=8.8 Hz, 1H), 7.49 (s, 1H), 7.42 (d, J=8.8 Hz, 1H), 7.26 (dd, J=8.8 Hz, J=1.6 Hz, 1H), 7.02-6.98 (m, 3H), 6.24 (dd, J=8.8 Hz, J=2.4 Hz, 1H), 6.14 (d, J=2.8 Hz, 1H), 4.05 (s, 2H), 3.84-3.80 (m, 2H), 3.73-3.68 (m, 1H), 3.50 (t, J=9.6 Hz, 2H), 2.30 (s, 3H), 1.98-1.93 (m, 2H), 1.40-1.33 (m, 2H).

Example 3: Preparation of N-(5-(3,5-difluorobenzyl)-1H-indazol-3-yl)-4-(4-(methyl-d$_3$)piperazin-1-yl-2,2,3,3,5,5,6,6-d$_8$)-2-((tetrahydro-2H-pyran-4-yl)amino)benzamide, Compound T-3, with the Formula

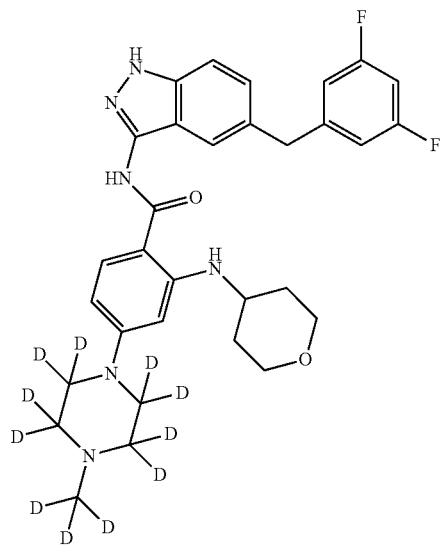

T-3

The following route is used for synthesis:
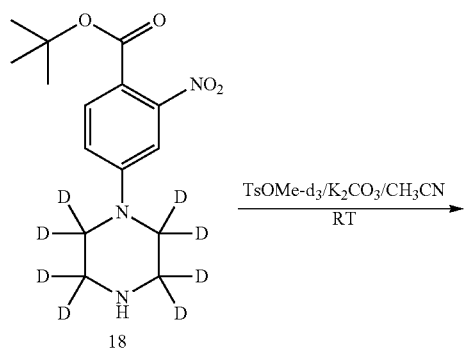
18
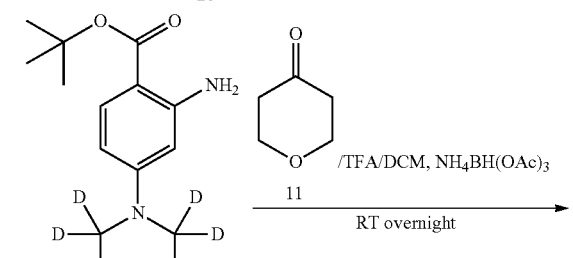
26
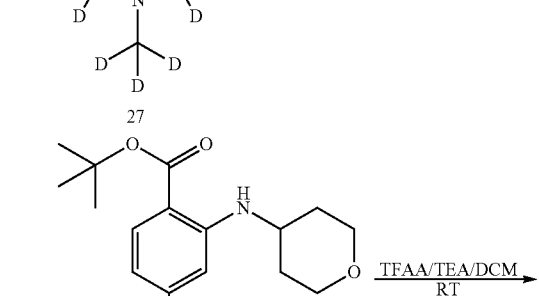
27
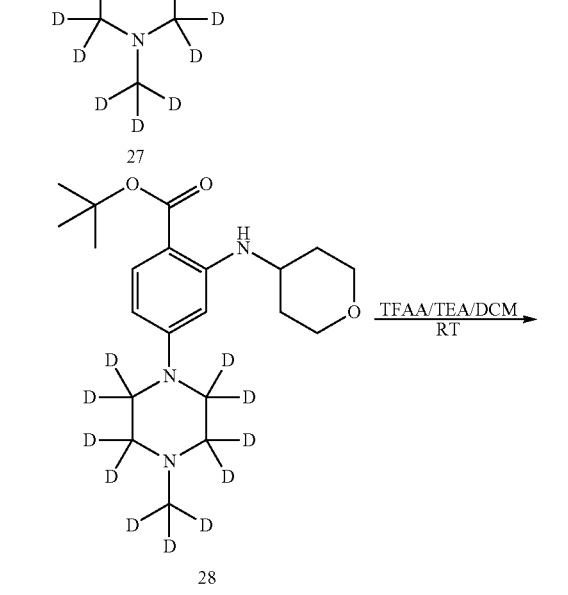
28
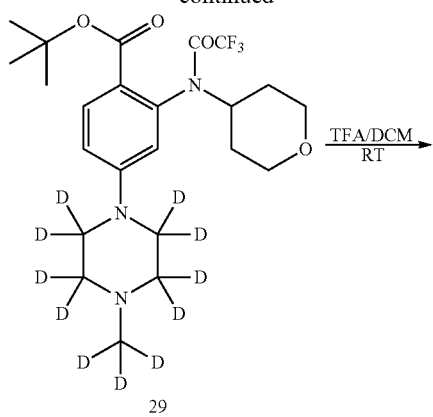
29
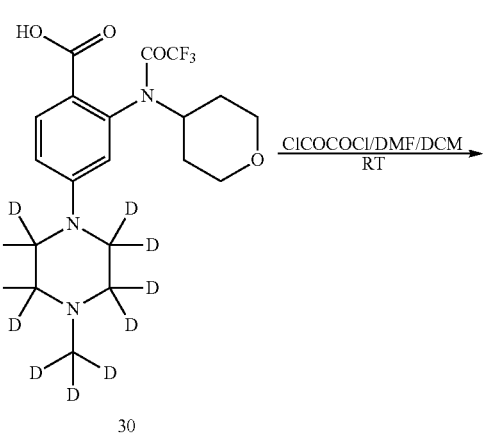
30
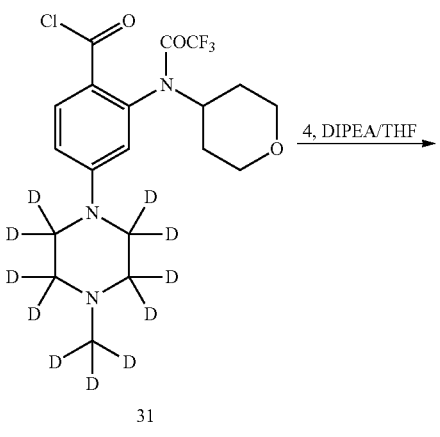
31

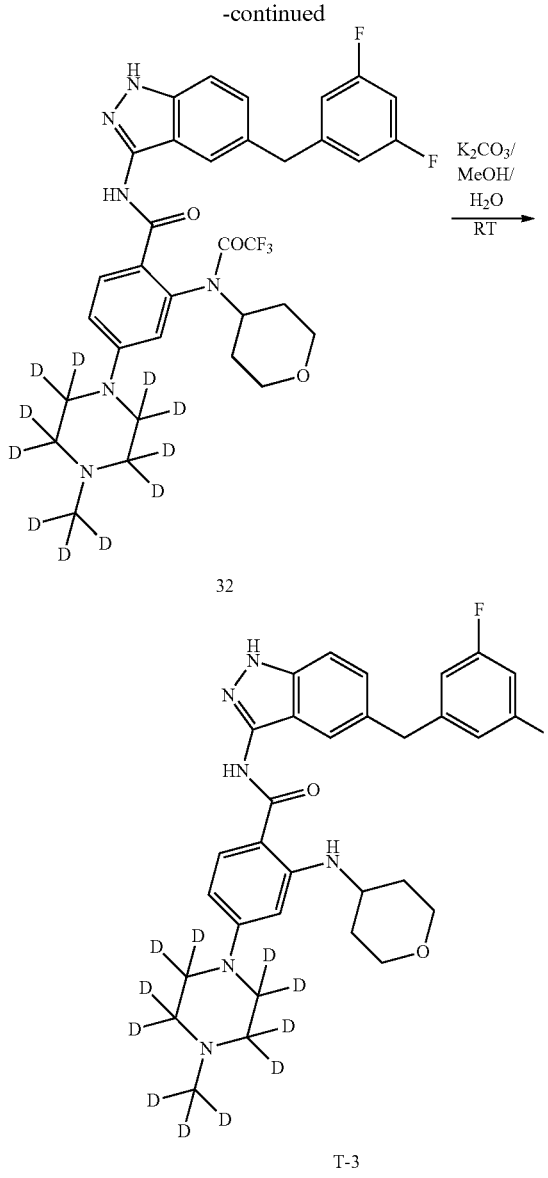

Step 1 Synthesis of Compound 26.

To a solution of compound 18 (0.85 g, 3.1 mmol) in acetonitrile (10 mL) under magnetic stirring were added sequentially TsOMe-d₃ (0.88 g, 4.62 mmol) and K₂CO₃ (1.28 g, 9.3 mmol). The mixture was stirred and reacted at room temperature overnight. The acetonitrile was evaporated under reduced pressure. To the residue were added water (20 mL) and ethyl acetate (30 mL). The organic layer was separated and the aqueous layer was extracted with ethyl acetate (30 mL×2). The organic phases were combined, dried over anhydrous sodium sulfate, filtered and concentrated. The residue was passed through a silica gel column to afford 0.8 g of a yellow solid in a yield of 79.8%. LC-MS (APCI): m/z=233.1 (M+1−100)⁺, 333.1 (M+1)⁺. ¹H NMR (400 MHz, CDCl₃) δ 7.71 (d, J=8.8 Hz, 1H), 6.99 (d, J=2.4 Hz, 1H), 6.94 (dd, J=8.8 Hz, J=2.4 Hz, 1H), 1.51 (s, 9H).

Step 2 Synthesis of Compound 27

To a solution of compound 26 (0.8 g, 2.48 mmol) in methanol (10 mL) under magnetic stirring was added Pd—C (80 mg, 10% wt). The container was vacuumed and purged with hydrogen for three times. The reaction was stirred at room temperature under a hydrogen balloon overnight. The catalyst was filtered off, and washed with anhydrous methanol (10 mL). The filtrate was concentrated to afford 0.7 g of a colorless oil in a yield of 96.3%. LC-MS (APCI): m/z=200.1 (M+1−100)⁺, 300.1 (M+1)⁺.

Step 3 Synthesis of Compound 28

To a solution of compound 27 (0.7 g, 2.88 mmol) in dichloromethane (10 mL) under magnetic stirring were added sequentially compound 11 (236 mg, 2.36 mmol) and trifluoroacetic acid (0.5 mL). The reaction was stirred under nitrogen atmosphere at room temperature for 1.5 hours, and then tetramethylammonium triacetoxyborohydride (0.94 g, 3.57 mmol) was added. The reaction was stirred at room temperature overnight. To the mixture was added water (20 mL), and the organic layer was separated. The aqueous phase was extracted with dichloromethane (20 mL×2), dried over anhydrous sodium sulfate and filtered. The filtrate was concentrated. The residue was passed through a silica gel column to afford 0.7 g of a colorless oil in a yield of 77.7%. LC-MS (APCI): m/z=287.1 (M+1−100)⁺, 387.1 (M+1)⁺. ¹H NMR (500 MHz, CDCl₃) δ 7.91 (d, J=7.0 Hz, 1H), 7.75 (d, J=9.0 Hz, 1H), 6.15 (dd, J=9.0 Hz, J=3.0 Hz, 1H), 6.02 (d, J=3.0 Hz, 1H), 4.02-3.98 (m, 2H), 3.59-3.54 (m, 3H), 2.06-2.03 (m, 2H), 1.68-1.61 (m, 2H), 1.55 (s, 9H).

Step 4 Synthesis of Compound 29

Under an ice water bath, to a solution of compound 28 (0.7 g, 1.85 mmol) in dichloromethane (10 mL) under magnetic stirring was added triethylamine (0.47 mL, 2.97 mmol), and then added slowly TFAA (0.7 mL, 2.42 mmol) dropwise. The reaction was stirred at room temperature for 4 hours. Water (20 mL) was added, and the organic layer was separated. The aqueous phase was extracted with dichloromethane (20 mL×2), dried over anhydrous sodium sulfate and filtered. The filtrate was concentrated. The residue was passed through a silica gel column to afford 0.5 g of a colorless oil in a yield of 57.0%. LC-MS (APCI): m/z=383.1 (M+1−100)⁺, 483.1 (M+1)⁺.

Step 5 Synthesis of Compound 30

To a solution of compound 29 (0.5 g, 1.06 mmol) in dichloromethane (5 mL) under magnetic stirring was added trifluoroacetic acid (1.5 mL) at 0° C. The reaction was stirred at room temperature under nitrogen atmosphere overnight. The solvent and the trifluoroacetic acid were evaporated under reduced pressure. To the residue was added diethyl ether (20 mL). The mixture was stirred for 20 minutes and a large amount of a white solid was precipitated. The solid was filtered, washed with diethyl ether and dried to afford 470 mg of a white solid in a yield of 83.8%. LC-MS (APCI): m/z=427.2 (M+1)⁺.

Step 6 Synthesis of Compound 32

Under nitrogen atmosphere and ice water bath, to a solution of compound 30 (470 mg, 0.88 mmol) in anhydrous dichloromethane (6 mL) under magnetic stirring was added anhydrous DMF (2 drops), and then added slowly oxalyl chloride (2.2 mL, 4.4 mmol, 2 M solution in dichloromethane) dropwise. The reaction was stirred at room temperature under nitrogen atmosphere for 3 hours. Under reduced pressure, the solvent and excess oxalyl chloride were evaporated and co-evaporated twice with anhydrous dichloromethane. The residue was dissolved in anhydrous THF (2 mL) and ready for use. Compound 4 (110 mg, 0.43 mmol) and anhydrous tetrahydrofuran (5 mL) were added to another 50 mL two-necked flask, and dissolved with stirring. DIPEA (220 mg, 1.70 mmol) was added under nitrogen atmosphere, and cooled in an ice water bath. To the mixture was added slowly the above solution of acyl chloride dropwise. After the dropwise addition, the ice bath was removed, and the reaction was stirred at room temperature overnight. The solvent was evaporated under reduced pressure. The residue was passed through a silica gel column to afford 0.33 g of a white solid in a yield of 56.5%. LC-MS (APCI): m/z=668.3 (M+1)$^+$.

Step 8 Synthesis of Compound T-3

To a solution of compound 32 (0.33 g, 0.5 mmol) in methanol/water (6 mL, 10/1) under magnetic stirring was added potassium carbonate (0.21 g, 1.5 mmol). The reaction was stirred at room temperature under nitrogen atmosphere for 3 hours. To the mixture was added water (30 mL), and a large amount of a grey solid was precipitated. The solid was filtered, washed with water (10 mL), dissolved in dichloromethane (20 mL), dried and concentrated. The residue was passed through a silica gel column to afford 0.2 g of a white solid in a yield of 71.0%. LC-MS (APCI): m/z=572.3 (M+1)$^+$. $^1$H NMR (400 MHz, DMSO-D$_6$) δ 12.66 (s, 1H), 10.11 (s, 1H), 8.30 (d, J=8.0 Hz, 1H), 7.80 (d, J=8.8 Hz, 1H), 7.49 (s, 1H), 7.42 (d, J=8.8 Hz, 1H), 7.26 (dd, J=8.8 Hz, J=1.6 Hz, 1H), 7.02-6.98 (m, 3H), 6.24 (dd, J=8.8 Hz, J=2.4 Hz, 1H), 6.14 (d, J=2.8 Hz, 1H), 4.05 (s, 2H), 3.84-3.80 (m, 2H), 3.73-3.68 (m, 1H), 3.50 (t, J=9.6 Hz, 2H), 1.98-1.93 (m, 2H), 1.40-1.33 (m, 2H).

Example 4: Preparation of N-(5-(3,5-difluorobenzyl)-1H-indazol-3-yl)-4-(4-methylpiperazin-1-yl)-2-((tetrahydro-2H-pyran-4-yl)amino)benzamide-3,5-d, Compound T-4, with the Formula

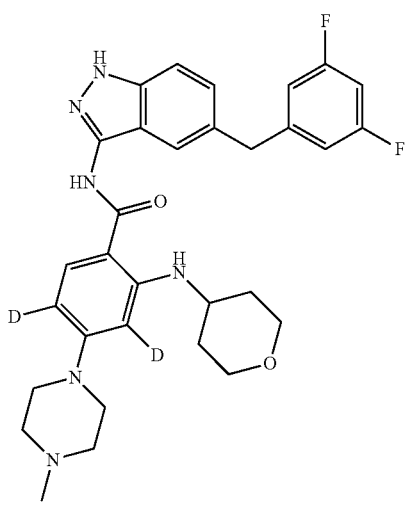

The following route is used for synthesis:

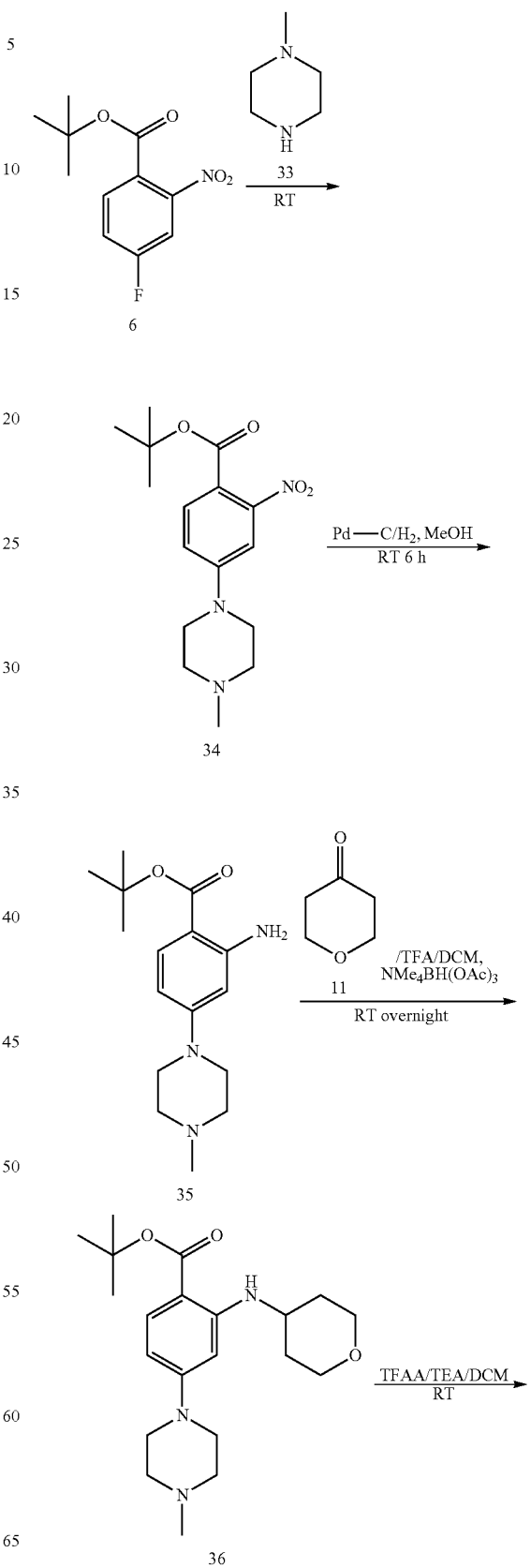

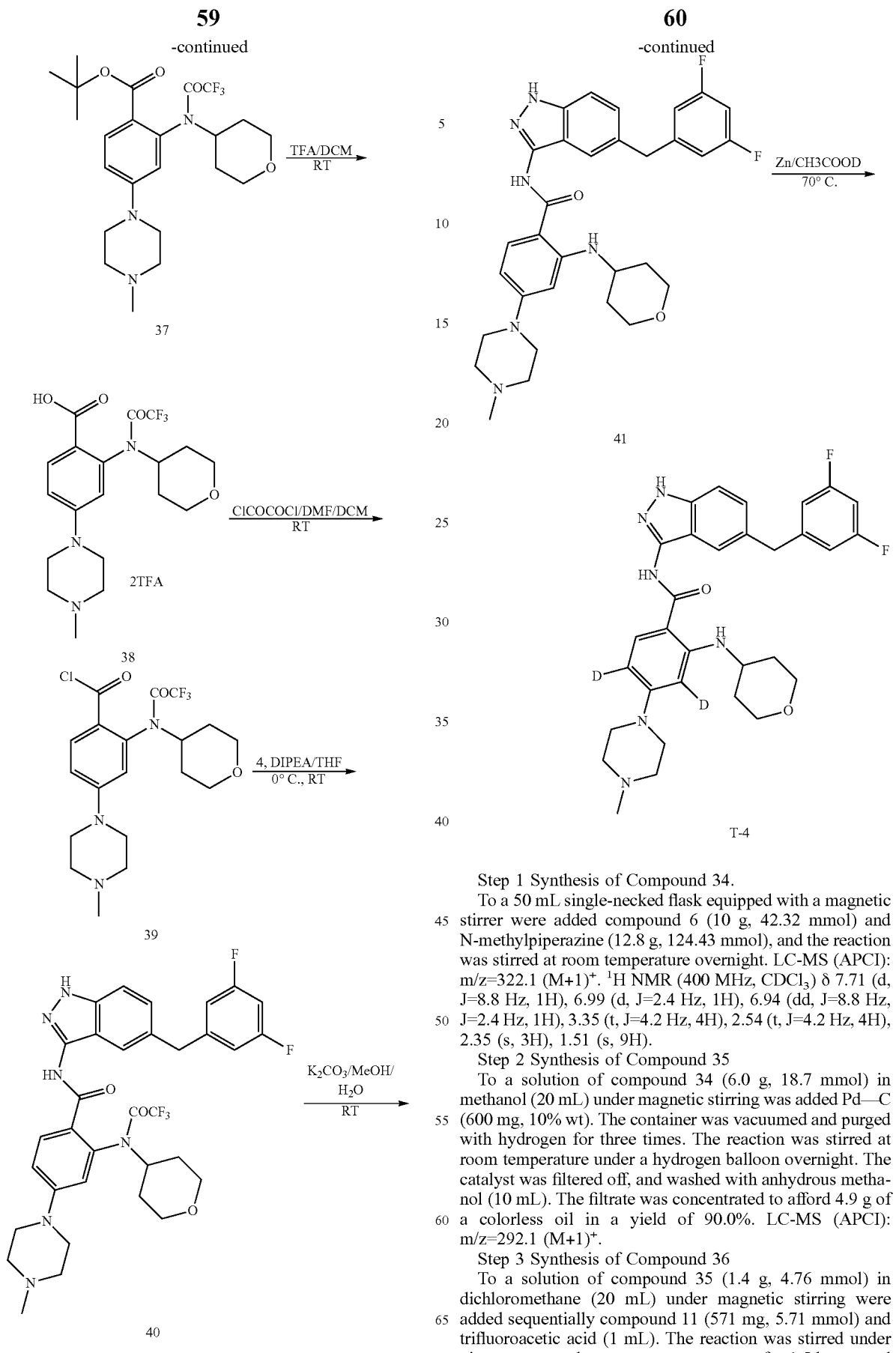

Step 1 Synthesis of Compound 34.

To a 50 mL single-necked flask equipped with a magnetic stirrer were added compound 6 (10 g, 42.32 mmol) and N-methylpiperazine (12.8 g, 124.43 mmol), and the reaction was stirred at room temperature overnight. LC-MS (APCI): m/z=322.1 (M+1)$^+$. $^1$H NMR (400 MHz, CDCl$_3$) δ 7.71 (d, J=8.8 Hz, 1H), 6.99 (d, J=2.4 Hz, 1H), 6.94 (dd, J=8.8 Hz, J=2.4 Hz, 1H), 3.35 (t, J=4.2 Hz, 4H), 2.54 (t, J=4.2 Hz, 4H), 2.35 (s, 3H), 1.51 (s, 9H).

Step 2 Synthesis of Compound 35

To a solution of compound 34 (6.0 g, 18.7 mmol) in methanol (20 mL) under magnetic stirring was added Pd—C (600 mg, 10% wt). The container was vacuumed and purged with hydrogen for three times. The reaction was stirred at room temperature under a hydrogen balloon overnight. The catalyst was filtered off, and washed with anhydrous methanol (10 mL). The filtrate was concentrated to afford 4.9 g of a colorless oil in a yield of 90.0%. LC-MS (APCI): m/z=292.1 (M+1)$^+$.

Step 3 Synthesis of Compound 36

To a solution of compound 35 (1.4 g, 4.76 mmol) in dichloromethane (20 mL) under magnetic stirring were added sequentially compound 11 (571 mg, 5.71 mmol) and trifluoroacetic acid (1 mL). The reaction was stirred under nitrogen atmosphere at room temperature for 1.5 hours, and then tetramethylammonium triacetoxyborohydride (1.88 g, 7.14 mmol) was added. The reaction was stirred at room temperature overnight. To the mixture was added water (20 mL), and the organic layer was separated. The aqueous phase was extracted with dichloromethane (20 mL×2), dried over anhydrous sodium sulfate and filtered. The filtrate was concentrated. The residue was passed through a silica gel column to afford 1.4 g of a colorless oil in a yield of 77.7%. LC-MS (APCI): m/z=376.1 (M+1)$^+$. $^1$H NMR (500 MHz, CDCl$_3$) δ 7.91 (d, J=7.0 Hz, 1H), 7.75 (d, J=9.0 Hz, 1H), 6.15 (dd, J=9.0 Hz, J=3.0 Hz, 1H), 6.02 (d, J=3.0 Hz, 1H), 4.02-3.98 (m, 2H), 3.59-3.54 (m, 3H), 3.29 (t, J=5.0 Hz, 4H), 2.54 (t, J=5.0 Hz, 4H), 2.35 (s, 3H), 2.06-2.03 (m, 2H), 1.68-1.61 (m, 2H), 1.55 (s, 9H).

Step 4 Synthesis of Compound 37

Under ice water bath, to a solution of compound 36 (1.4 g, 3.7 mmol) in dichloromethane (20 mL) under magnetic stirring was added triethylamine (0.85 mL, 5.92 mmol), and then added slowly TFAA (1.4 mL, 4.81 mmol) dropwise. The reaction was stirred at room temperature for 4 hours. To the mixture was added water (20 mL), and the organic layer was separated. The aqueous phase was extracted with dichloromethane (20 mL×2), dried over anhydrous sodium sulfate and filtered. The filtrate was concentrated. The residue was passed through a silica gel column to afford 1.0 g of a colorless oil in a yield of 57.0%. LC-MS (APCI): m/z=472.1 (M+1)$^+$.

Step 5 Synthesis of Compound 38

To a solution of compound 37 (1.0 g, 2.11 mmol) in dichloromethane (10 mL) under magnetic stirring was added trifluoroacetic acid (3 mL) at 0° C. The reaction was stirred at room temperature under nitrogen atmosphere overnight. The solvent and the trifluoroacetic acid were evaporated under reduced pressure. To the residue was added diethyl ether (20 mL). The mixture was stirred for 20 minutes, and a large amount of a white solid was precipitated. The solid was filtered, washed with diethyl ether and dried to afford 940 mg of a white solid in a yield of 83.8%. LC-MS (APCI): m/z=416.2 (M+1)$^+$.

Step 6 Synthesis of Compound 40

Under nitrogen atmosphere and at 0° C., to a solution of compound 38 (940 mg, 1.77 mmol) in anhydrous dichloromethane (10 mL) under magnetic stirring was added anhydrous DMF (3 drops) and then added slowly oxalyl chloride (4.4 mL, 8.8 mmol, 2 M solution in dichloromethane) dropwise. The reaction was stirred at room temperature under nitrogen atmosphere for 3 hours. Under reduced pressure, the solvent and excess oxalyl chloride were evaporated and co-evaporated twice with anhydrous dichloromethane. The residue was dissolved in anhydrous THF (3 mL) and ready for use. Compound 4 (219 mg, 0.85 mmol) and anhydrous tetrahydrofuran (5 mL) were added to another 50 mL two-necked flask, and dissolved with stirring. DIPEA (437 mg, 3.38 mmol) was added under nitrogen atmosphere, and cooled in ice water bath. To the mixture was added slowly the above solution of acyl chloride dropwise. After the dropwise addition, the ice bath was removed, and the reaction was stirred at room temperature overnight. The solvent was evaporated under reduced pressure. The residue was passed through a silica gel column to afford 0.66 g of a white solid in a yield of 56.5%. LC-MS (APCI): m/z=657.3 (M+1)$^+$.

Step 7 Synthesis of Compound 41

To a solution of compound 40 (0.66 g, 1.0 mmol) in methanol/water (11 mL, 10/1) under magnetic stirring was added potassium carbonate (0.42 g, 3.0 mmol). The reaction was stirred at room temperature under nitrogen atmosphere for 3 hours. To the mixture was added water (30 mL), and a large amount of a grey solid was precipitated. The solid was filtered, washed with water (10 mL), dissolved in dichloromethane (20 mL), dried and concentrated. The residue was passed through a silica gel column to afford 0.4 g of a white solid in a yield of 71.0%. LC-MS (APCI): m/z=561.2 (M+1)$^+$. $^1$H NMR (400 MHz, CDCl$_3$) δ 8.52 (s, 1H), 8.14 (d, J=8.0 Hz, 1H), 7.76 (s, 1H), 7.56 (d, J=8.8 Hz, 1H), 7.31 (d, J=8.8 Hz, 1H), 7.16 (dd, J=8.8 Hz, J=2.0 Hz, 1H), 6.72-6.69 (m, 2H), 6.64-6.59 (m, 1H), 6.23 (dd, J=8.8 Hz, J=2.0 Hz, 1H), 6.10 (s, 1H), 4.05 (s, 2H), 4.01-3.95 (m, 2H), 3.60-3.52 (m, 3H), 3.35 (t, J=4.8 Hz, 4H), 2.62 (t, J=4.8 Hz, 4H), 2.40 (s, 3H), 2.05-2.01 (m, 2H).

Step 8 Synthesis of Compound T-4

To a 50 mL single-necked flask equipped with a magnetic stirrer and a condenser were added sequentially compound 41 (112 mg, 0.2 mmol) and CH$_3$COOD (8 mL). To the mixture was added zinc powder (56 mg, 1 mmol) with stirring. The flask was vacuumed and purged with nitrogen for three times. The mixture was heated to 70° C., and reacted for 2 h with stirring at the temperature. After cooling to room temperature, ethyl acetate (20 mL) was added, and the unreacted zinc powder was filtered off. The filtrate was concentrated to dryness. To the residue was added saturated NaHCO$_3$ solution (10 mL) and the mixture was extracted with ethyl acetate (15 mL×3). The organic phases were combined, dried over anhydrous sodium sulfate, and filtered. The filtrate was concentrated. The residue was passed through a silica gel column to afford 80 mg of a white solid in a yield of 71.4%. LC-MS (APCI): m/z=563.2 (M+1)$^+$. $^1$H NMR (400 MHz, DMSO-D6) δ 12.64 (s, 1H), 10.09 (s, 1H), 8.28 (d, J=8.0 Hz, 1H), 7.79 (d, J=8.8 Hz, 1H), 7.48 (s, 1H), 7.40 (d, J=8.8 Hz, 1H), 7.25 (dd, J=8.8 Hz, J=1.6 Hz, 1H), 7.02-6.98 (m, 3H), 4.04 (s, 2H), 3.84-3.80 (m, 2H), 3.73-3.68 (m, 1H), 3.50 (t, J=9.6 Hz, 2H), 3.26 (t, J=4.8 Hz, 4H), 2.44 (t, J=4.8 Hz, 4H), 2.30 (s, 3H), 1.98-1.93 (m, 2H), 1.40-1.33 (m, 2H).

Example 5: Preparation of N-(5-(3,5-difluorobenzyl)-1H-indazol-3-yl)-4-(4-(methyl-d$_3$)piperazin-1-yl)-2-((tetrahydro-2H-pyran-4-yl)amino)benzamide-3,5-d$_2$, Compound T-5, with the Formula

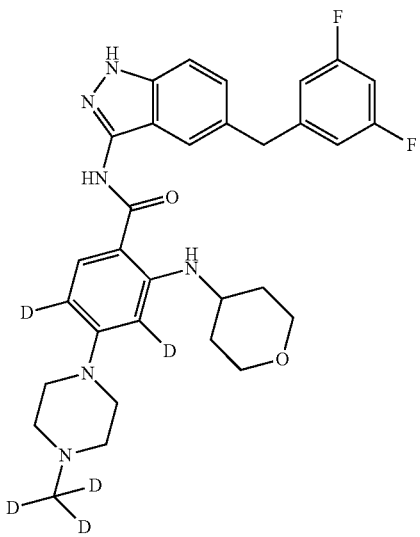

T-5

The following route is used for synthesis:

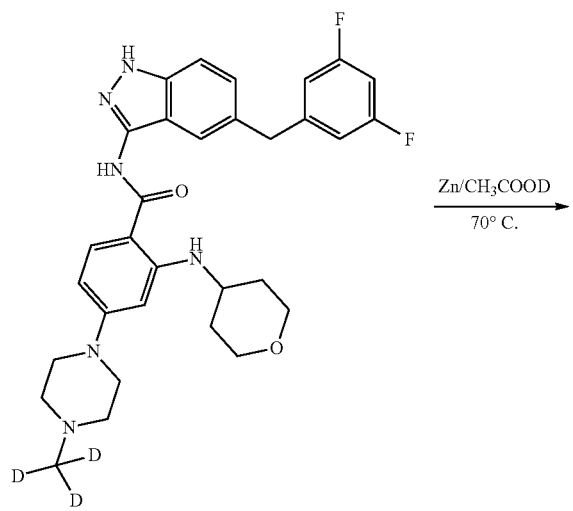

To a 50 mL single-necked flask equipped with a magnetic stirrer and a condenser was added sequentially compound T-1 (112 mg, 0.2 mmol) and CH$_3$COOD (8 mL). To the mixture was added zinc powder (56 mg, 1 mmol) with stirring. The flask was vacuumed and purged with nitrogen for three times. The mixture was heated to 70° C., and reacted for 2 h with stirring at the temperature. After cooling to room temperature, ethyl acetate (20 mL) was added, and the unreacted zinc powder was filtered off. The filtrate was concentrated to dryness. To the residue was added saturated NaHCO$_3$ solution (10 mL) and the mixture was extracted with ethyl acetate (15 mL×3). The organic phases were combined, dried over anhydrous sodium sulfate, and filtered. The filtrate was concentrated. The residue was passed through a silica gel column to afford 80 mg of a white solid in a yield of 71.4%. LC-MS (APCI): m/z=566.2 (M+1)$^+$. $^1$H NMR (400 MHz, DMSO-D6) δ 12.64 (s, 1H), 10.09 (s, 1H), 8.28 (d, J=8.0 Hz, 1H), 7.79 (d, J=8.8 Hz, 1H), 7.48 (s, 1H), 7.40 (d, J=8.8 Hz, 1H), 7.25 (dd, J=8.8 Hz, J=1.6 Hz, 1H), 7.02-6.98 (m, 3H), 4.04 (s, 2H), 3.84-3.80 (m, 2H), 3.73-3.68 (m, 1H), 3.50 (t, J=9.6 Hz, 2H), 3.26 (t, J=4.8 Hz, 4H), 2.44 (t, J=4.8 Hz, 4H), 1.98-1.93 (m, 2H), 1.40-1.33 (m, 2H).

Example 6: Preparation of N-(5-(3,5-difluorobenzyl)-1H-indazol-3-yl)-4-(4-(methyl-d$_3$)piperazin-1-yl-2,2,3,3,5,5,6,6-d$_8$)-2-((tetrahydro-2H-pyran-4-yl)amino)benzamide-3,5-d$_2$, Compound T-6, with the Formula

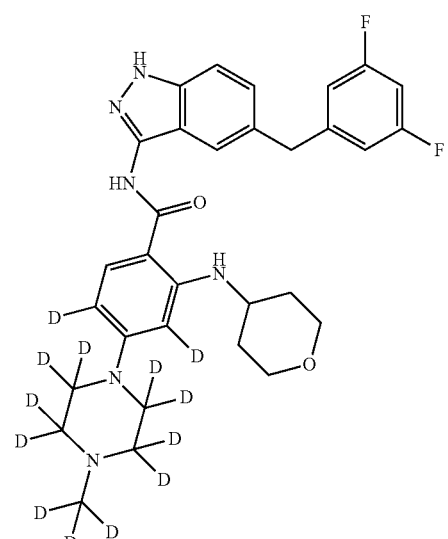

The following route is used for synthesis:

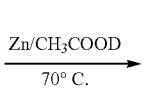

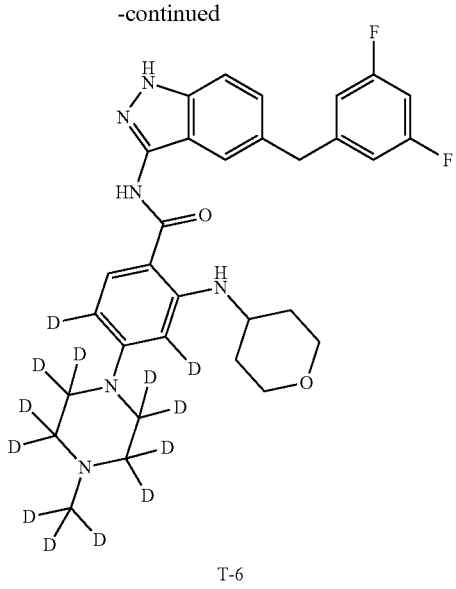

T-6

To a 50 mL single-necked flask equipped with a magnetic stirrer and a condenser were added sequentially compound T-3 (112 mg, 0.2 mmol) and CH₃COOD (8 mL). To the mixture was added zinc powder (56 mg, 1 mmol) with stirring. The flask was vacuumed and purged with nitrogen for three times. The mixture was heated to 70° C., and reacted for 2 h with stirring at the temperature. After cooling to room temperature, ethyl acetate (20 mL) was added, and the unreacted zinc powder was filtered off. The filtrate was concentrated to dryness. To the residue was added saturated NaHCO₃ solution (10 mL) and the mixture was extracted with ethyl acetate (15 mL×3). The organic phases were combined, dried over anhydrous sodium sulfate, and filtered. The filtrate was concentrated. The residue was passed through a silica gel column to afford 80 mg of a white solid in a yield of 71.4%. LC-MS (APCI): m/z=574.2 (M+1)⁺. ¹H NMR (400 MHz, DMSO-d₆) δ 12.64 (s, 1H), 10.09 (s, 1H), 8.28 (d, J=8.0 Hz, 1H), 7.79 (d, J=8.8 Hz, 1H), 7.48 (s, 1H), 7.40 (d, J=8.8 Hz, 1H), 7.25 (dd, J=8.8 Hz, J=1.6 Hz, 1H), 7.02-6.98 (m, 3H), 4.04 (s, 2H), 3.84-3.80 (m, 2H), 3.73-3.68 (m, 1H), 3.50 (t, J=9.6 Hz, 2H), 1.98-1.93 (m, 2H), 1.40-1.33 (m, 2H).

Example 7: Preparation of N-(5-((3,5-difluorophenyl)methyl-d₂)-1H-indazol-3-yl)-4-(4-methylpiperazin-1-yl)-2-((tetrahydro-2H-pyran-4-yl)amino)benzamide, Compound T-7, with the Formula

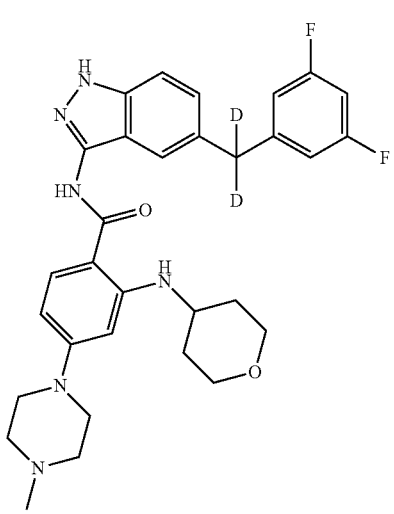

T-7

The following route is used for synthesis:

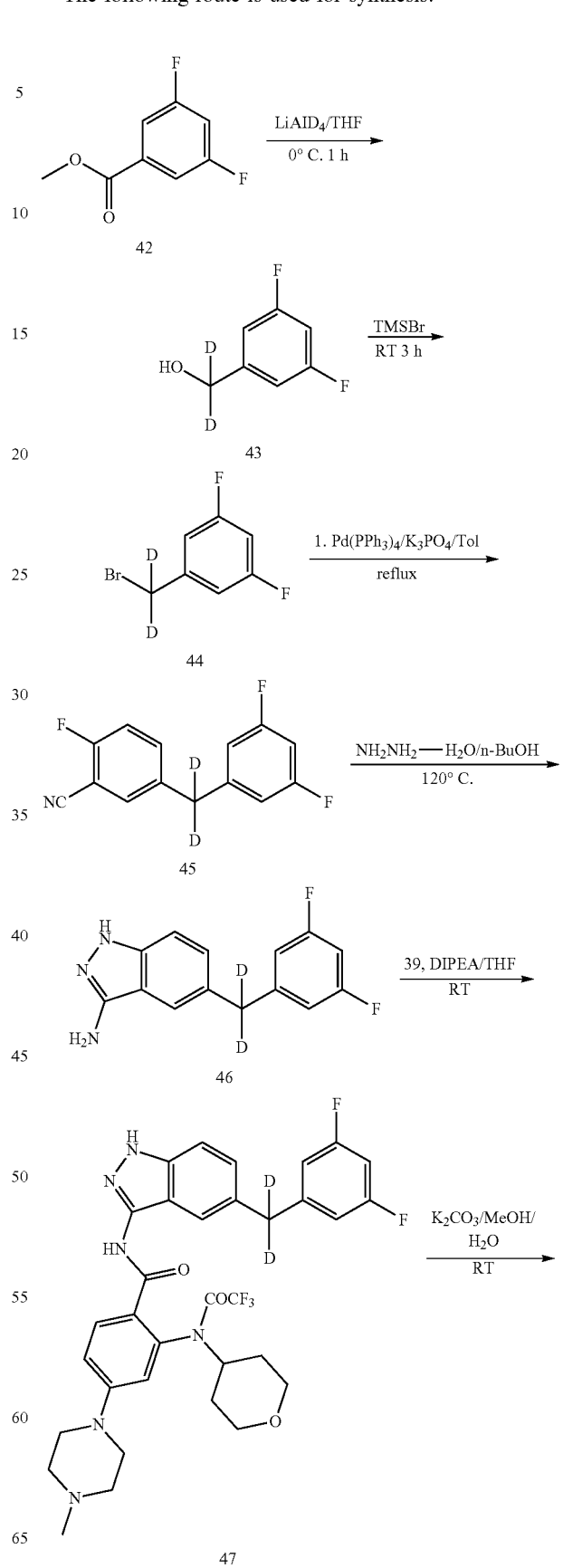

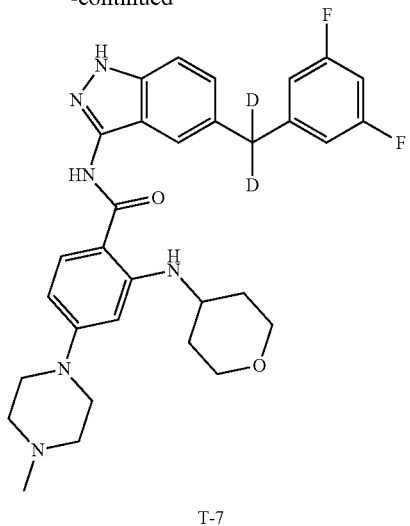

T-7

Step 1 Synthesis of Compound 43

To a 50 mL single-necked flask equipped with a magnetic stirrer were added compound 42 (1.73 g, 10 mmol) and anhydrous tetrahydrofuran (20 mL), and cooled to 0° C. under nitrogen atmosphere. To the mixture was added slowly deuterated lithium aluminum hydride (0.42 g, 10 mmol). The reaction was stirred at 0° C. for 1 h. A solid form of sodium sulfate decahydrate was slowly added to quench the reaction until no bubbling. To the mixture was added dichloromethane (40 mL) and filtered. The filtrate was dried over anhydrous sodium sulfate, filtered, and rotary evaporated to dryness to afford 1.2 g of a white solid in a yield of 82.2%. LC-MS (APCI): m/z=147.1 (M+1)$^+$. 1H NMR (400 MHz, CDCl$_3$) δ (ppm) 6.90-6.85 (m, 2H), 6.74-6.68 (m, 1H), 2.12 (s, 1H).

Step 2 Synthesis of Compound 44

To a 50 mL single-necked flask under magnetic stirring, were added sequentially compound 43 (3.93 g, 26.9 mmol) and bromotrimethylsilane (4.53 g, 29.6 mmol). The reaction was stirred at room temperature under nitrogen atmosphere for 2 hours. To the mixture was added ethyl acetate (50 mL). The mixture was washed with water (10 mL) and then saturated brine (10 mL), dried over anhydrous sodium sulfate and concentrated to afford 4.4 g of a colorless oil in a yield of 78.6%. LC-MS (APCI): m/z=209.0 (M+1)$^+$.

Step 3 Synthesis of Compound 45

To a 250 mL three-necked flask equipped with a magnetic stirrer and a condenser were added sequentially toluene (50 mL), compound 1 (2.5 g, 15.15 mmol), compound 44 (3.9 g, 16.65 mmol), and K$_3$PO$_4$ (6.4 g, 30.30 mmol). The flask was vacuumed and purged with nitrogen. Pd(PPh$_3$)$_4$ (385 mg, 0.33 mmol) was added, and the flask was again vacuumed and purged with nitrogen for three times. The mixture was heated to 110° C., and reacted at the temperature with stirring for 5 hours. After cooling to room temperature, ethyl acetate (100 mL) was added, and the resulting solid was filtered. The filtrate was concentrated. The residue was passed through a silica gel column to afford 2.7 g of a white solid in a yield of 72.2%. 1H NMR (400 MHz, CDCl$_3$) δ (ppm) 7.43-7.39 (m, 2H), 7.18 (t, J=8.8 Hz, 1H), 6.73-6.66 (m, 3H).

Step 4 Synthesis of Compound 46

To a 100 mL single-necked flask equipped with a magnetic stirrer and a condenser were added sequentially n-butanol (275 mL), compound 45 (2.7 g, 15.96 mmol) and hydrazine hydrate (2.74 g, 54.8 mmol). The mixture was heated to 120° C., and reacted with stirring at the temperature overnight. After cooling to room temperature, the reaction solution was concentrated. The residue was passed through a silica gel column to afford 1.7 g of a white solid in a yield of 60.1%. LC-MS (APCI): m/z=262.1 (M+1)$^+$. 1H NMR (400 MHz, DMSO-d$_6$) δ (ppm) 11.32 (s, 1H), 7.53 (s, 1H), 7.18-7.11 (m, 2H), 7.05-7.00 (m, 1H), 6.95-6.92 (m, 2H), 5.25 (br s, 2H).

Step 5 Synthesis of Compound 47

Under nitrogen atmosphere and at 0° C., to a solution of compound 39 (940 mg, 1.77 mmol) in anhydrous dichloromethane (10 mL) under magnetic stirring was added anhydrous DMF (3 drops) and then added slowly oxalyl chloride (4.4 mL, 8.8 mmol, 2 M solution in dichloromethane) dropwise. The reaction was stirred at room temperature under nitrogen atmosphere for 3 hours. Under reduced pressure, the solvent and excess oxalyl chloride were evaporated and co-evaporated twice with anhydrous dichloromethane. The residue was dissolved in anhydrous THF (3 mL) and ready for use. Compound 46 (219 mg, 0.85 mmol) and anhydrous tetrahydrofuran (5 mL) were added to another 50 mL two-necked flask, and dissolved with stirring. DIPEA (437 mg, 3.38 mmol) was added under nitrogen atmosphere, and cooled to 0° C. To the mixture was added slowly the above solution of acyl chloride dropwise. After the dropwise addition, the ice bath was removed, and the reaction was stirred at room temperature overnight. The solvent was evaporated under reduced pressure. The residue was passed through a silica gel column to afford 0.66 g of a white solid in a yield of 56.5%. LC-MS (APCI): m/z=659.3 (M+1)$^+$.

Step 6 Synthesis of T-7

To a solution of compound 47 (0.66 g, 1.0 mmol) in methanol/water (11 mL, 10/1) under magnetic stirring was added potassium carbonate (0.42 g, 3.0 mmol). The reaction was stirred at room temperature under nitrogen atmosphere for 3 hours. To the mixture was added water (30 mL), and a large amount of a grey solid was precipitated. The solid was filtered, washed with water (10 mL), dissolved in dichloromethane (20 mL), dried and concentrated. The residue was passed through a silica gel column to afford 0.4 g of a white solid in a yield of 71.0%. LC-MS (APCI): m/z=561.2 (M+1)$^+$. 1H NMR (400 MHz, CDCl$_3$) δ (ppm) 8.52 (s, 1H), 8.14 (d, J=8.0 Hz, 1H), 7.76 (s, 1H), 7.56 (d, J=8.8 Hz, 1H), 7.31 (d, J=8.8 Hz, 1H), 7.16 (dd, J=8.8 Hz, J=2.0 Hz, 1H), 6.72-6.69 (m, 2H), 6.64-6.59 (m, 1H), 6.23 (dd, J=8.8 Hz, J=2.0 Hz, 1H), 6.10 (s, 1H), 4.01-3.95 (m, 2H), 3.60-3.52 (m, 3H), 3.35 (t, J=4.8 Hz, 4H), 2.62 (t, J=4.8 Hz, 4H), 2.40 (s, 3H), 2.05-2.01 (m, 2H).

Example 8: Preparation of N-(5-(3,5-difluorobenzyl)-1H-indazol-3-yl)-4-(4-methylpiperazin-1-yl)-2-((tetrahydro-2H-pyran-4-yl-2,2,6,6-d₄)amino)benzamide, Compound T-8, with the Formula
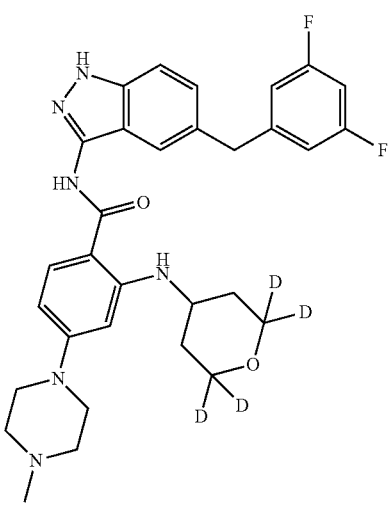
T-8
The following route is used for synthesis:
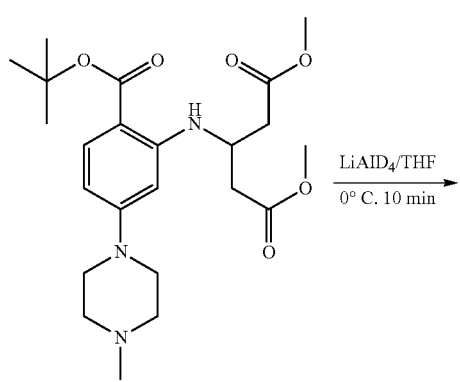
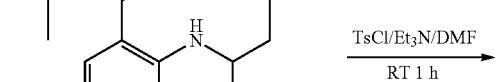
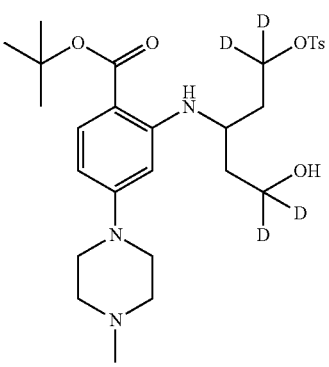
50
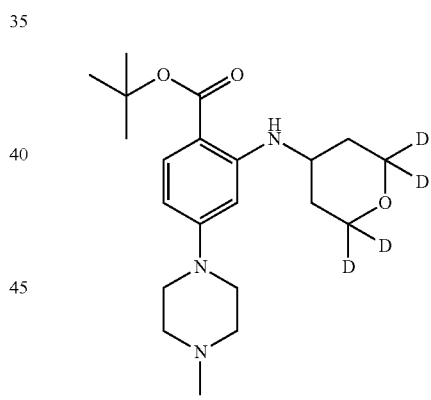
51
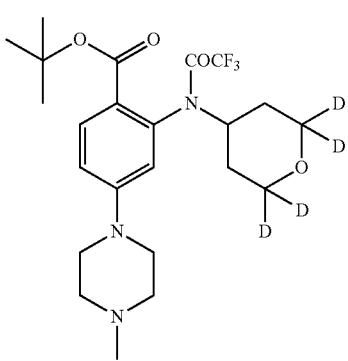
52
53

-continued

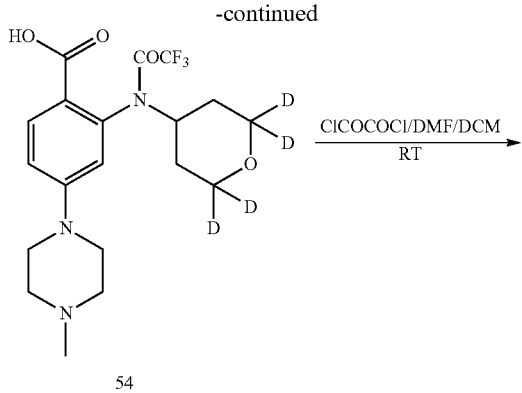

54

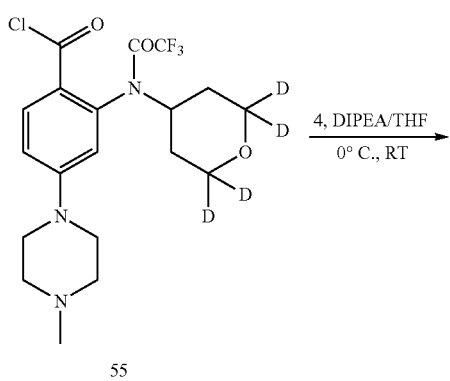

55

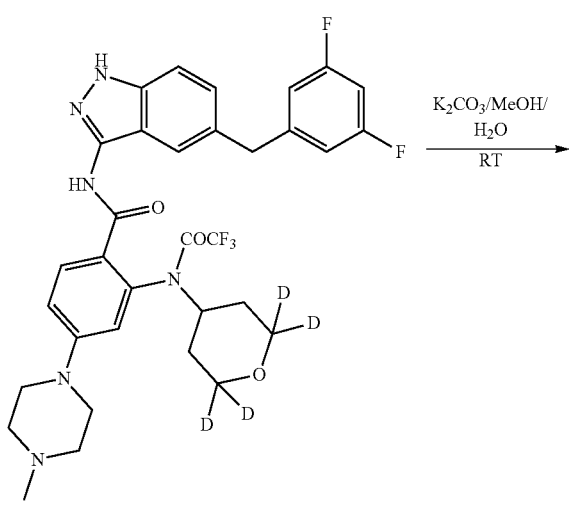

56

-continued

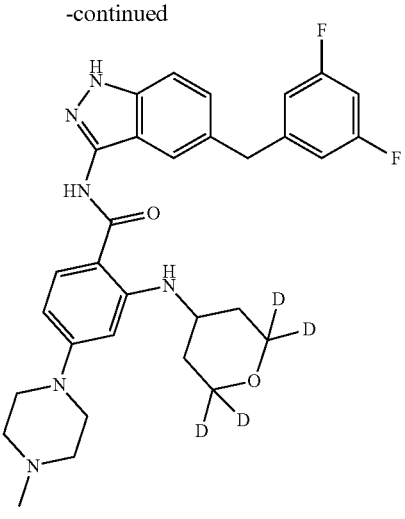

T-8

Step 1 Synthesis of Compound 49

To a 50 mL single-necked flask equipped with a magnetic stirrer and a condenser were added sequentially acetic acid (30 mL), compound 35 (3.0 g, 10.31 mmol), compound 48 (2.69 g, 15.46 mmol), and zinc powder (2.68 g, 41.22 mmol). The mixture was heated to 100° C., and the reaction was stirred at the temperature under nitrogen atmosphere overnight. After cooling to room temperature, ethyl acetate (40 mL) was added. The mixture was filtered and washed with ethyl acetate (10 mL). The organic phases were combined and concentrated to dryness. To the residue was added a saturated aqueous solution of sodium bicarbonate (20 mL) and extracted with ethyl acetate (40 mL×3). The organic phases were combined, dried over anhydrous sodium sulfate, filtered and concentrated. The residue was passed through a silica gel column to afford 2.0 g of a colorless oil in a yield of 44.32%. LC-MS (APCI): m/z=450.3 (M+1)$^+$.

Step 2 Synthesis of Compound 50

To a 50 mL single-necked flask equipped with a magnetic stirrer and a condenser were added anhydrous tetrahydrofuran (20 mL) and compound 49 (2.0 g, 4.45 mmol), and cooled to 0° C. under nitrogen atmosphere. To the mixture was added slowly deuterated lithium aluminum hydride (0.37 g, 8.91 mmol). The reaction was stirred at 0° C. for 10 min. A solid form of sodium sulfate decahydrate was slowly added to quench the reaction until no bubbling. To the mixture was added dichloromethane (40 mL) and filtered. The filtrate was dried over anhydrous sodium sulfate, filtered, and rotary evaporated to dryness to afford 847 mg of a colorless oil in a yield of 45.6%. LC-MS (APCI): m/z=398.3 (M+1)$^+$. $^1$H NMR (400 MHz, CDCl$_3$) δ 7.75-7.70 (m, 2H), 6.31 (d, J=2.0 Hz, 1H), 6.14 (dd, J=8.4 Hz, J=2.0 Hz, 1H), 3.97-3.89 (m, 1H), 3.32 (t, J=4.2 Hz, 3H), 2.55 (t, J=4.2 Hz, 4H), 2.35 (s, 3H), 1.85-1.81 (m, 4H), 1.55 (s, 9H).

Step 3 Synthesis of Compound 51

To a 50 mL single-necked flask with a magnetic stirrer were added sequentially compound 50 (847 mg, 2.03 mmol), dichloromethane (5 mL), DMF (5 mL) and triethylamine (308 mg, 3.04 mmol) and cooled in a cold water bath. A solution of p-toluenesulfonyl chloride (387 mg, 2.03 mmol) in dichloromethane (5 mL) was added slowly dropwise. After the dropwise addition, the ice bath was removed, and the reaction was stirred at room temperature under nitrogen atmosphere overnight. The mixture was rotary evaporated to dryness. The residue was passed through a silica gel column to afford 770 mg of a colorless oil in a yield of 70.2%. LC-MS (APCI): m/z=552.3 (M+1)$^+$.

Step 4 Synthesis of Compound 52

To a 25 mL single-necked flask equipped with a magnetic stirrer were added sequentially compound 51 (770 mg, 1.4 mmol) and anhydrous THF (10 mL). The mixture was cooled to 0° C. under nitrogen atmosphere, and NaH (84 mg, 2.1 mmol, 60% in mineral oil) was slowly added. After the addition, the mixture was slowly heated to room temperature and reacted for 3 hours. The reaction was quenched with water (10 mL) and extracted with ethyl acetate (15 mL×3). The organic phases were combined, dried over anhydrous sodium sulfate, filtered, and concentrated. The residue was passed through a silica gel column to afford 260 mg of a white solid in a yield of 49.0%. LC-MS: m/z=380.3 (M+1)$^+$. $^1$H NMR (500 MHz, CDCl$_3$) δ 7.91 (d, J=7.0 Hz, 1H), 7.75 (d, J=9.0 Hz, 1H), 6.15 (dd, J=9.0 Hz, J=3.0 Hz, 1H), 6.02 (d, J=3.0 Hz, 1H), 3.29 (t, J=5.0 Hz, 4H), 2.54 (t, J=5.0 Hz, 4H), 2.35 (s, 3H), 2.05-2.01 (m, 2H), 1.68-1.61 (m, 2H), 1.55 (s, 9H).

Step 5 Synthesis of Compound 53

At 0° C., to a solution of compound 52 (260 mg, 0.686 mmol) in dichloromethane (8 mL) under magnetic stirring was added triethylamine (111 mg, 1.1 mmol), and then added slowly TFAA (0.25 mL, 0.892 mmol) dropwise. The reaction was stirred at room temperature for 4 hours. Water (10 mL) was added, and the organic layer was separated. The aqueous phase was extracted with dichloromethane (10 mL×2), dried over anhydrous sodium sulfate and filtered. The filtrate was concentrated. The residue was passed through a silica gel column to afford 420 mg of a colorless oil in a yield of 98.2%. LC-MS (APCI): m/z=476.1 (M+1)$^+$.

Step 6 Synthesis of Compound 54

To a solution of compound 53 (420 mg, 0.884 mmol) in dichloromethane (10 mL) under magnetic stirring was added trifluoroacetic acid (3 mL) at 0° C. The reaction was stirred at room temperature under nitrogen atmosphere overnight. The solvent and the trifluoroacetic acid were evaporated under reduced pressure. To the residue was added diethyl ether (20 mL). The mixture was stirred for 20 minutes and a large amount of a white solid was precipitated. The solid was filtered, washed with diethyl ether and dried to afford 330 mg of a white solid in a yield of 70.0%. LC-MS (APCI): m/z=420.2 (M+1)$^+$.

Step 7 Synthesis of Compound 56

Under nitrogen atmosphere and at 0° C., to a solution of compound 54 (330 mg, 0.62 mmol) in anhydrous dichloromethane (6 mL) under magnetic stirring was added anhydrous DMF (2 drops), and then added slowly oxalyl chloride (1.6 mL, 3.2 mmol, 2 M solution in dichloromethane) dropwise. The reaction was stirred at room temperature under nitrogen atmosphere for 3 hours. Under reduced pressure, the solvent and excess oxalyl chloride were evaporated and co-evaporated twice with anhydrous dichloromethane. The residue was dissolved in anhydrous THF (3 mL) and ready for use. Compound 4 (145 mg, 0.59 mmol) and anhydrous tetrahydrofuran (3 mL) were added to another 50 mL two-necked flask, and dissolved with stirring. DIPEA (320 mg, 2.48 mmol) was added under nitrogen atmosphere, and cooled to 0° C. To the mixture was added slowly the above solution of acyl chloride dropwise. After the dropwise addition, the ice bath was removed, and the reaction was stirred at room temperature overnight. The solvent was evaporated under reduced pressure. The residue was passed through a silica gel column to afford 0.28 g of a white solid in a yield of 67.7%. LC-MS (APCI): m/z=661.3 (M+1)$^+$.

Step 8 Synthesis of T-8

To a solution of compound 56 (0.28 g, 0.42 mmol) in methanol/water (11 mL, 10/1) under magnetic stirring was added potassium carbonate (0.18 g, 1.27 mmol). The reaction was stirred at room temperature under nitrogen atmosphere for 3 hours. To the mixture was added water (30 mL), and a large amount of a grey solid was precipitated. The solid was filtered, washed with water (10 mL), dissolved in dichloromethane (20 mL), dried and concentrated. The residue was passed through a silica gel column to afford 165 mg of a white solid in a yield of 69.6%. LC-MS (APCI): m/z=565.2 (M+1)$^+$. $^1$H NMR (400 MHz, CDCl$_3$) δ 8.52 (s, 1H), 8.14 (d, J=8.0 Hz, 1H), 7.76 (s, 1H), 7.56 (d, J=8.8 Hz, 1H), 7.31 (d, J=8.8 Hz, 1H), 7.16 (dd, J=8.8 Hz, J=2.0 Hz, 1H), 6.72-6.69 (m, 2H), 6.64-6.59 (m, 1H), 6.23 (dd, J=8.8 Hz, J=2.0 Hz, 1H), 6.10 (s, 1H), 4.05 (s, 2H), 3.35 (t, J=4.8 Hz, 4H), 2.62 (t, J=4.8 Hz, 4H), 2.40 (s, 3H), 2.05-2.01 (m, 2H).

Example 9: Preparation of

N-(5-(4-d-3,5-(difluorobenzyl)-1H-indazol-3-yl)-4-(4-methylpiperazin-1-yl)-2-((tetrahydro-2H-pyran-4-yl)amino) benzamide, Compound T-9, with the Formula

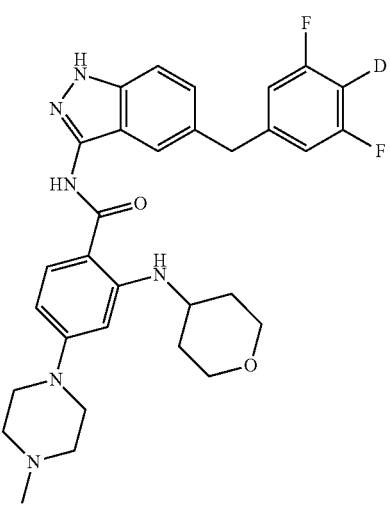

T-9

The following route is used for synthesis:

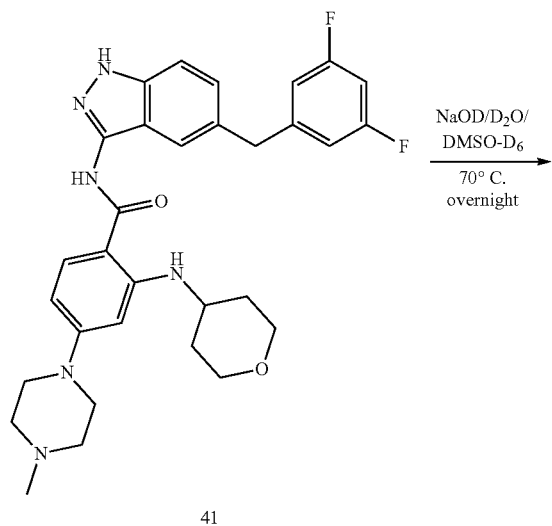

41

To a 50 mL single-necked flask equipped with a magnetic stirrer and a condenser were added sequentially compound 41 (200 mg, 0.35 mmol), D₂O (5 mL), DMSO-D₆ (5 mL) and 40% solution of NaOD in D₂O (180 mg, 0.178 mL). The mixture was heated to 70° C., and the reaction was stirred at the temperature under nitrogen atmosphere overnight. After cooling to room temperature, the mixture was extracted with ethyl acetate (20 mL×3). The organic phases were combined, washed with water (40 mL×3), dried over anhydrous sodium sulfate, filtered and concentrated. The residue was passed through a silica gel column to afford 120 mg of a white solid in a yield of 60%. LC-MS (APCI): m/z=562.4 (M+1)⁺. ¹H NMR (DMSO-d₆, 300 MHz) δ12.64 (s, 1H), 10.09 (s, 1H), 8.29 (d, J=5.7 Hz, 1H), 7.79 (d, J=6.9 Hz, 1H), 7.48 (s, 1H), 7.40 (d, J=6.6 Hz, 1H), 7.25 (d, J=6.6 Hz, 1H), 6.98 (d, J=6.0 Hz, 2H), 6.23 (d, J=6.6 Hz, 1H), 6.13 (s, 1H), 4.04 (s, 2H), 3.83-3.78 (m, 2H), 3.68 (s, 1H), 3.49 (t, J=7.5 Hz, 2H), 3.26 (s, 4H), 2.44 (s, 4H), 2.23 (s, 3H), 1.93 (d, J=8.7 Hz, 2H), 1.38-1.29 (m, 2H).

Example 10: Preparation of N-(5-((3,5-difluorophenyl)methyl-d₂)-1H-indazol-3-yl)-4-(4-methylpiperazin-1-yl)-2-((tetrahydro-2H-pyran-4-yl)amino)benzamide-3,5-d₂, Compound T-10, with the Formula The following route is used for synthesis:

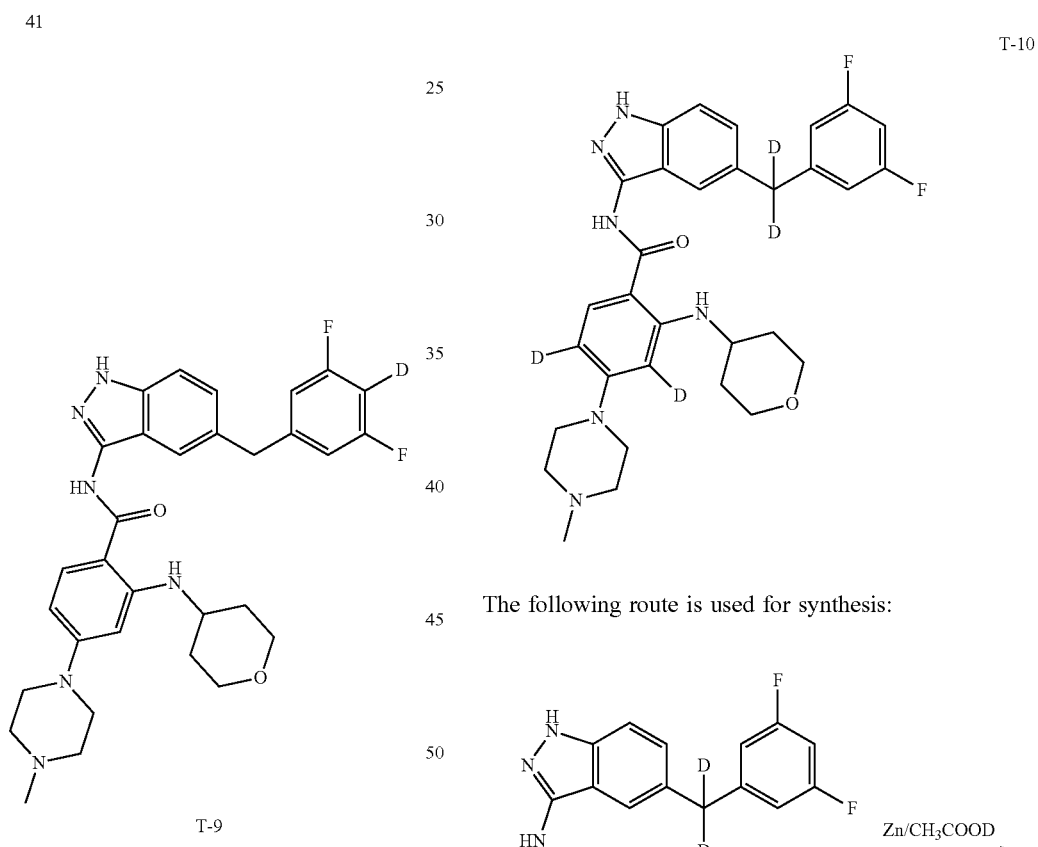

T-10

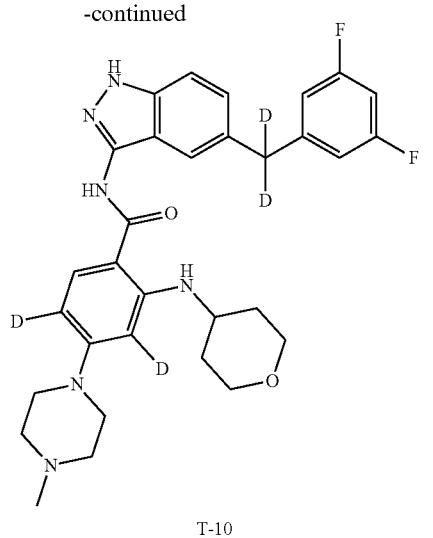

To a 50 mL single-necked flask equipped with a magnetic stirrer and a condenser were added sequentially compound T-7 (112 mg, 0.2 mmol) and CH₃COOD (8 mL). To the mixture was added zinc powder (56 mg, 1 mmol) with stirring. The flask was vacuumed and purged with nitrogen for three times. The mixture was heated to 70° C., and reacted for 2 h with stirring at the temperature. After cooling to room temperature, ethyl acetate (20 mL) was added, and the unreacted zinc powder was filtered off. The filtrate was concentrated to dryness. To the residue was added saturated NaHCO₃ solution (10 mL) and the mixture was extracted with ethyl acetate (15 mL×3). The organic phases were combined, dried over anhydrous sodium sulfate, and filtered. The filtrate was concentrated. The residue was passed through a silica gel column to afford 80 mg of a white solid in a yield of 71.4%. LC-MS (APCI): m/z=566.2 (M+1)⁺. 1H NMR (400 MHz, DMSO-D₆) δ 12.64 (s, 1H), 10.09 (s, 1H), 8.28 (d, J=8.0 Hz, 1H), 7.79 (d, J=8.8 Hz, 1H), 7.48 (s, 1H), 7.40 (d, J=8.8 Hz, 1H), 7.25 (dd, J=8.8 Hz, J=1.6 Hz, 1H), 7.02-6.98 (m, 3H), 3.84-3.80 (m, 2H), 3.73-3.68 (s, 1H), 3.50 (t, J=9.6 Hz, 2H), 3.26 (t, J=4.8 Hz, 4H), 2.44 (t, J=4.8 Hz, 4H), 1.98-1.93 (m, 2H), 1.40-1.33 (m, 2H).

Example 11: Preparation of N-(5-((3,5-difluorophenyl)methyl-d₂)-1H-indazol-3-yl)-4-(4-(methyl-d₃) piperazin-1-yl)-2-((tetrahydro-2H-pyran-4-yl)amino) benzamide, Compound T-11, with the Formula

T-11

The following route is used for synthesis:

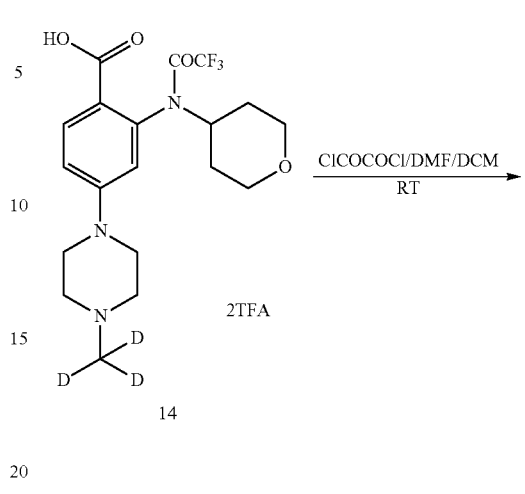

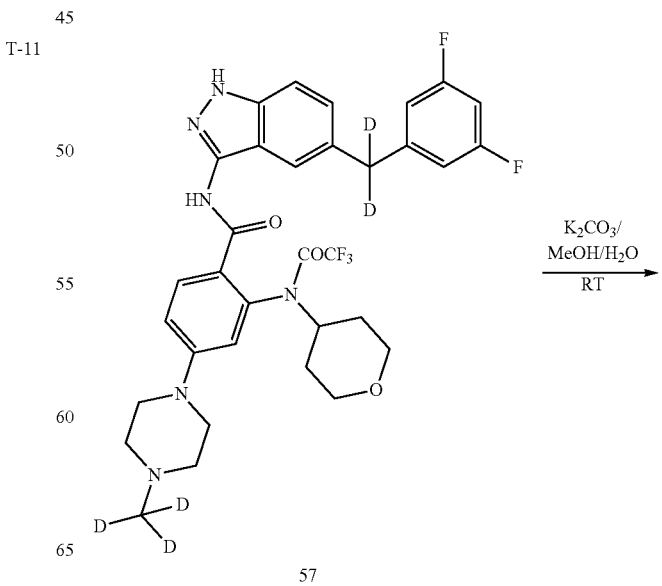

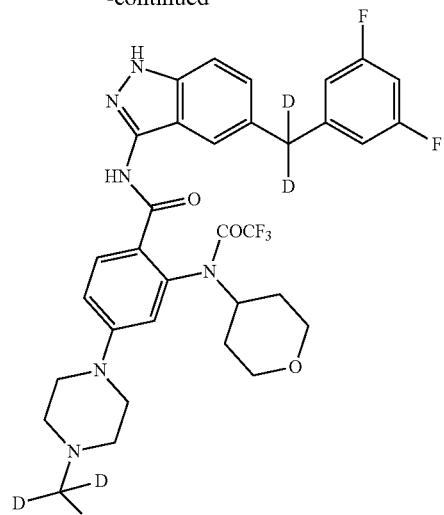

T-11

Step 1 Synthesis of Compound 57

Under nitrogen atmosphere and at 0° C., to a solution of compound 14 (940 mg, 1.77 mmol) in anhydrous dichloromethane (10 mL) under magnetic stirring was added anhydrous DMF (3 drops) and then added slowly oxalyl chloride (4.4 mL, 8.8 mmol, 2 M solution in dichloromethane) dropwise. The reaction was stirred at room temperature under nitrogen atmosphere for 3 hours. Under reduced pressure, the solvent and excess oxalyl chloride were evaporated and co-evaporated twice with anhydrous dichloromethane. The residue was dissolved in anhydrous THF (3 mL) and ready for use. Compound 46 (219 mg, 0.85 mmol) and anhydrous tetrahydrofuran (5 mL) were added to another 50 mL two-necked flask, and dissolved with stirring. DIPEA (437 mg, 3.38 mmol) was added under nitrogen atmosphere, and cooled to 0° C. To the mixture was added slowly the above solution of acyl chloride dropwise. After the dropwise addition, the ice bath was removed, and the reaction was stirred at room temperature overnight. The solvent was evaporated under reduced pressure. The residue was passed through a silica gel column to afford 0.66 g of a white solid in a yield of 56.5%. LC-MS (APCI): m/z=662.3 (M+1)$^+$.

Step 2 Synthesis of T-11

To a solution of compound 57 (0.66 g, 1.0 mmol) in methanol/water (11 mL, 10/1) under magnetic stirring was added potassium carbonate (0.42 g, 3.0 mmol). The reaction was stirred at room temperature under nitrogen atmosphere for 3 hours. To the mixture was added water (30 mL), and a large amount of a grey solid was precipitated. The solid was filtered, washed with water (10 mL), dissolved in dichloromethane (20 mL), dried and concentrated. The residue was passed through a silica gel column to afford 0.4 g of a white solid in a yield of 71.0%. LC-MS (APCI): m/z=566.2 (M+1)$^+$. $^1$H NMR (400 MHz, CDCl$_3$) δ 8.52 (s, 1H), 8.14 (d, J=8.0 Hz, 1H), 7.76 (s, 1H), 7.56 (d, J=8.8 Hz, 1H), 7.31 (d, J=8.8 Hz, 1H), 7.16 (dd, J=8.8 Hz, J=2.0 Hz, 1H), 6.72-6.69 (m, 2H), 6.64-6.59 (m, 1H), 6.23 (dd, J=8.8 Hz, J=2.0 Hz, 1H), 6.10 (s, 1H), 4.01-3.95 (m, 2H), 3.60-3.52 (m, 3H), 3.35 (t, J=4.8 Hz, 4H), 2.62 (t, J=4.8 Hz, 4H), 2.05-2.01 (m, 2H).

Example 12: Preparation of N-(5-((3,5-difluorophenyl)methyl)-1H-indazol-3-yl)-4-(4-methylpiperidin-1-yl)-2-((tetrahydro-2H-pyran-4-yl-2,2,6,6-d$_4$)amino)benzamide-3,5-d$_2$, Compound T-12, with the formula:

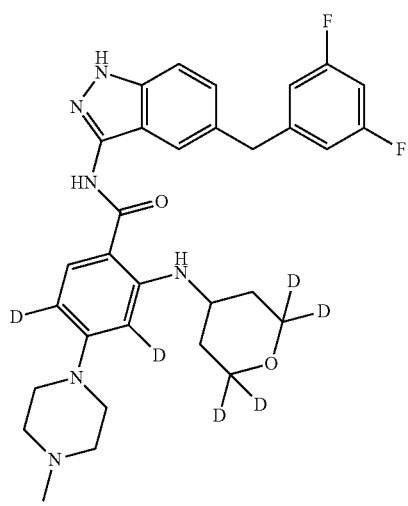

T-12

The following route is used for synthesis:

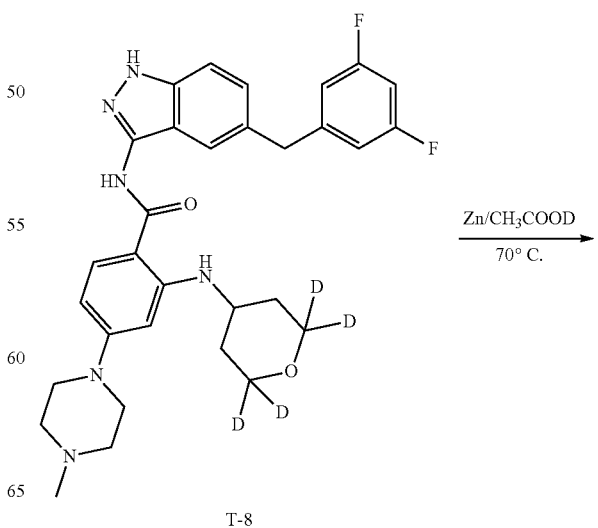

T-8

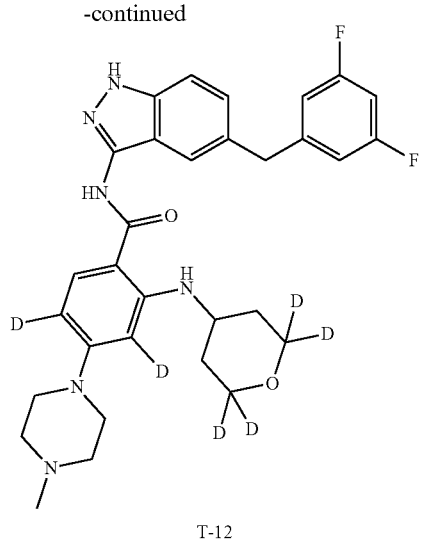

T-12

To a 50 mL single-necked flask equipped with a magnetic stirrer and a condenser were added sequentially compound T-8 (112 mg, 0.2 mmol), and CH₃COOD (8 mL). To the mixture was added zinc powder (56 mg, 1 mmol) with stirring. The flask was vacuumed and purged with nitrogen for three times. The mixture was heated to 70° C., and reacted for 2 h with stirring at the temperature. After cooling to room temperature, ethyl acetate (20 mL) was added, and the unreacted zinc powder was filtered off. The filtrate was concentrated to dryness. To the residue was added saturated NaHCO₃ solution (10 mL) and the mixture was extracted with ethyl acetate (15 mL×3). The organic phases were combined, dried over anhydrous sodium sulfate, and filtered. The filtrate was concentrated. The residue was passed through a silica gel column to afford 80 mg of a white solid in a yield of 71.4%. LC-MS (APCI): m/z=571.2 (M+1)⁺. 1H NMR (400 MHz, DMSO-d₆) δ 12.64 (s, 1H), 10.09 (s, 1H), 8.28 (d, J=8.0 Hz, 1H), 7.79 (d, J=8.8 Hz, 1H), 7.48 (s, 1H), 7.40 (d, J=8.8 Hz, 1H), 7.25 (dd, J=8.8 Hz, J=1.6 Hz, 1H), 7.02-6.98 (m, 3H), 3.73-3.68 (s, 1H), 3.26 (t, J=4.8 Hz, 4H), 2.44 (t, J=4.8 Hz, 4H), 1.98-1.93 (m, 2H), 1.40-1.33 (m, 2H).

Example 13: Preparation of N-(5-((3,5-difluorophenyl)methyl-d₂)-1H-indazol-3-yl)-4-(4-methylpiperazin-1-yl-2,2,3,3, 5,5,6,6-d₈)-2-((tetrahydro-2H-pyran-4-yl)amino)benzamide, Compound T-13, with the Formula Step 1 Synthesis of Compound 58

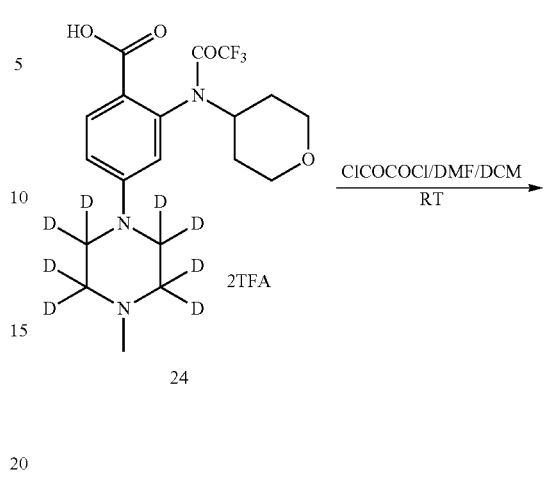

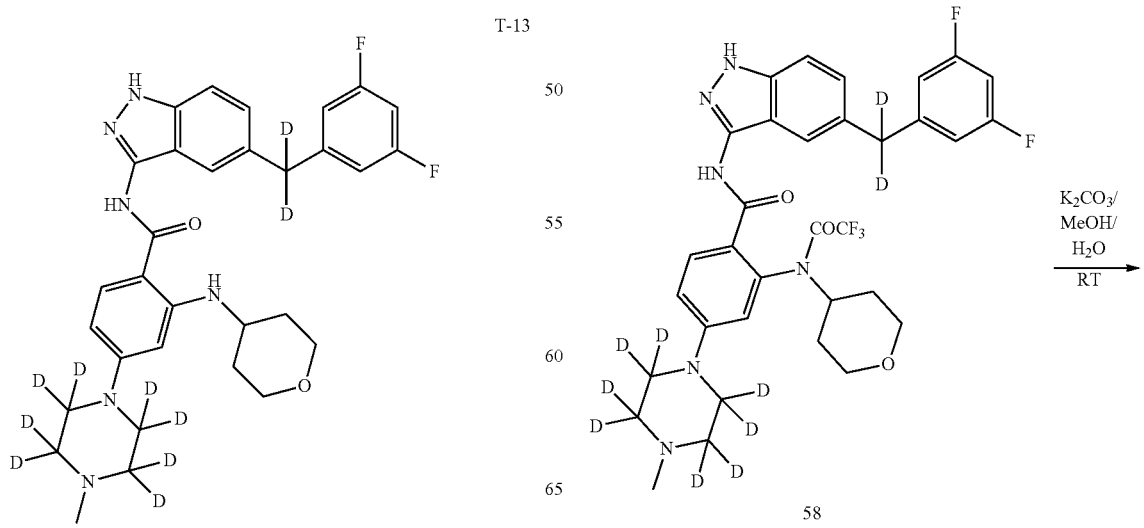

-continued

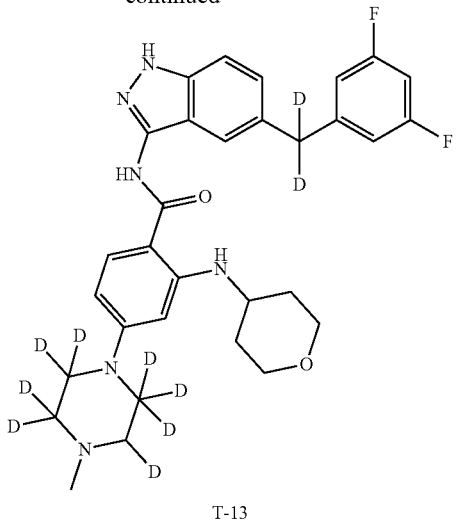

T-13

Under nitrogen atmosphere and at 0° C., to a solution of compound 24 (940 mg, 1.77 mmol) in anhydrous dichloromethane (10 mL) under magnetic stirring was added anhydrous DMF (3 drops), and then added slowly oxalyl chloride (4.4 mL, 8.8 mmol, 2 M solution in dichloromethane) dropwise. The reaction was stirred at room temperature under nitrogen atmosphere for 3 hours. Under reduced pressure, the solvent and excess oxalyl chloride were evaporated and co-evaporated twice with anhydrous dichloromethane. The residue was dissolved in anhydrous THF (3 mL) and ready for use. Compound 46 (219 mg, 0.85 mmol) and anhydrous tetrahydrofuran (5 mL) were added to another 50 mL two-necked flask, and dissolved with stirring. DIPEA (437 mg, 3.38 mmol) was added under nitrogen atmosphere, and cooled to 0° C. To the mixture was added slowly the above solution of acyl chloride dropwise. After the dropwise addition, the ice bath was removed, and the reaction was stirred at room temperature overnight. The solvent was evaporated under reduced pressure. The residue was passed through a silica gel column to afford 0.66 g of a white solid in a yield of 56.5%. LC-MS (APCI): m/z=667.3 (M+1)$^+$.

Step 2 Synthesis of T-13

To a solution of compound 58 (0.66 g, 1.0 mmol) in methanol/water (11 mL, 10/1) under magnetic stirring was added potassium carbonate (0.42 g, 3.0 mmol). The reaction was stirred at room temperature under nitrogen atmosphere for 3 hours. To the mixture was added water (30 mL), and a large amount of a grey solid was precipitated. The solid was filtered, washed with water (10 mL), dissolved in dichloromethane (20 mL), dried and concentrated. The residue was passed through a silica gel column to afford 0.4 g of a white solid in a yield of 71.0%. LC-MS (APCI): m/z=566.2 (M+1)$^+$. 1H NMR (400 MHz, CDCl$_3$) δ 8.52 (s, 1H), 8.14 (d, J=8.0 Hz, 1H), 7.76 (s, 1H), 7.56 (d, J=8.8 Hz, 1H), 7.31 (d, J=8.8 Hz, 1H), 7.16 (dd, J=8.8 Hz, J=2.0 Hz, 1H), 6.72-6.69 (m, 2H), 6.64-6.59 (m, 1H), 6.23 (dd, J=8.8 Hz, J=2.0 Hz, 1H), 6.10 (s, 1H), 4.01-3.95 (m, 2H), 3.60-3.52 (m, 3H), 2.44 (s, 3H), 2.05-2.01 (m, 2H), 1.65-1.60 (m, 2H).

Biological Activity Test
(1) Kinase Inhibition Assay.

Compound preparation: Test compounds were dissolved in DMSO to prepare 20 mM stock solutions. Before use, compounds were diluted to 0.1 mM in DMSO (a dilution with a concentration 100 times the final concentration) and subjected to a 3-fold gradient dilution with 11 concentrations. When using, the compounds were diluted with buffer to a dilution with a concentration 4 times the final concentration.

Kinase assay: After the buffer was prepared, the enzyme was mixed with different concentrations of pre-diluted compounds in duplex, and allowed to stand at room temperature for 30 minutes. The corresponding substrate and ATP were added and reacted at room temperature for 60 minutes (in which negative and positive controls were set). After the reaction was completed, an antibody was added for detection. After incubation for 60 minutes at room temperature, detection was carried out with Evnvision and data were collected. The enzyme activity in the presence of each concentration of the compounds disclosed herein was determined by Evnvision microplate reader, and the inhibitory activity of the compounds at different concentrations on the enzyme activity was calculated. Then, according to the four-parameter equation, the inhibitory activity of the compounds at different concentrations on the enzyme activity was fitted using Graphpad 5.0 software, and the IC$_{50}$ value was calculated.

The inhibitory activities of the compounds disclosed herein on ALK WT, ALK L1196M, TRK A, TRK B, and TRK C kinases were tested as described above. The results of kinase inhibition in the examples were shown in Table 1, wherein A represents IC$_{50}$≤1 nM, B represents IC$_{50}$ of 1-10 nM, C represents IC$_{50}$ of 10-100 nM, D represents IC$_{50}$ of 100-200 nM, and E represents IC$_{50}$≥200 nM.

As shown in Table 1, the compounds disclosed herein had significant inhibitory activity on protein kinase and generally had an IC$_{50}$ of less than 10 nM. For example, as compared to the compound Entrectinib which is not deuterated, the compounds disclosed herein exhibited superior inhibitory activity on ALK WT mutant (IC$_{50}$ less than 10 nM), exhibited a comparable inhibitory activity on ALK L119M mutant, and particularly, exhibited a strong inhibitory activity on TRKA/B/C (IC$_{50}$ less than 1 nM).

TABLE 1

Comparison of kinase inhibition

| Compound No. | ALK WT IC$_{50}$(nM) | ALK L1196M IC$_{50}$(nM) | TRK A IC$_{50}$(nM) | TRK B IC$_{50}$(nM) | TRK C IC$_{50}$(nM) |
|---|---|---|---|---|---|
| Entrectinib | C | D | A | A | A |
| T-1 | B | D | A | A | A |
| T-2 | B | D | A | A | A |
| T-3 | B | D | A | A | A |
| T-4 | C | D | A | A | A |
| T-5 | C | D | A | A | A |
| T-6 | B | D | A | A | A |
| T-7 | C | E | A | A | A |
| T-8 | B | D | A | A | A |
| T-9 | B | D | A | A | A |
| T-11 | B | D | A | A | A |
| T-12 | C | D | A | A | A |

(2) Cytotoxicity Assay

The inhibitory effects of example compounds on the cell viability of Ba/F3, Ba/F3 EML-ALK, Ba/F3 EML-ALK$^{L1196M}$, KM12 (TPM3-TRKA), and HCC-78 (SLC34A2-ROS1) cells were tested.

Materials and reagents: RPMI-1640 medium (GIBCO, catalog number A10491-01), fetal bovine serum (GIBCO, catalog number 10099141), antibiotics (Penicillin-Streptomycin), IL-3 (PeproTech), puromycin; cell lines: Ba/F3, Ba/F3 Bcr-Abl T315I (purchased from America Type Culture Collection, ATCC), live cell assay kit CellTiter-Glo4 (Promega, catalog number G7572), 96-well black-wall clear flat-bottom cell culture plate (Corning, catalog number 3340).

Assay methods: 1. Preparation of cell plates: Ba/F3, and Ba/F3 Bcr-Abl T315I cells were separately seeded in 96-well plates, and 8 ng/ml IL-3 was added to Ba/F3 cells. The cell plates were placed in a carbon dioxide incubator for culture overnight. 2. The test compounds were dissolved in DMSO and subjected to 3.16-fold gradient dilution with 9 compound concentrations in triplex. 3. Treatment of cells with compounds: The compounds were transferred to cell plates at a starting concentration of 10 μM. The cell plates were incubated in a carbon dioxide incubator for 3 days. 4. Detection: CellTiter-Glo reagent was added to the cell plates and incubated for 30 minutes at room temperature to stabilize the luminescence signal. Readings were performed using a PerkinElmer Envision multi-label analyzer.

The assay results were shown in Table 2, wherein A represented $IC_{50}$ of 1-10 nM, B represented $IC_{50}$ of 10-50 nM, C represented $IC_{50}$ of 50-150 nM, D represented $IC_{50}$ of 150-200 nM, and E represented $IC_{50} \geq 200$ nM.

TABLE 2

Comparison of cytotoxicity

| Compound No. | Ba/F3 EML-ALK $IC_{50}$(nM) | Ba/F3 EML-ALK$^{L1196M}$ $IC_{50}$(nM) | KM12 $IC_{50}$(nM) | HCC-78 $IC_{50}$(nM) |
|---|---|---|---|---|
| Entrectinib | C | E | A | B |
| T-1 | C | E | A | B |
| T-2 | C | E | A | B |
| T-3 | C | E | | |
| T-4 | C | E | | |
| T-5 | C | E | | |
| T-6 | C | E | | |
| T-7 | C | E | | |
| T-8 | C | E | | |
| T-9 | C | E | | |
| T-11 | B | E | | |
| T-12 | B | E | | |

As shown in Table 2, the compounds disclosed herein all showed excellent anticancer activity of inhibiting the growth of cancer cells expressing ALK mutant L1196M.

(3) Liver Microsomal Metabolism Assay

Microsome assay: Human liver microsomes: 0.5 mg/mL, Xenotech; Rat liver microsomes: 0.5 mg/mL, Xenotech; Coenzyme (NADPH/NADH): 1 mM, Sigma Life Science; Magnesium chloride: 5 mM, 100 mM phosphate buffer (pH 7.4).

Preparation of stock solutions: Powder of the compounds were accurately weighed and dissolved in DMSO to 5 mM.

Preparation of phosphate buffer (100 mM, pH7.4): A pre-prepared 0.5M potassium dihydrogen phosphate (150 mL) was mixed with 0.5M dibasic potassium phosphate (700 mL). The pH of the mixture was adjusted to 7.4 with 0.5M dibasic potassium phosphate solution. The mixture was diluted 5-fold with ultrapure water before use, and magnesium chloride was added to obtain a phosphate buffer (100 mM) containing 100 mM potassium phosphate, 3.3 mM magnesium chloride, pH 7.4.

A NADPH regeneration system solution (containing 6.5 mM NADP, 16.5 mM G-6-P, 3 U/mL G-6-P D, 3.3 mM magnesium chloride) was prepared and placed on wet ice prior to use.

Preparation of stop solution: an acetonitrile solution containing 50 ng/mL propranolol hydrochloride and 200 ng/mL tolbutamide (internal standard). 25057.5 μL of phosphate buffer (pH 7.4) was taken into a 50 mL centrifuge tube, to which 812.5 μL human liver microsomes were added, and mixed to obtain a liver microsome dilution with a protein concentration of 0.625 mg/mL. 25057.5 μL of phosphate buffer (pH 7.4) was taken into a 50 mL centrifuge tube, to which 812.5 μL SD rat liver microsomes were added, and mixed to obtain a liver microsome dilution with a protein concentration of 0.625 mg/mL.

Incubation of the samples: The stock solutions of the respective compounds were respectively diluted to 0.25 mM with an aqueous solution containing 70% acetonitrile, and used as a working solution, ready for use. 398 μL of the dilution of human liver microsomes or rat liver microsomes were added to 96-well incubation plates (N=2), respectively, and 2 μL of 0.25 mM working solution was added and mixed.

Metabolic stability assay: 300 μL of pre-chilled stop solution was added to each well of 96-well deep well plates and placed on ice as stop plates. The 96-well incubation plates and NADPH regeneration system were placed in a 37° C. water bath box, shaken at 100 rpm and pre-incubated for 5 min. 80 μL of incubation solution was taken out from each well of the incubation plates and added to the stop plates, mixed, and replenished with 20 μL of NADPH regeneration system solution as a 0-min sample. 80 μL of NADPH regeneration system solution was added to each well of the incubation plates to start the reaction and start counting. The corresponding compounds had a reaction concentration of 1 μM and the protein concentration was 0.5 mg/mL. Separately, 100 μL of the reaction solutions was taken at 10, 30, and 90 min reaction, respectively, added to stop plates, and vortexed for 3 minutes to terminate the reaction. The stop plates were centrifuged at 5000×g at 4° C. for 10 min. 100 μL of the supernatant was added to a 96-well plate to which 100 μL of distilled water was previously added, mixed, and analyzed by LC-MS/MS.

Data analysis: The peak areas of the corresponding compounds and internal standard were detected by LC-MS/MS system, and the ratio of the peak area of the compounds to the internal standard was calculated. The slope was measured by plotting the natural logarithm of the percent of compound remaining versus time, and $t_{1/2}$ and $CL_{int}$ were calculated according to the equation below, where V/M equals to 1/protein concentration.

$$t_{1/2} = -\frac{0.693}{\text{Slope}}, \quad CL_{int} = \frac{0.693}{t_{1/2}} \cdot \frac{V}{M}$$

The metabolic stability of the compounds in human and rat liver microsomes was evaluated by simultaneously testing and comparing the compounds disclosed herein and the non-deuterated compound. The half-life and liver intrinsic clearance as indicators of metabolic stability were shown in Table 3. The non-deuterated compound Entrectinib was used as a control sample in Table 3. As shown in Table 3, the compounds disclosed herein can significantly improve the metabolic stability as can be seen by comparing with the non-deuterated compound Entrectinib.

TABLE 3

Comparison of metabolic stability in representative example compounds and Entrectinib control

| Compound No. | Human liver microsome assay | | Rat liver microsome assay | |
| --- | --- | --- | --- | --- |
| | $t_{1/2}$ (min) | $CL_{int}$ (μL/min/mg) | $t_{1/2}$ (min) | $CL_{int}$ (μL/min/mg) |
| Entrectinib | 28.8 | 48.1 | 42.2 | 32.9 |
| T-1 | 39.9 | 34.7 | 65.2 | 21.3 |
| T-2 | 44.3 | 31.3 | 71.2 | 19.5 |
| T-3 | 35.4 | 39.2 | 50.7 | 27.3 |
| T-4 | 38.3 | 36.2 | 63.3 | 21.9 |
| T-5 | 28.8 | 48.2 | 44.7 | 31.0 |
| T-6 | 32.6 | 42.5 | 46.7 | 29.7 |
| T-7 | 27.1 | 51.1 | 41.1 | 33.7 |
| T-8 | 30.9 | 44.9 | 41.3 | 33.6 |
| T-9 | 29.2 | 47.5 | 41.1 | 33.7 |
| T-11 | 30.8 | 45.0 | 44.6 | 31.0 |
| T-12 | 28.3 | 48.9 | 41.8 | 33.2 |

(4) Pharmacokinetic Assay in Rats

Assay objective: after administration of test compounds to rats, the pharmacokinetic behavior of the compounds disclosed herein was investigated.

Assay Animals:

Species and strains: SD rat grade: SPF grade

Gender and quantity: male, 6

Weight range: 180 to 220 g (the actual weight range was from 187 to 197 g)

Source: shanghai sippr bk laboratory animals ltd.

Laboratory and Animal Qualification Certificate: SCXK (Shanghai) 2013-0016

Assay Procedure:

Before blood samples were collected, 20 μL of 2 M sodium fluoride solution (esterase inhibitor) was previously added to an EDTA-K2 anticoagulant tube, dried in an 80° C. oven, and placed in a 4° C. refrigerator.

Rats (male, weighing 187 to 197 g) were randomly divided into 2 groups, and were fasted overnight in the afternoon before the experiment but were allowed to drink water freely. Food was given 4 hours after the administration. Group A was given Entrectinib (3 mg/kg), and group B was given example compounds (3 mg/kg). About 100-200 μL of blood was taken from the orbital vein of rats at 15 min, 30 min, 1, 2, 3, 5, 8 and 10 h after administration, placed in a 0.5 mL Eppendorf tube with EDTA-K2 anticoagulant and mixed immediately. After anticoagulation, the tube was gently inverted 5-6 times as quickly as possible. After the blood was taken, it was placed in an ice box, and then within 30 min, the blood sample was centrifuged for 10 min at 4000 rpm and 4° C. to separate the plasma. Immediately after collection of all plasma, it was stored at −20° C. The concentration of the drug in plasma at each time point was determined after sample collection at all time points.

Based on the data of the average concentration of the drug in plasma versus time after administration obtained as described above, pharmacokinetics-related parameters of male SD rats after the i.g. administration of test compounds (3 mg/kg) were calculated using the Winnonin software according to non-compartment statistical moment theory.

The assay results were shown in Table 4 below. The compounds disclosed herein had superior activity and excellent pharmacokinetic properties as compared with the non-deuterated compound Entrectinib.

TABLE 4

Comparison of PK parameters of representative example compounds and Entrectinib control

| Compound No. | $T_{max}$ (h) | $C_{max}$ (ng/mL) | $AUC_{last}$ (h*ng/mL) | MRT (h) | $Cl_{pred}$ (L/h/kg) | F (%) |
| --- | --- | --- | --- | --- | --- | --- |
| Entrectinib | 2.17 | 236.1 | 1459.5 | 4.24 | 6.83 | 9.23 |
| T-1 | 3.33 | 144.9 | 1065.4 | 5.31 | 9.29 | 7.43 |
| T-3 | 3.33 | 237.1 | 1550.2 | 4.91 | 24.66 | 13.03 |
| T-7 | 4.00 | 278.2 | 1774.5 | 5.28 | 5.85 | 13.67 |
| T-8 | 3.33 | 254.1 | 1525.6 | 4.42 | 6.76 | 11.78 |

It should be understood that these examples are only for illustrating the present disclosure and are not intended to limit the scope disclosed herein. Experimental methods that do not specify specific conditions in the examples are generally based on conventional conditions or conditions recommended by the manufacturer. Parts and percentages are parts by weight and percentages by weight unless otherwise indicated.

The above content is a further detailed description disclosed herein in combination with specific preferred embodiments, and it cannot be assumed that the specific implementation disclosed herein is limited to these descriptions. For a person of ordinary skill in the art to which the present disclosure belongs, a number of simple deductions or substitutions can be made without departing from the concept disclosed herein, and should all be considered as falling within the protection scope disclosed herein.

What is claimed is:

1. A compound of formula (I), or a pharmaceutically acceptable salt, a prodrug, a crystalline form, a stereoisomer, a tautomer, a hydrate or a solvate thereof:

Formula (I)

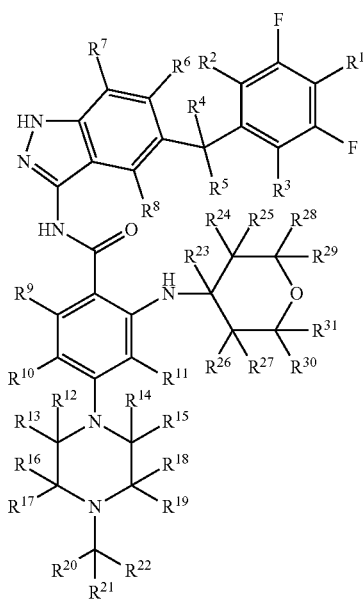

wherein:
$R^1, R^2, R^3, R^4, R^5, R^6, R^7, R^8, R^9, R^{12}, R^{13}, R^{14}, R^{15}, R^{16}, R^{17}, R^{18}, R^{19}, R^{20}, R^{21}, R^{22}, R^{23}, R^{24}, R^{25}, R^{26}, R^{27}, R^{28}, R^{29}, R^{30}$ and $R^{31}$ are each independently selected from the group consisting of hydrogen, deuterium, halogen and trifluoromethyl;
with the proviso that: at least two of $R^1, R^2, R^3, R^4, R^5, R^6, R^7, R^8, R^9, R^{12}, R^{13}, R^{14}, R^{15}, R^{16}, R^{17}, R^{18}, R^{19}, R^{20}, R^{21}, R^{22}, R^{23}, R^{24}, R^{25}, R^{26}, R^{27}, R^{28}, R^{29}, R^{30}$ and $R^{31}$ are deuterium, and $R^{10}$ and $R^{11}$ are hydrogen.

2. The compound according to claim 1, wherein $R^2$, $R^3$, $R^9$, $R^{23}$, $R^{24}$, $R^{25}$, $R^{26}$ and $R^{27}$ are hydrogen.

3. The compound according to claim 2, wherein $R^4$ and $R^5$ are deuterium.

4. The compound according to claim 2, wherein $R^{28}$, $R^{29}$, $R^{30}$ and $R^{31}$ are deuterium.

5. The compound according to claim 2, wherein $R^{20}$, $R^{21}$ and $R^{22}$ are deuterium.

6. The compound according to claim 2, wherein $R^{12}$, $R^{13}$, $R^{14}$, $R^{15}$, $R^{16}$, $R^{17}$, $R^{18}$ and $R^{19}$ are deuterium.

7. The compound according to claim 1, which is selected from the group consisting of:

Formula (2)

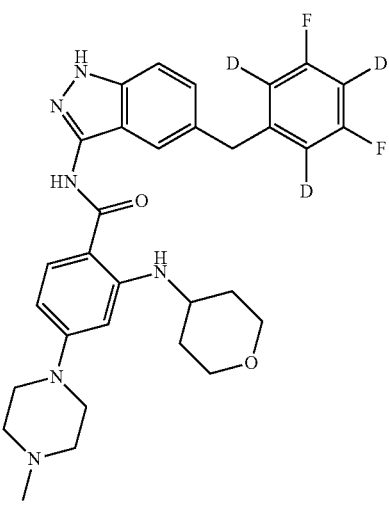

Formula (3)

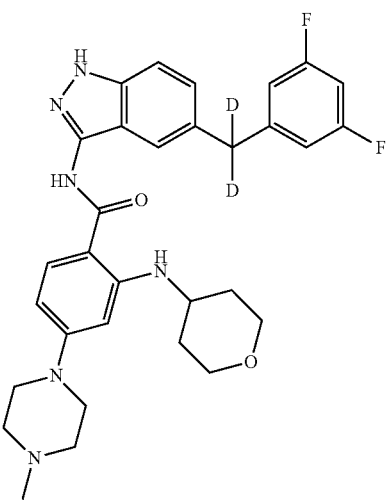

Formula (4)

Formula (8)

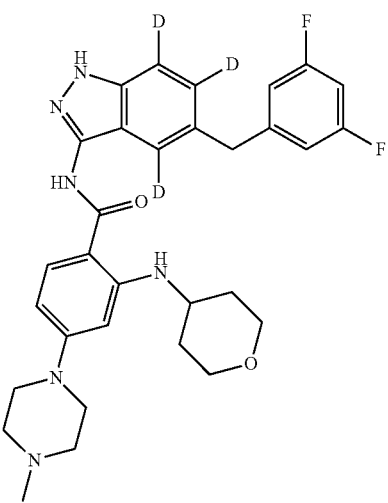

Formula (12)
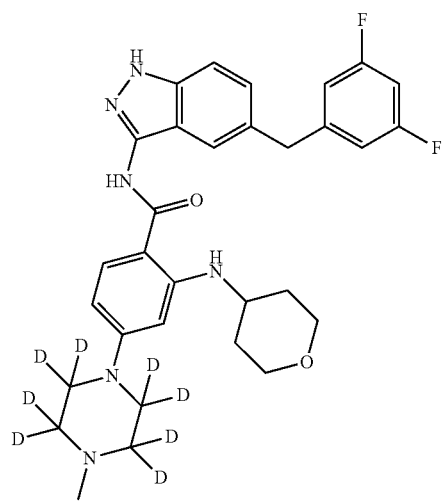
Formula (13)
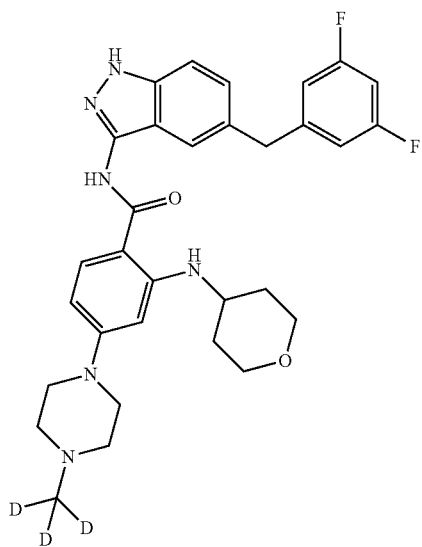
Formula (14)
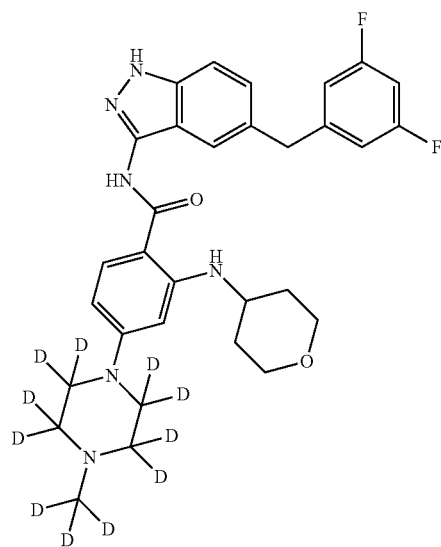
Formula (15)
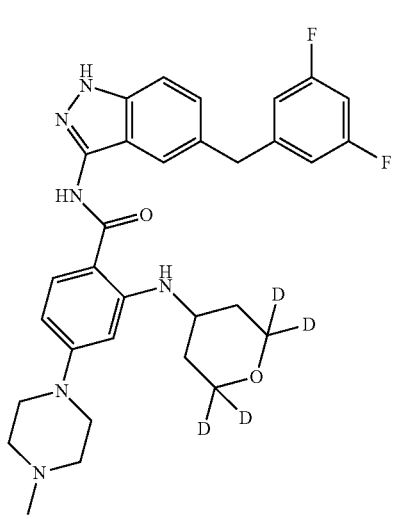
Formula (16)
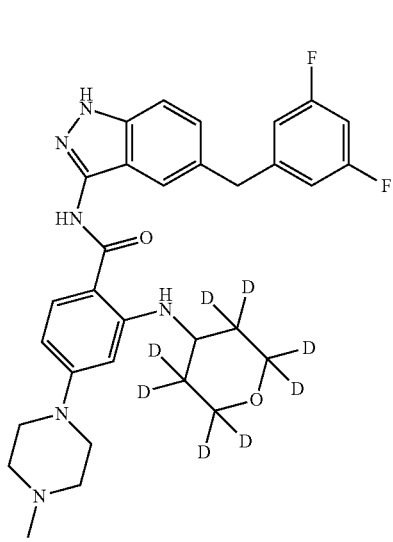
Formula (17)
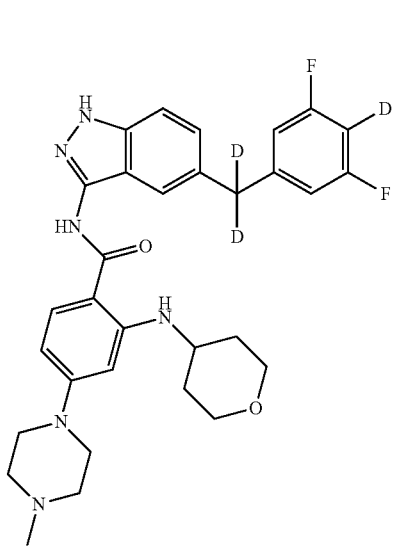

Formula (19)
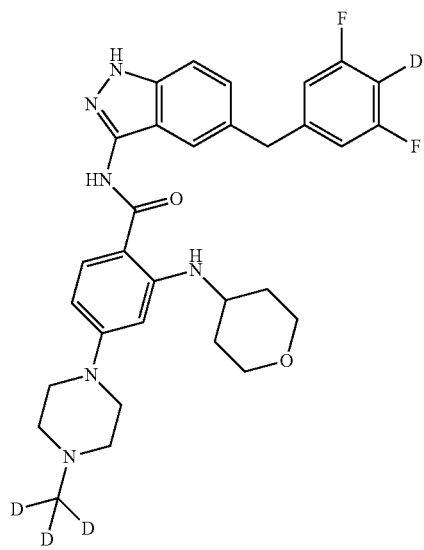
Formula (20)
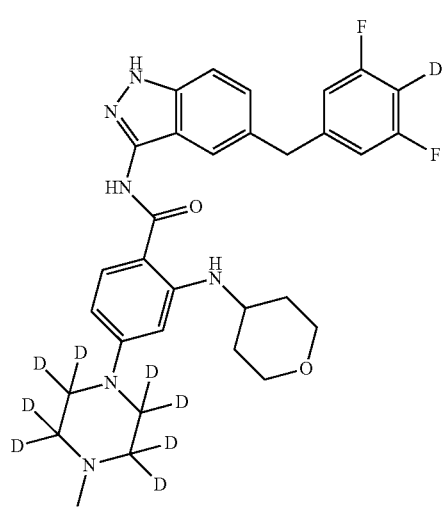
Formula (21)
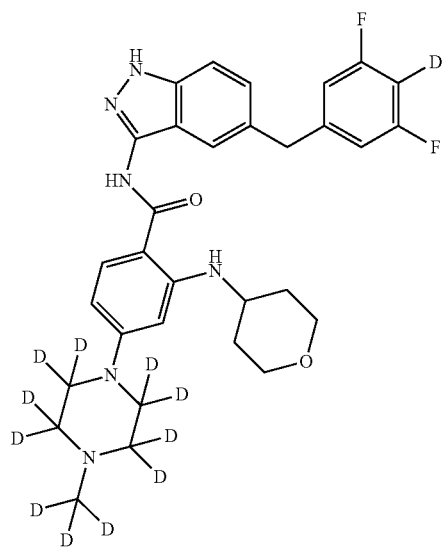
Formula (22)
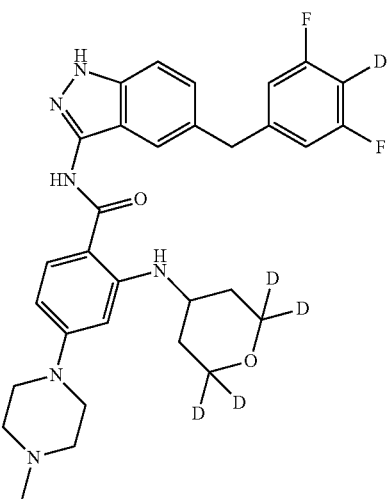
Formula (24)
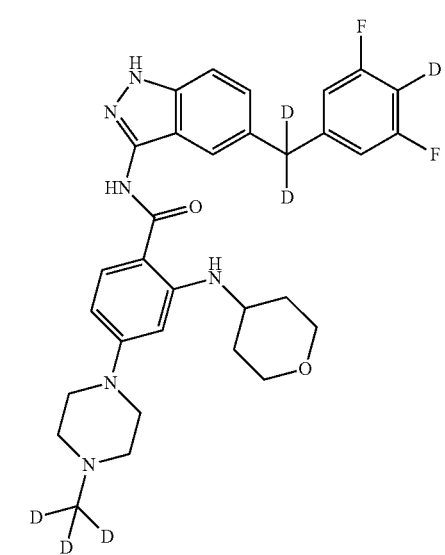
Formula (25)
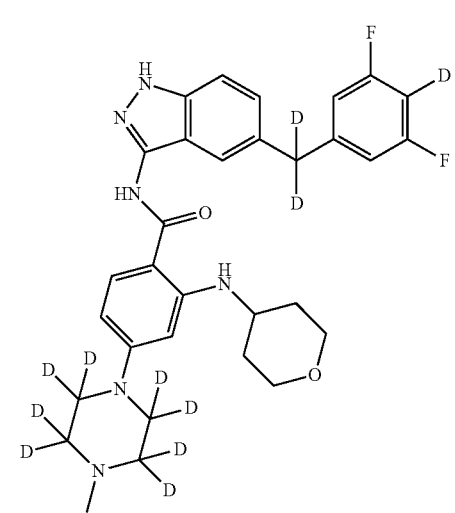 [SMILES: [2H]C([2H])(c1cc(F)cc(F)c1)c1ccc2[nH]nc(NC(=O)c3ccc(N4C([2H])([2H])C([2H])([2H])N(C)C([2H])([2H])C4([2H])[2H])cc3NC3CCOCC3)c2c1]

95 96
-continued -continued
Formula (26)
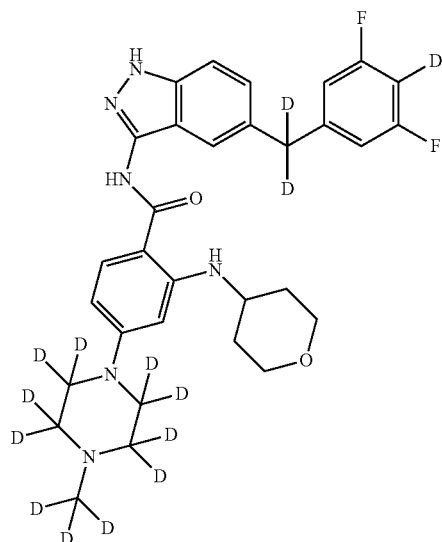
Formula (32)
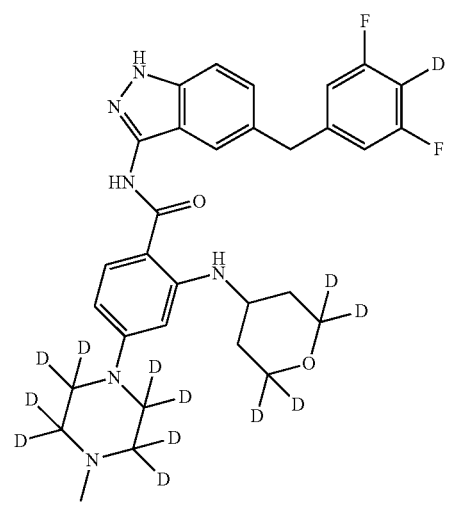
Formula (27)
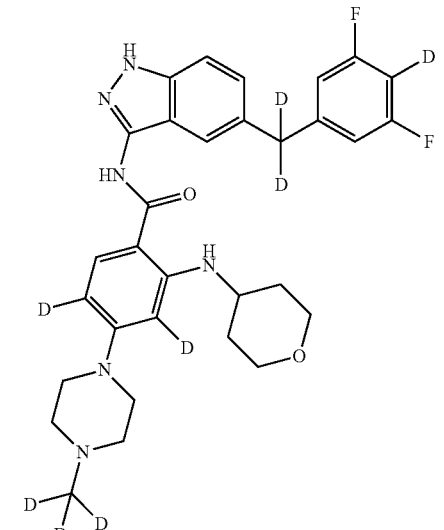
Formula (33)
Formula (31)
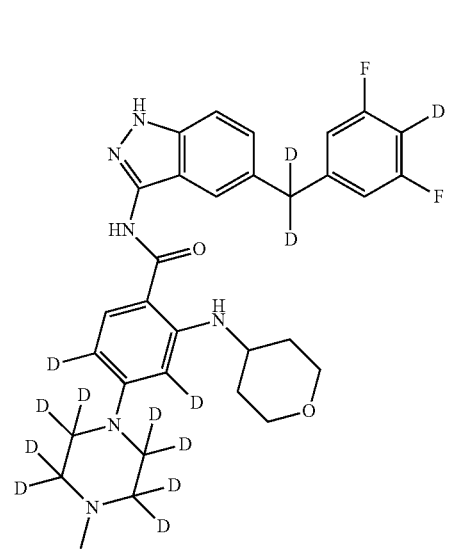
Formula (34)

Formula (35)
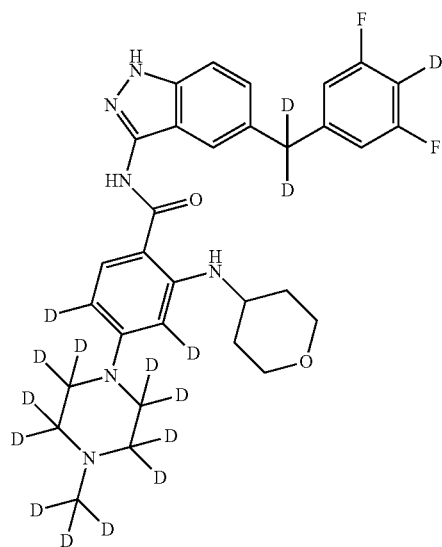
Formula (36)
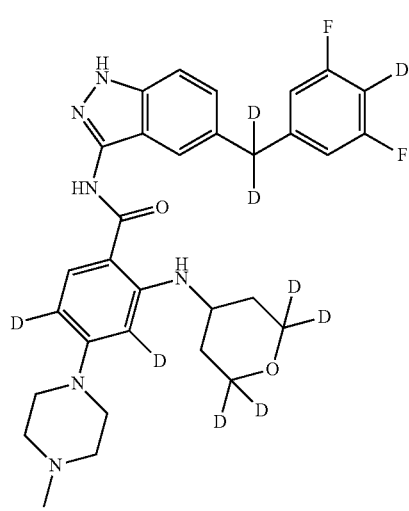
Formula (37)
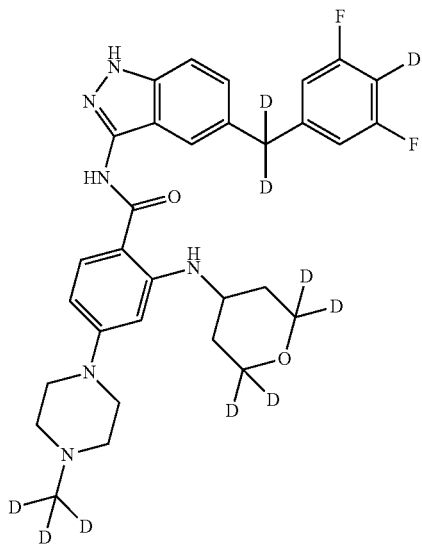
Formula (38)
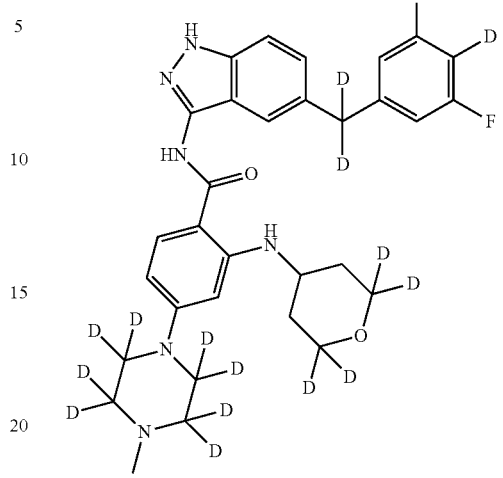
Formula (39)
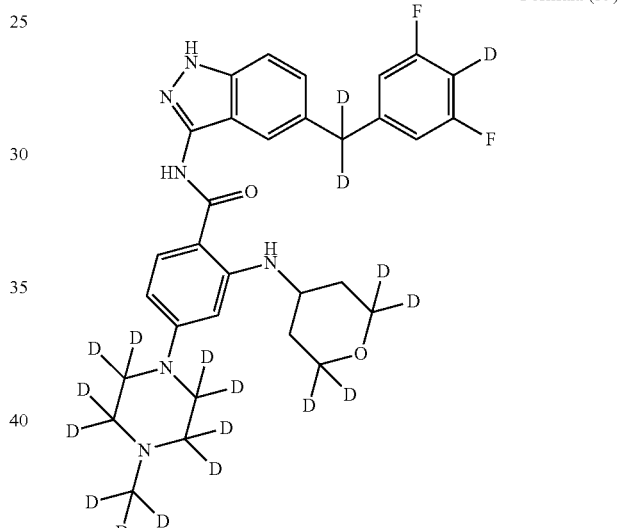
Formula (43)
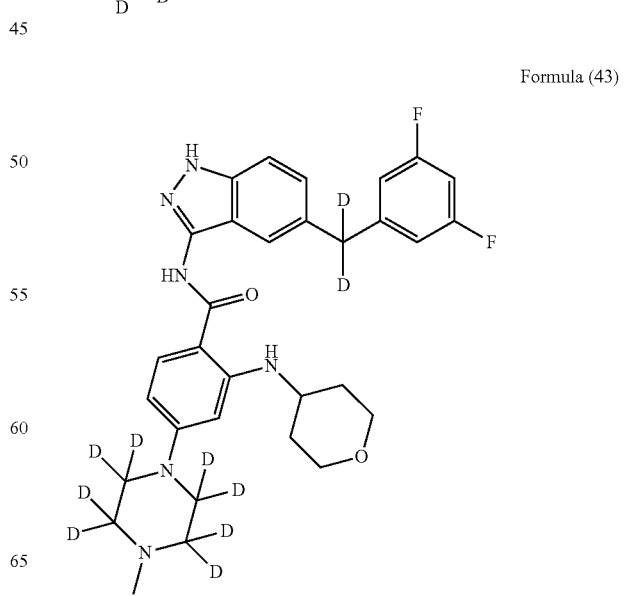

Formula (44)
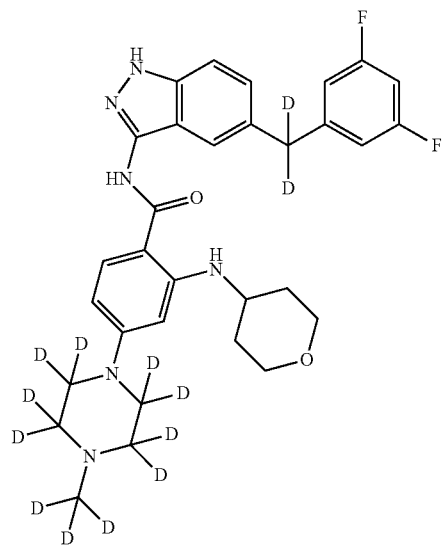
Formula (45)
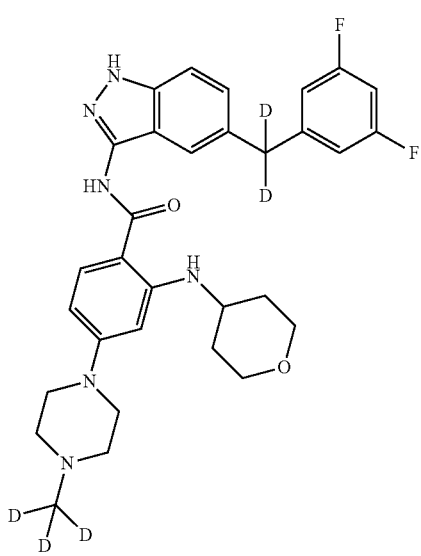
Formula (46)
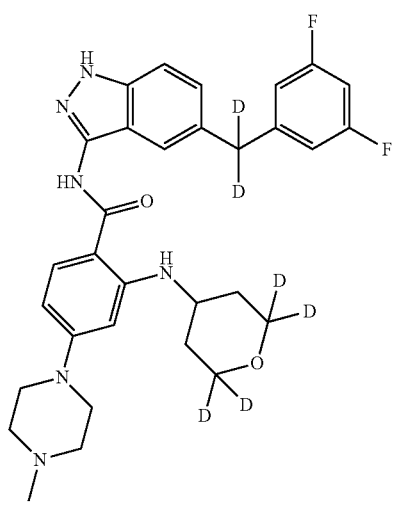
Formula (51)
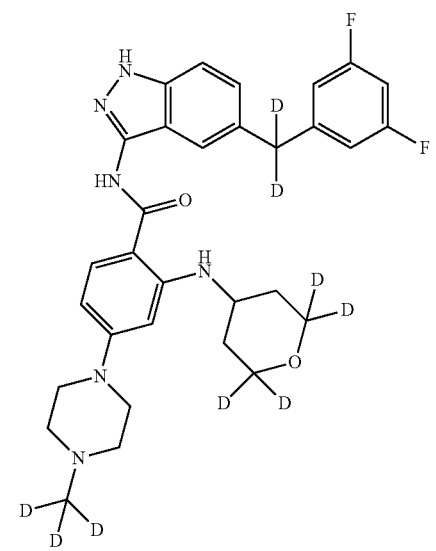
Formula (52)
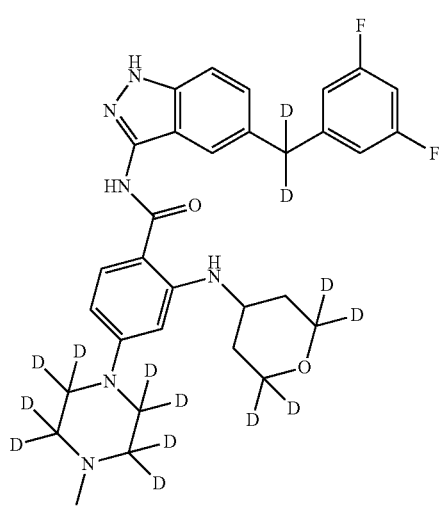
Formula (53)
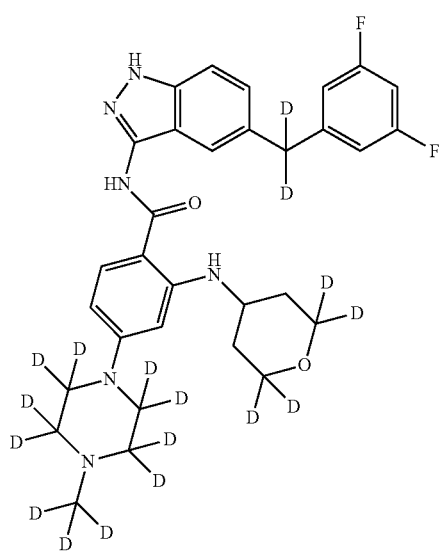

101
-continued

Formula (61)

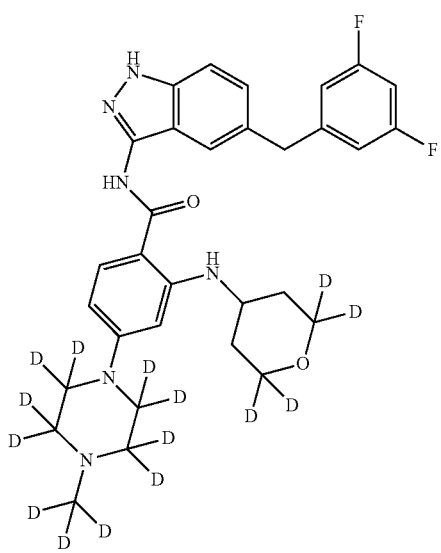

8. A pharmaceutical composition, which comprises a pharmaceutically acceptable carrier and the compound according to claim 1, or a pharmaceutically acceptable salt, a prodrug, a crystalline form, a stereoisomer, a tautomer, a hydrate or a solvate thereof.

9. A method of treating the related cancers caused by deregulation of the activity of protein kinase selected from the group consisting of ALK, ROS1, TRK1, TRK2 and TRK3 in a subject, comprising administering to the subject the compound according to claim 1, or a pharmaceutically acceptable salt, a prodrug, a crystalline form, a stereoisomer, a tautomer, a hydrate or a solvate thereof.

10. The method according to claim 9, wherein the cancer is selected from the group consisting of non-small cell lung cancer, neuroblastoma, colorectal cancer, anaplastic large cell lymphoma, bile duct cancer, gastric cancer, spongioblastoma, leiomyosarcoma, melanoma, squamous cell lung cancer, ovarian cancer, pancreatic cancer, prostate cancer, breast cancer, medullary thyroid carcinoma, and thyroid papillary carcinoma.

11. The compound according to claim 3, wherein $R^{20}$, $R^{21}$ and $R^{22}$ are deuterium.

12. The compound according to claim 11, wherein $R^{12}$, $R^{13}$, $R^{14}$, $R^{15}$, $R^{16}$, $R^{17}$, $R^{18}$ and $R^{19}$ are deuterium.

13. The compound according to claim 3, wherein $R^{12}$, $R^{13}$, $R^{14}$, $R^{15}$, $R^{16}$, $R^{17}$, $R^{18}$ and $R^{19}$ are deuterium.

14. The compound according to claim 4, wherein $R^{12}$, $R^{13}$, $R^{14}$, $R^{15}$, $R^{16}$, $R^{17}$, $R^{18}$ and $R^{19}$ are deuterium.

15. The compound according to claim 5, wherein $R^{12}$, $R^{13}$, $R^{14}$, $R^{15}$, $R^{16}$, $R^{17}$, $R^{18}$ and $R^{19}$ are deuterium.

102

16. The compound according to claim 1, which is the following compound:

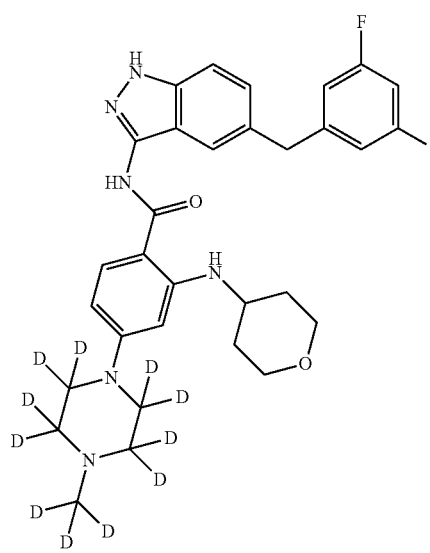

T-3 or a pharmaceutically acceptable salt thereof.

17. The compound according to claim 1, which is the following compound:

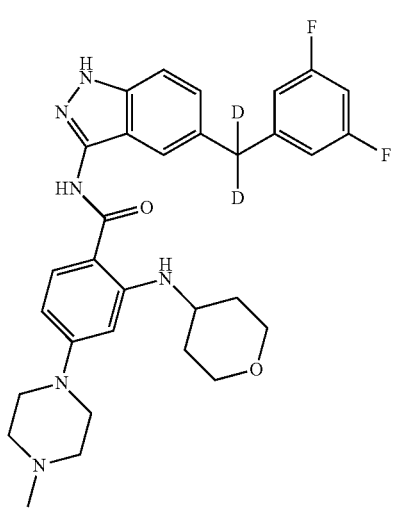

T-7 or a pharmaceutically acceptable salt thereof.

18. The compound according to claim 1, which is the following compound:

T-8

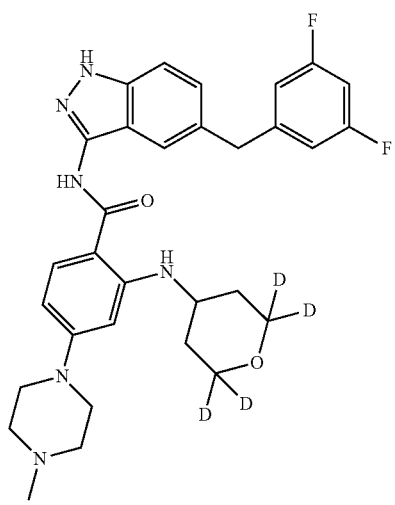

or a pharmaceutically acceptable salt thereof.

19. A compound selected from the following:

T-4

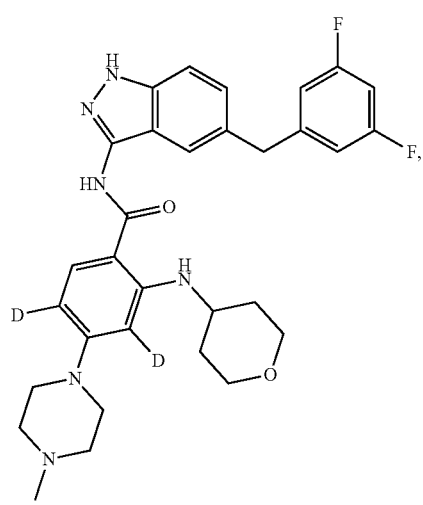

T-6

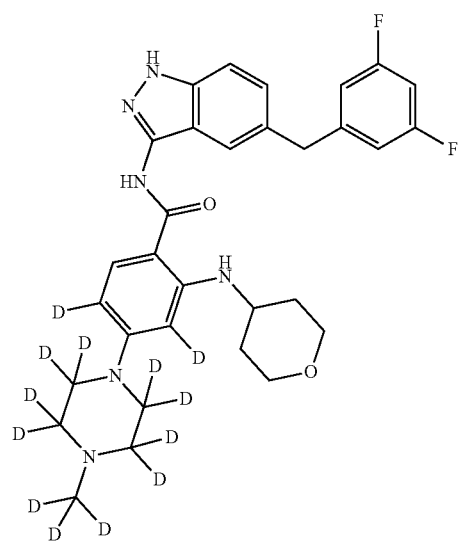

or

-continued

T-12

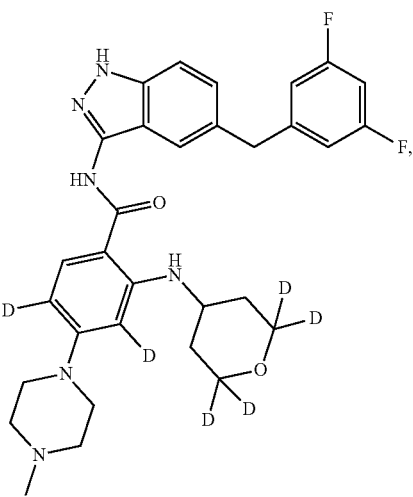

or a pharmaceutically acceptable salt, a prodrug, a crystalline form, a stereoisomer, a tautomer, a hydrate or a solvate thereof.

20. A pharmaceutical composition, which comprises a pharmaceutically acceptable carrier and the compound according to claim 19, or a pharmaceutically acceptable salt, a prodrug, a crystalline form, a stereoisomer, a tautomer, a hydrate or a solvate thereof.

21. A compound of formula T-9

T-9

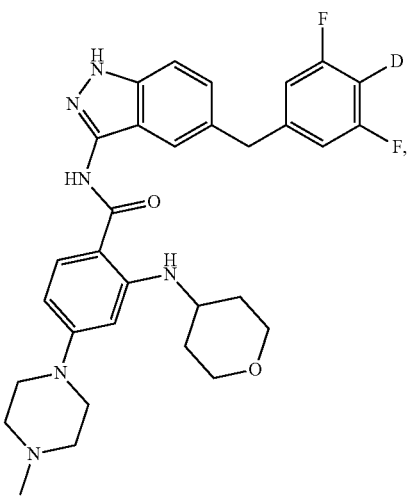

or a pharmaceutically acceptable salt, a prodrug, a crystalline form, a stereoisomer, a tautomer, a hydrate or a solvate thereof; wherein the content of the deuterium isotope at the deuterated position is at least greater than the natural content of the deuterium isotope.

22. A pharmaceutical composition, which comprises a pharmaceutically acceptable carrier and the compound according to claim 21, or a pharmaceutically acceptable salt, a prodrug, a crystalline form, a stereoisomer, a tautomer, a hydrate or a solvate thereof.

* * * * *